United States Patent
Radvanyi et al.

(10) Patent No.: US 9,512,401 B2
(45) Date of Patent: Dec. 6, 2016

(54) B AND T LYMPHOCYTE ATTENUATOR MARKER FOR USE IN ADOPTIVE T-CELL THERAPY

(75) Inventors: Laszlo Radvanyi, Houston, TX (US); Patrick Hwu, Houston, TX (US); Chantale Bernatchez, Spring, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 336 days.

(21) Appl. No.: 13/876,198

(22) PCT Filed: Sep. 30, 2011

(86) PCT No.: PCT/US2011/054222
§ 371 (c)(1),
(2), (4) Date: Jun. 4, 2013

(87) PCT Pub. No.: WO2012/044933
PCT Pub. Date: Apr. 5, 2012

(65) Prior Publication Data
US 2013/0302300 A1    Nov. 14, 2013

Related U.S. Application Data

(60) Provisional application No. 61/389,127, filed on Oct. 1, 2010.

(51) Int. Cl.
*A61K 35/28* (2015.01)
*A61K 38/00* (2006.01)
*C12N 5/0783* (2010.01)
*A61K 35/17* (2015.01)

(52) U.S. Cl.
CPC ........... *C12N 5/0636* (2013.01); *A61K 35/17* (2013.01)

(58) Field of Classification Search
None
See application file for complete search history.

(56) References Cited

U.S. PATENT DOCUMENTS

2009/0246220 A1* 10/2009 Ertl et al. ............ 424/192.1

OTHER PUBLICATIONS

Wong et al., J of immunotherapy, 1991, v.10, pp. 120-130).*
Patios et al ., J of Clinical Investigation, 2010, v.120, pp. 76-80.*
Derré et al., "BTLA mediates inhibition of human tumor-specific CD8+ T cells that can be partially reversed by vaccination," *Journal of Clinical Investigation*, 120:157-167, 2010.
Han et al., "Soluble B and T lymphocyte attenuator possesses antitumor effects and facilitates heat shock protein 70 vaccine-triggered antitumor immunity against a murine TC-1 cervical cancer model in vivo," *Journal of Immunology*, 183(12):7842-7850, 2009.
M'Hidi et al., "High expression of the inhibitory receptor BTLA in T-follicular helper cells and in B-cell small lymphocytic lymphoma/chronic lymphocytic leukemia," *American Journal of Clinical Pathology*, 132:589-596, 2009.
Otsuki et al., "Expression and function of the B and T lymphocyte attenuator (BTLA/CD272) on human T cells," *Biochemical and Biophysical Research Communications*, 344(4):1121-1127, 2006.
PCT International Preliminary Report on Patentability issued in International Application No. PCT/US2011/054222, issued Apr. 2, 2013.
PCT International Search Report issued in International Application No. PCT/US2011/054222, mailed Apr. 24, 2012.
Radvanyi et al., "Specific lymphocyte subsets predict response to adoptive cell therapy using expanded autologous tumor-infiltrating lymphocytes in metastatic melanoma patients," *Clin Cancer Res*, 18(24):6758-6770, 2012.
Wang et al., "Distinct expression and inhibitory function of B and T lymphocyte attenuator on human T cells," *Tissue Antigens*, 69(2):145-153, 2007.

* cited by examiner

*Primary Examiner* — Michail Belyavskyi
(74) *Attorney, Agent, or Firm* — Parker Highlander PLLC

(57) ABSTRACT

BTLA-positive ("BTLA+") lymphocyte signaling drives T cells and kills tumors. BTLA functions as a positive modulator of anti-tumor (anti-melanoma) T cell responses, The BTLA+ T cell responds against tumor or cancer cells, and, in cancer patients respond better to IL-2 than BTLA-negative cells. Hence, the BTLA-positive T cell in cancers is a positive marker for selection of enriched anti-tumor-cancer reactive T cells and can be used or applied for adoptive T-cell therapy or for therapeutic purposes.

12 Claims, 53 Drawing Sheets

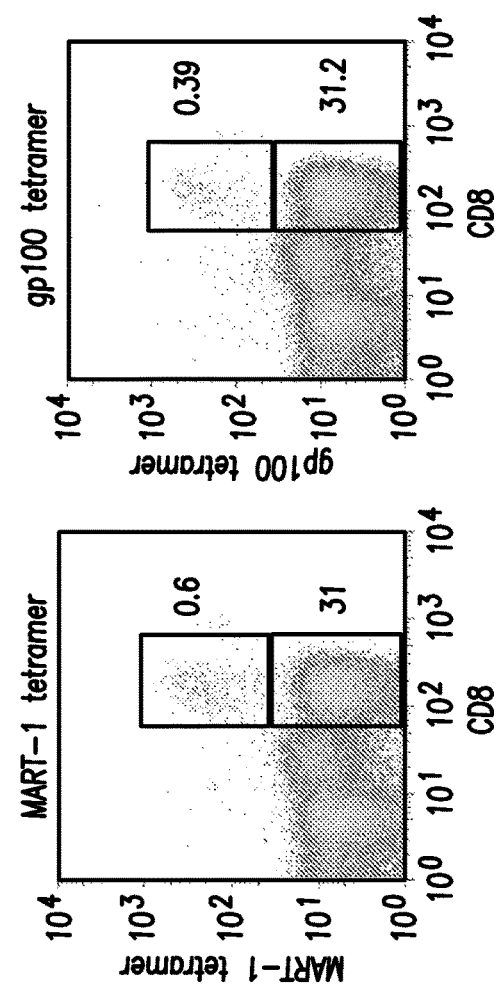
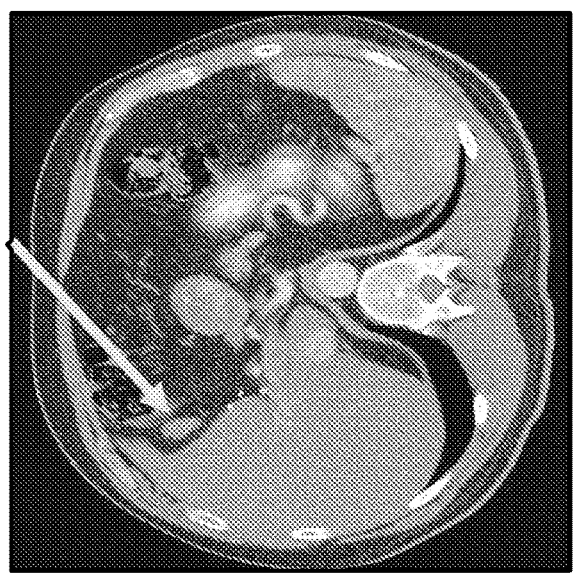
FIG.1C
FIG.1B
FIG.1A

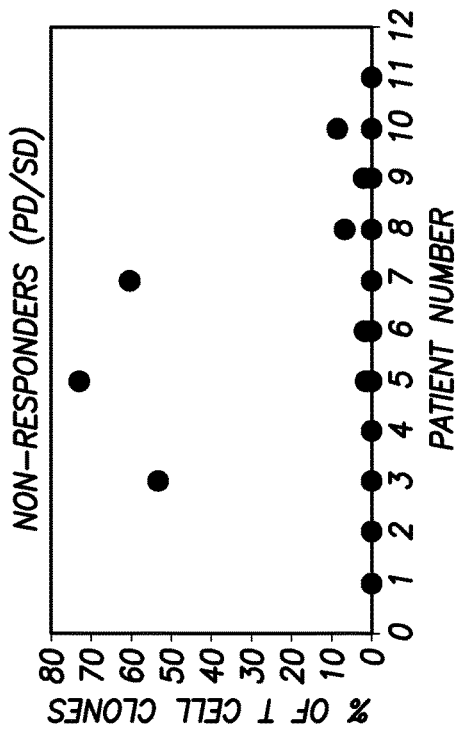
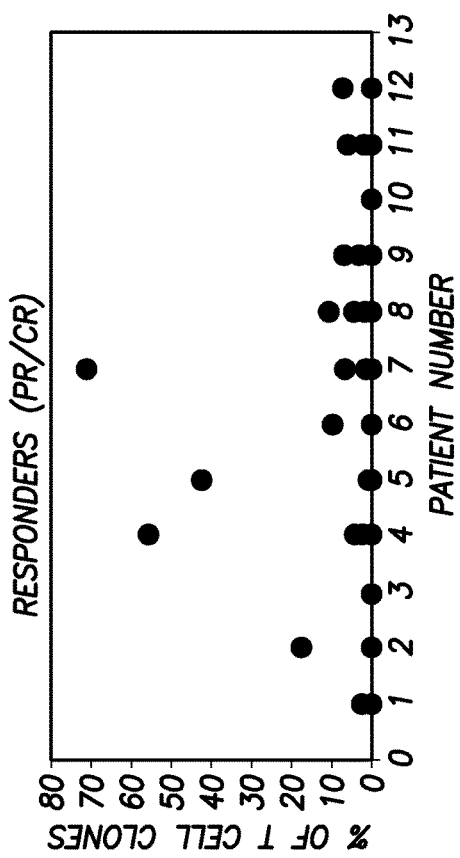

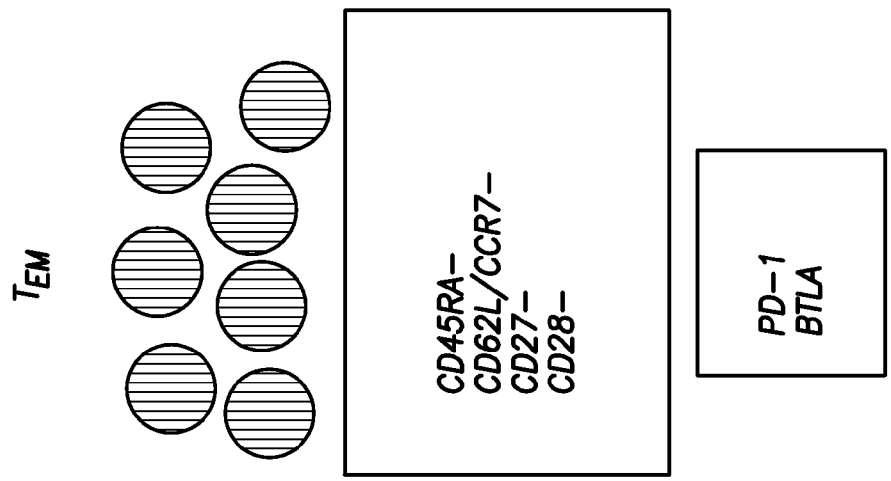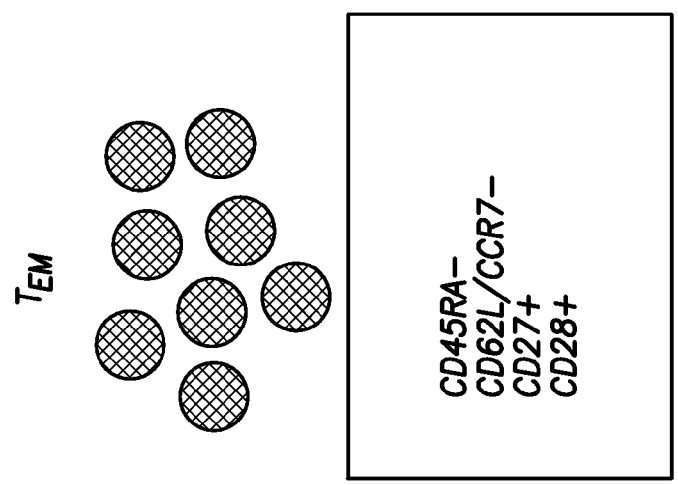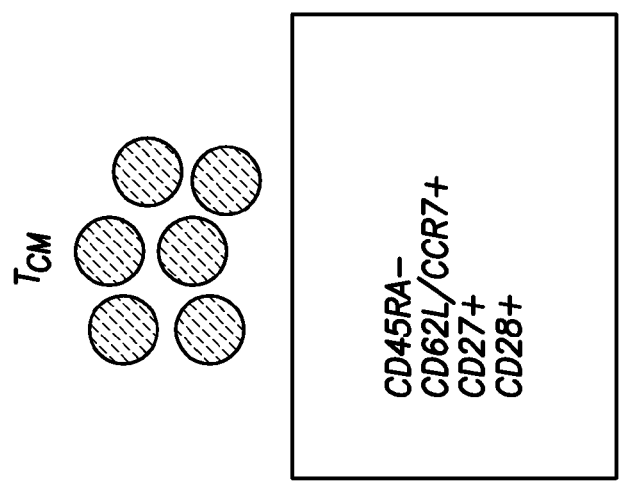
FIG.11

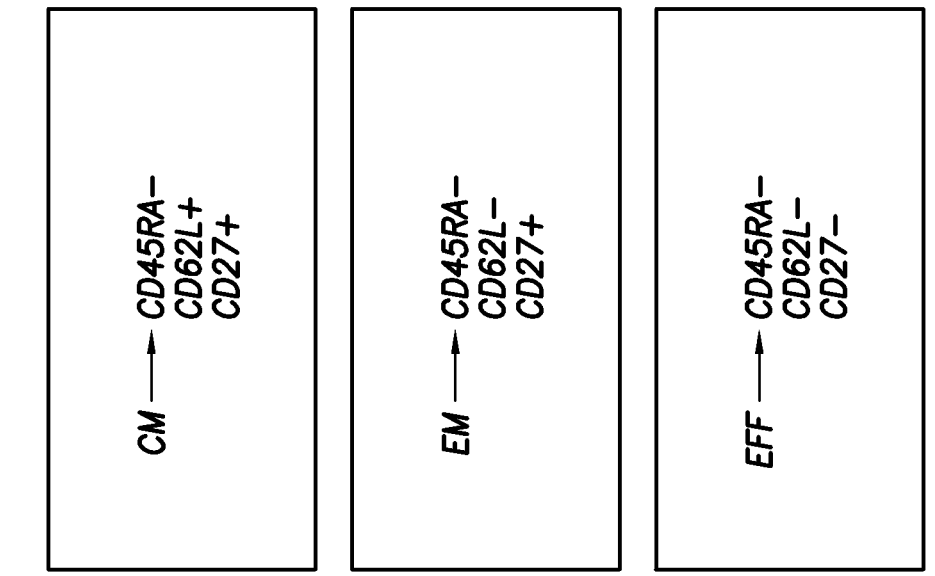
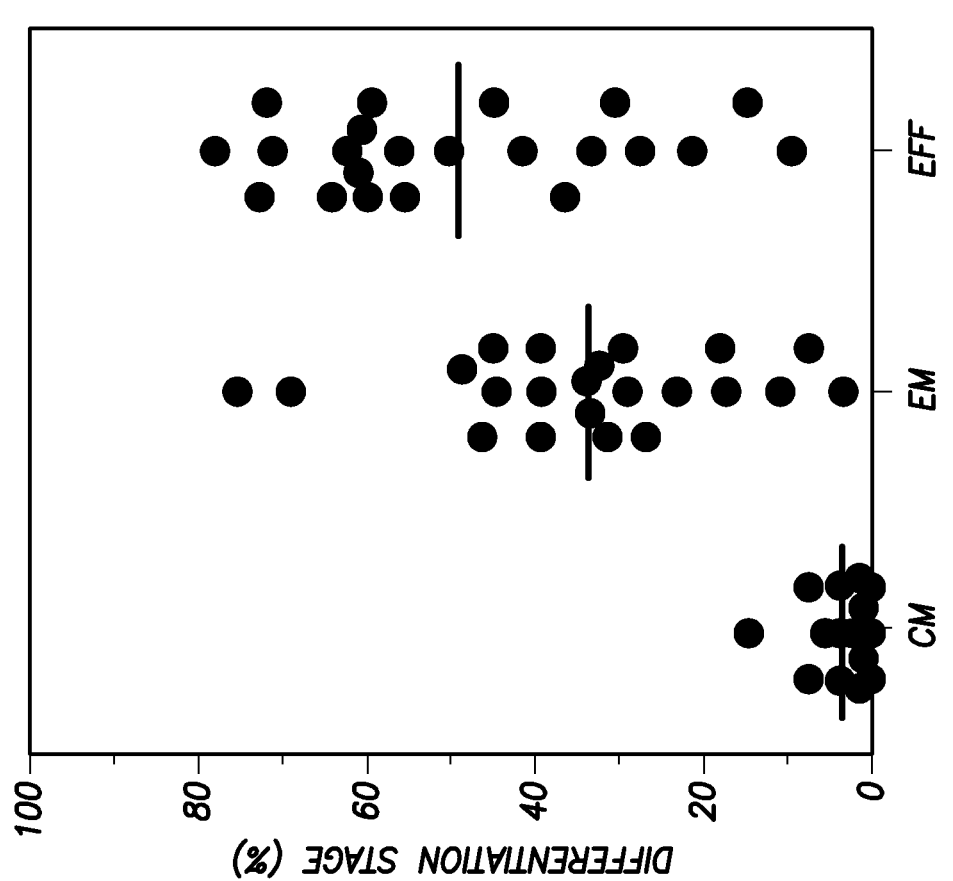
FIG. 13

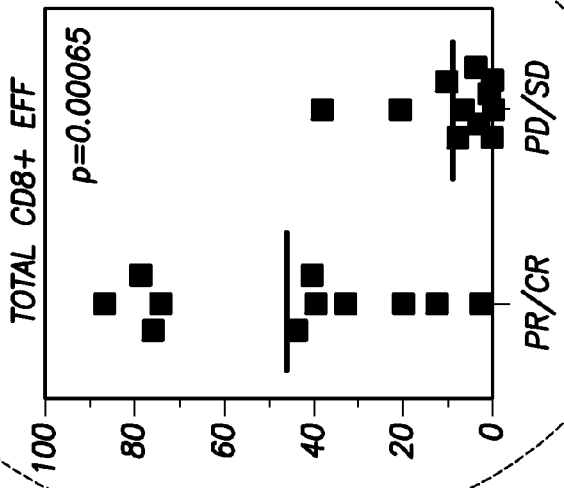
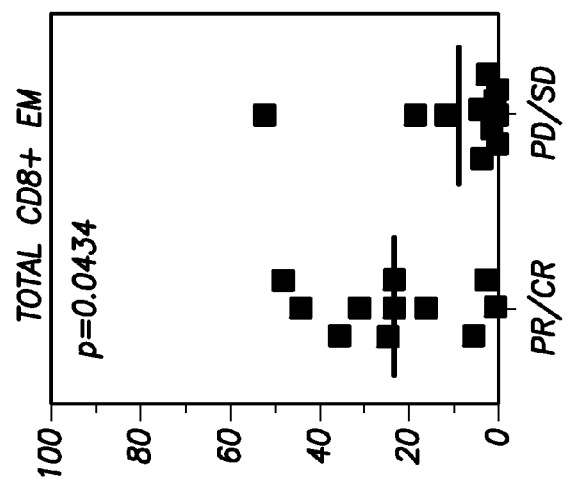
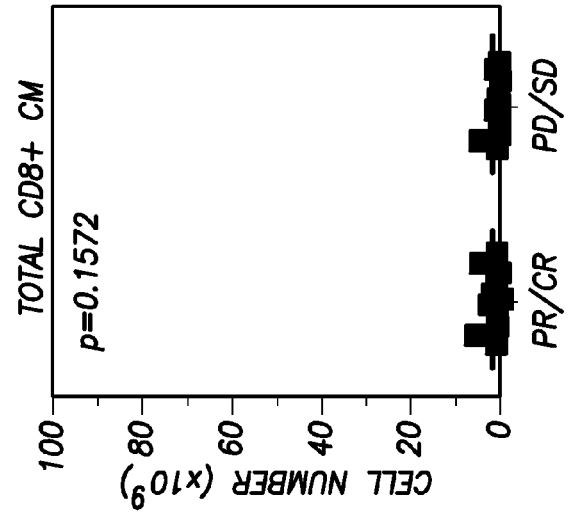
FIG. 14C
FIG. 14B
FIG. 14A

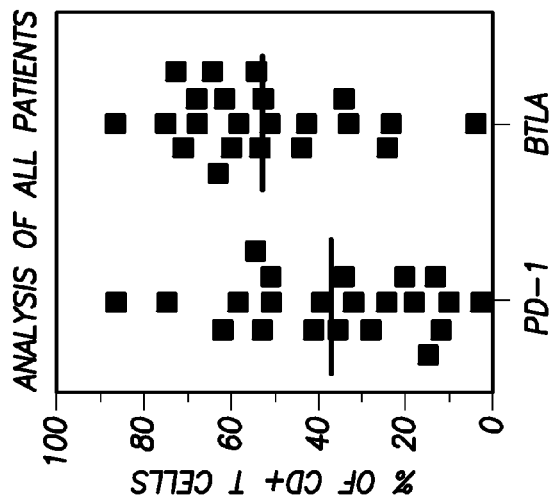
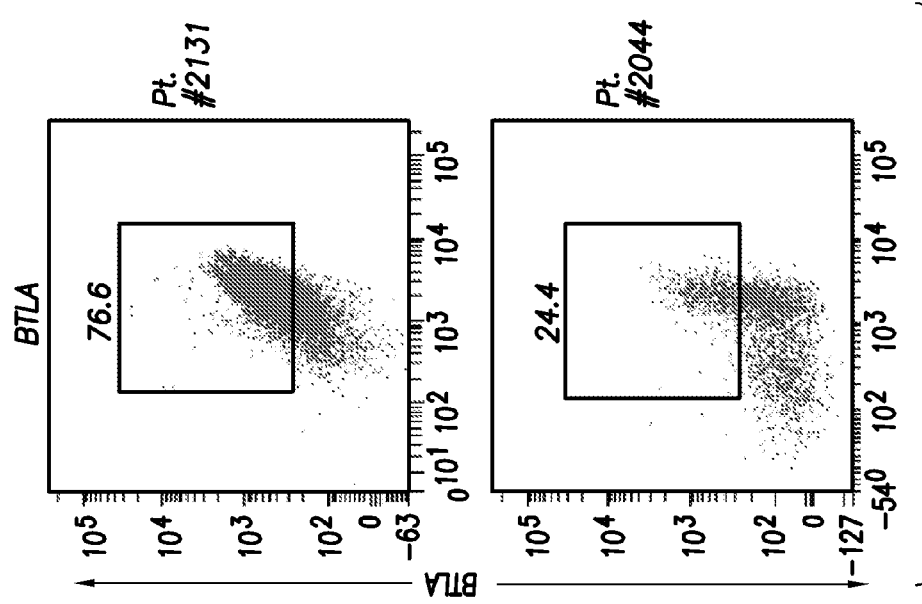
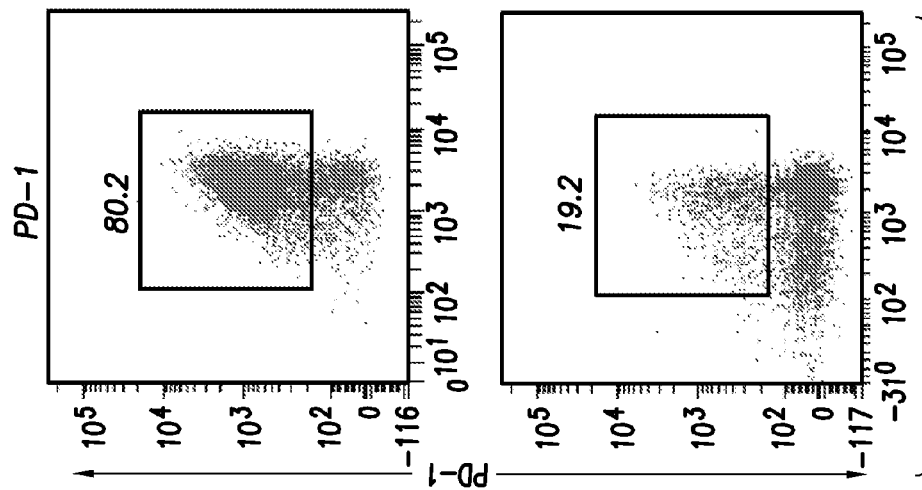
FIG.15C
FIG.15B
FIG.15A

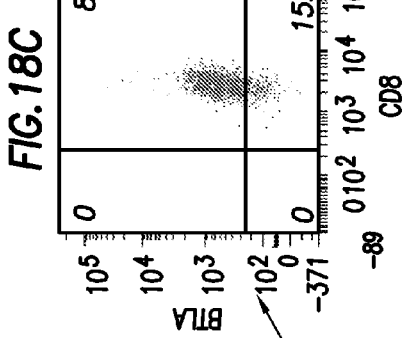
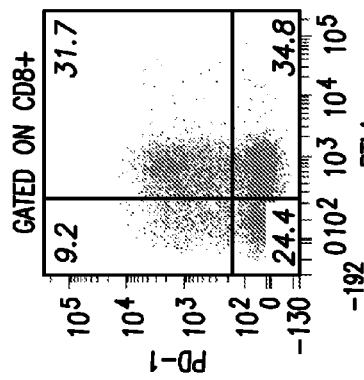
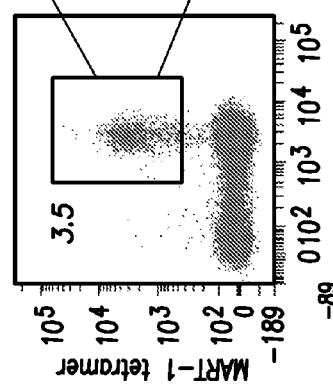
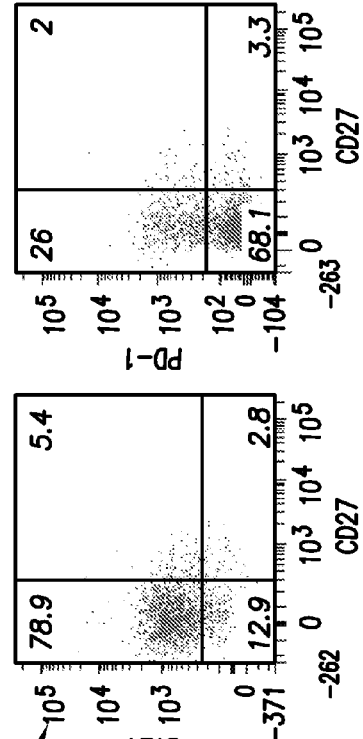

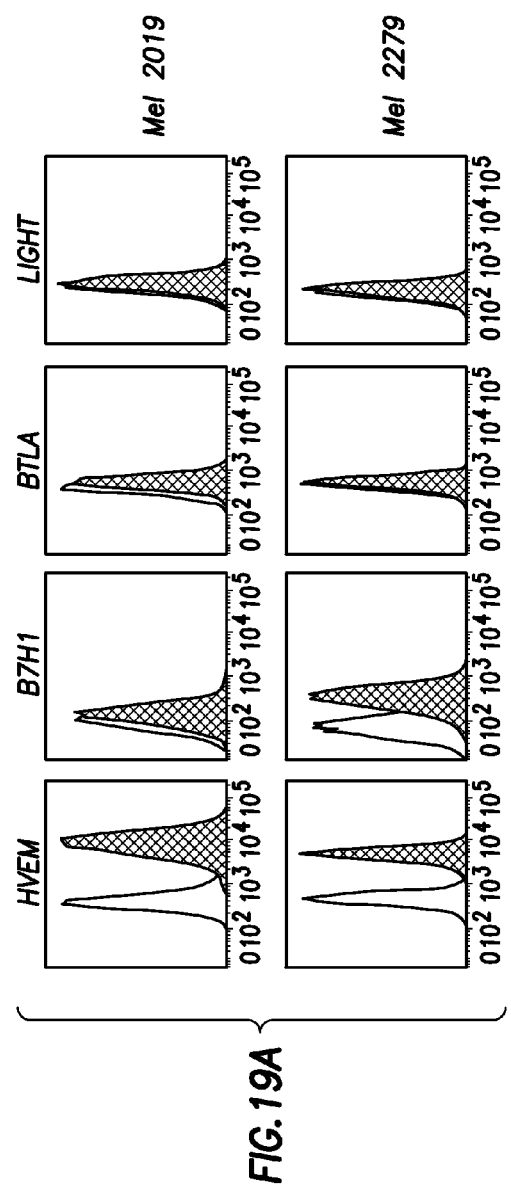
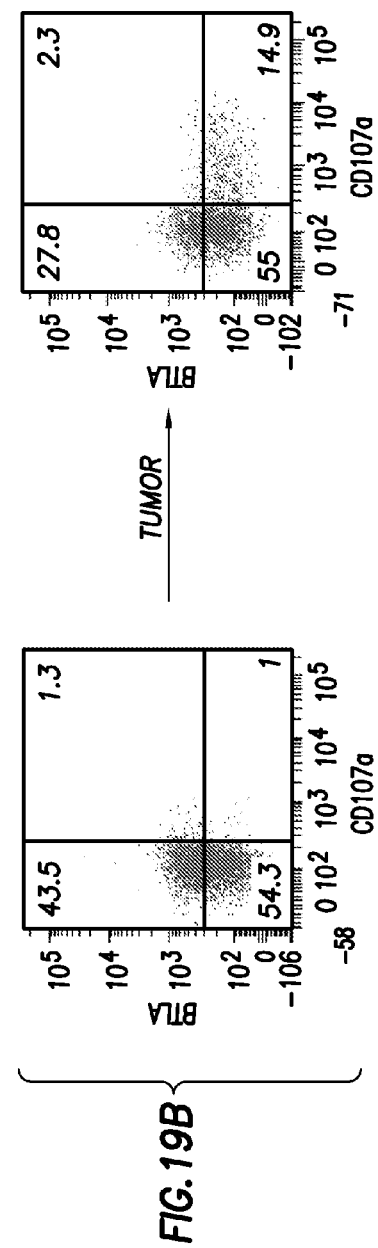
FIG. 19A
FIG. 19B

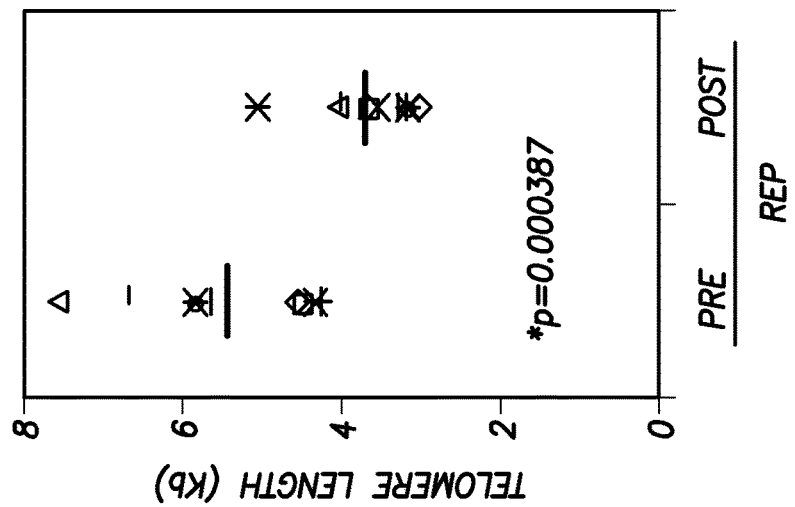
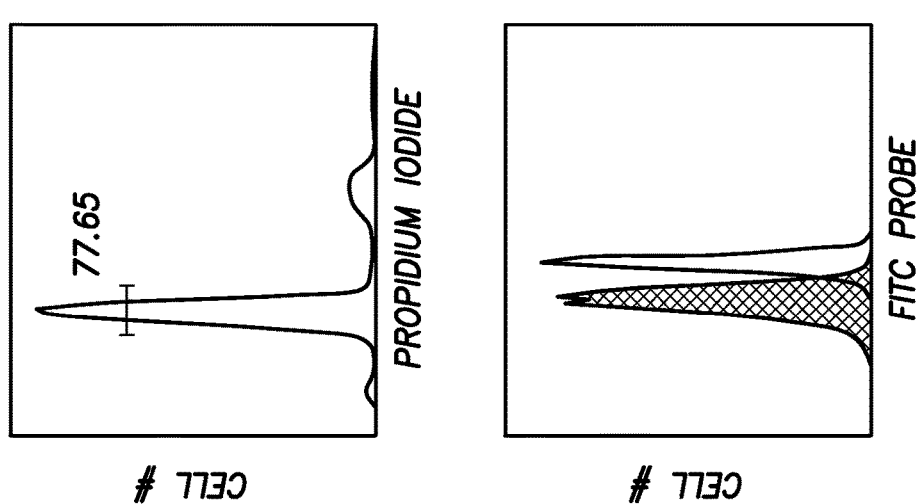
FIG.20A
FIG.20B

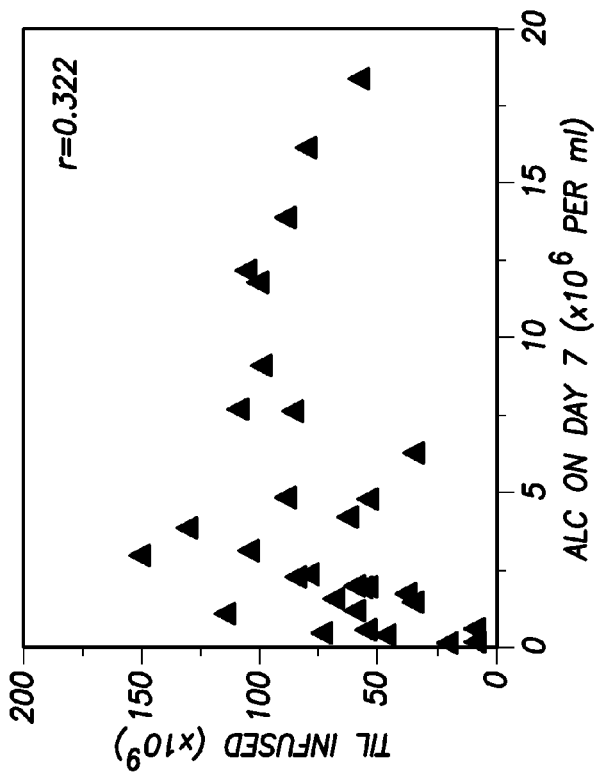
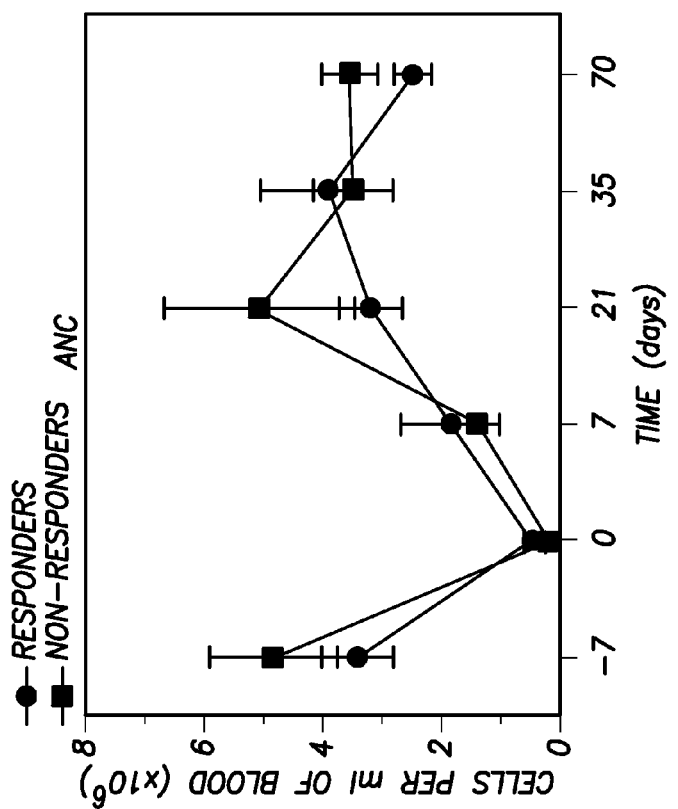
FIG. 26D
FIG. 26C

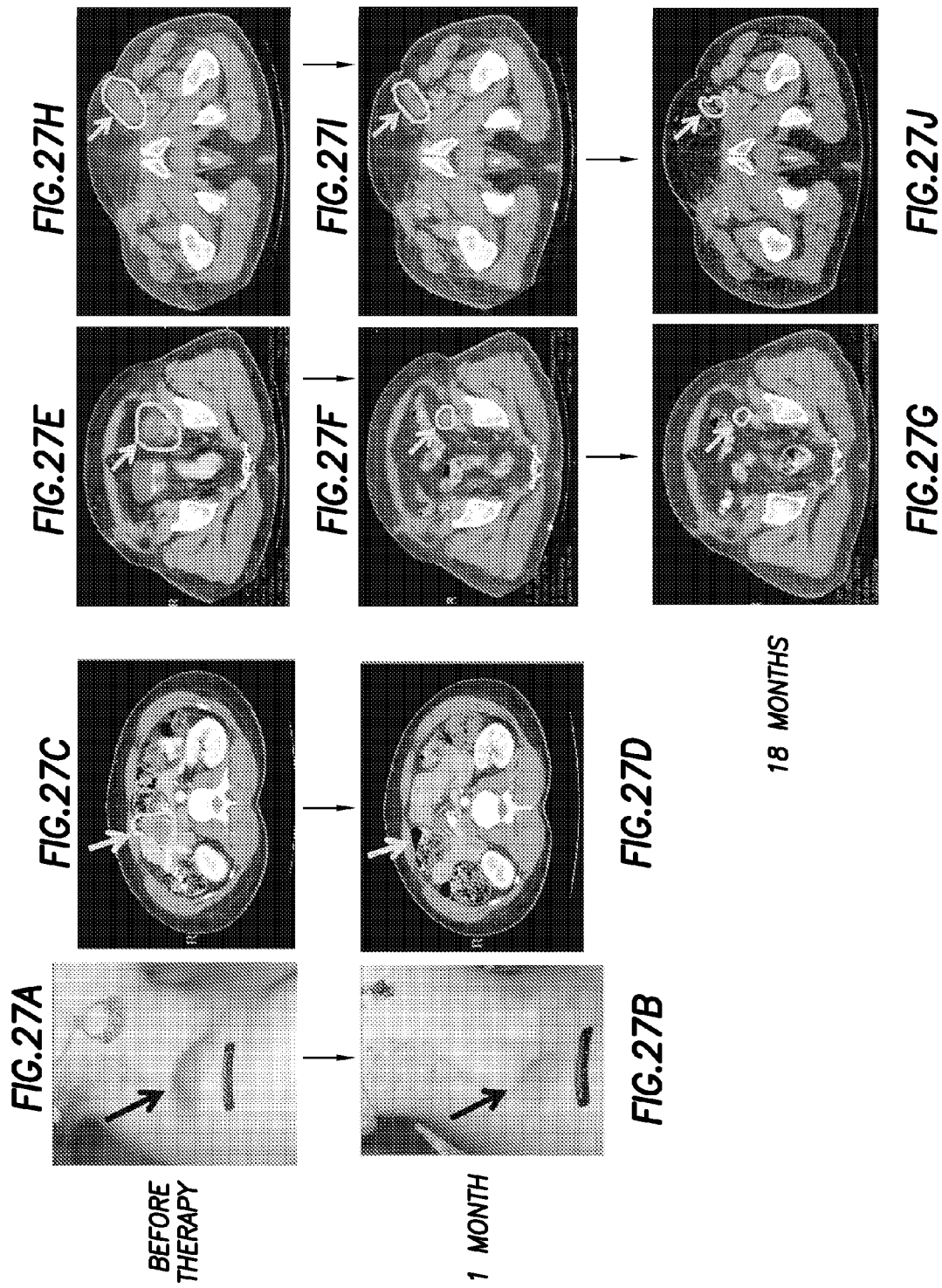

PATIENT #2262

BEFORE THERAPY

6 WEEKS

18 MONTHS
(DURABLE RESPONSE)

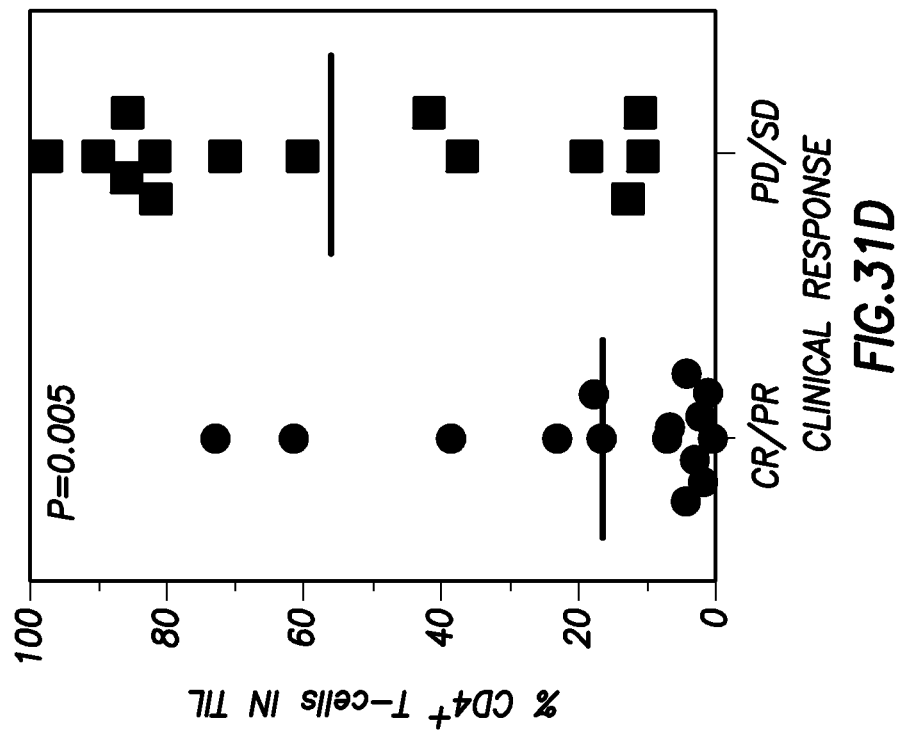
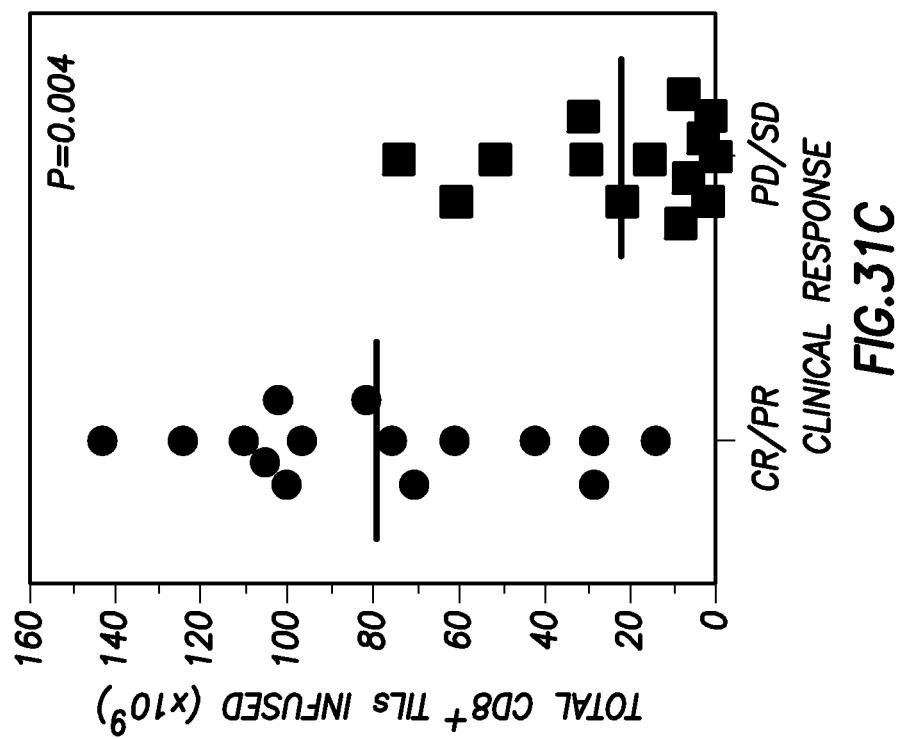
FIG. 31C
FIG. 31D

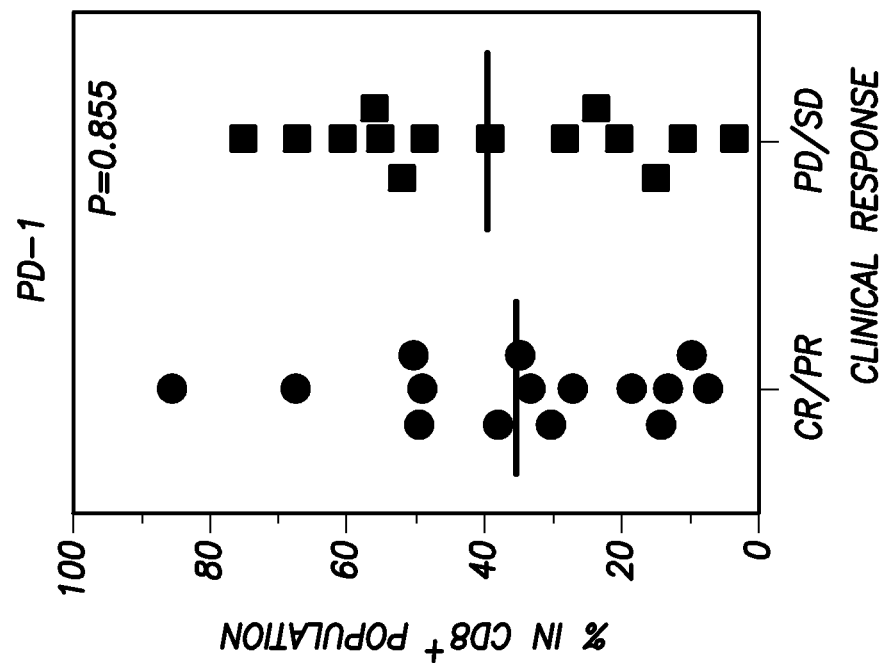
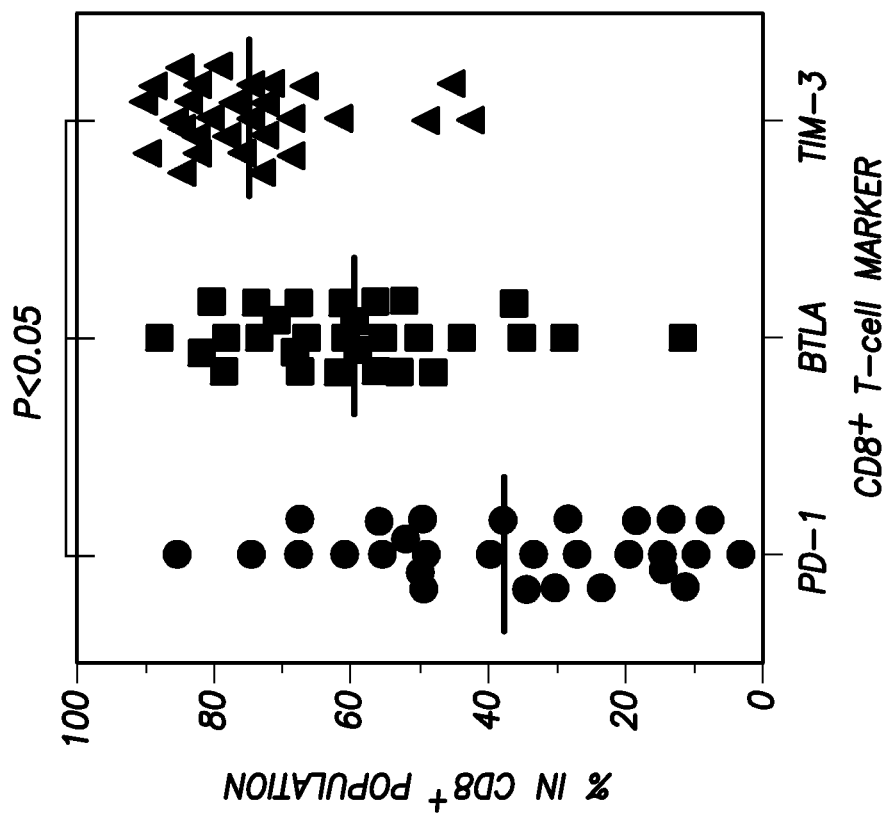
FIG.34B
FIG.34A

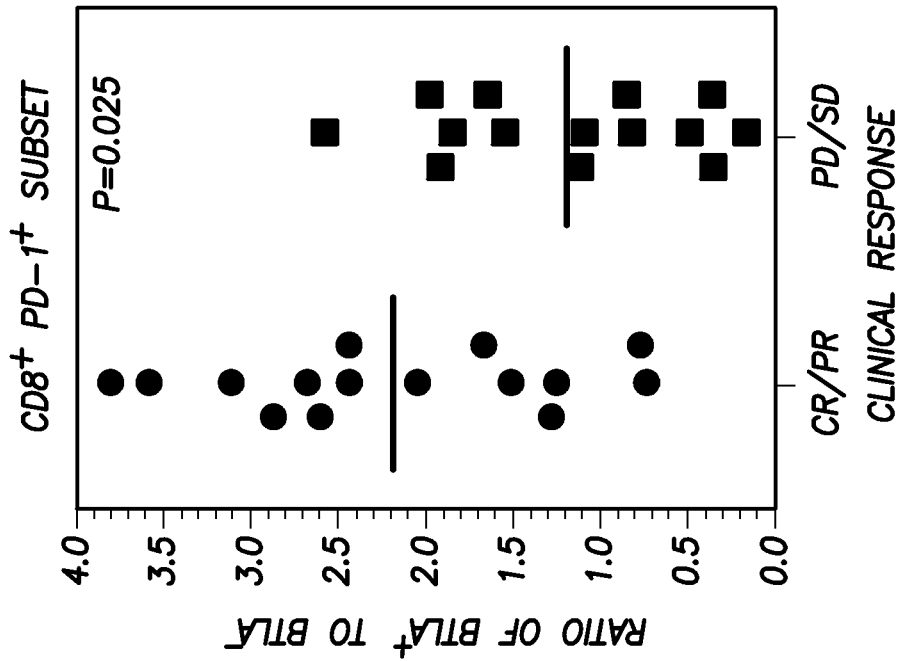
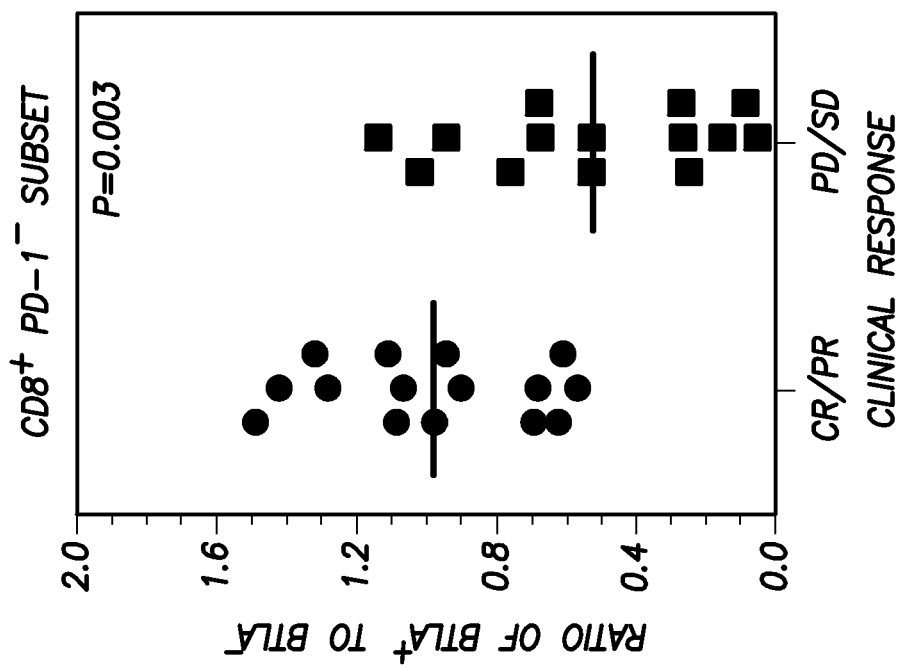
FIG. 34H
FIG. 34G

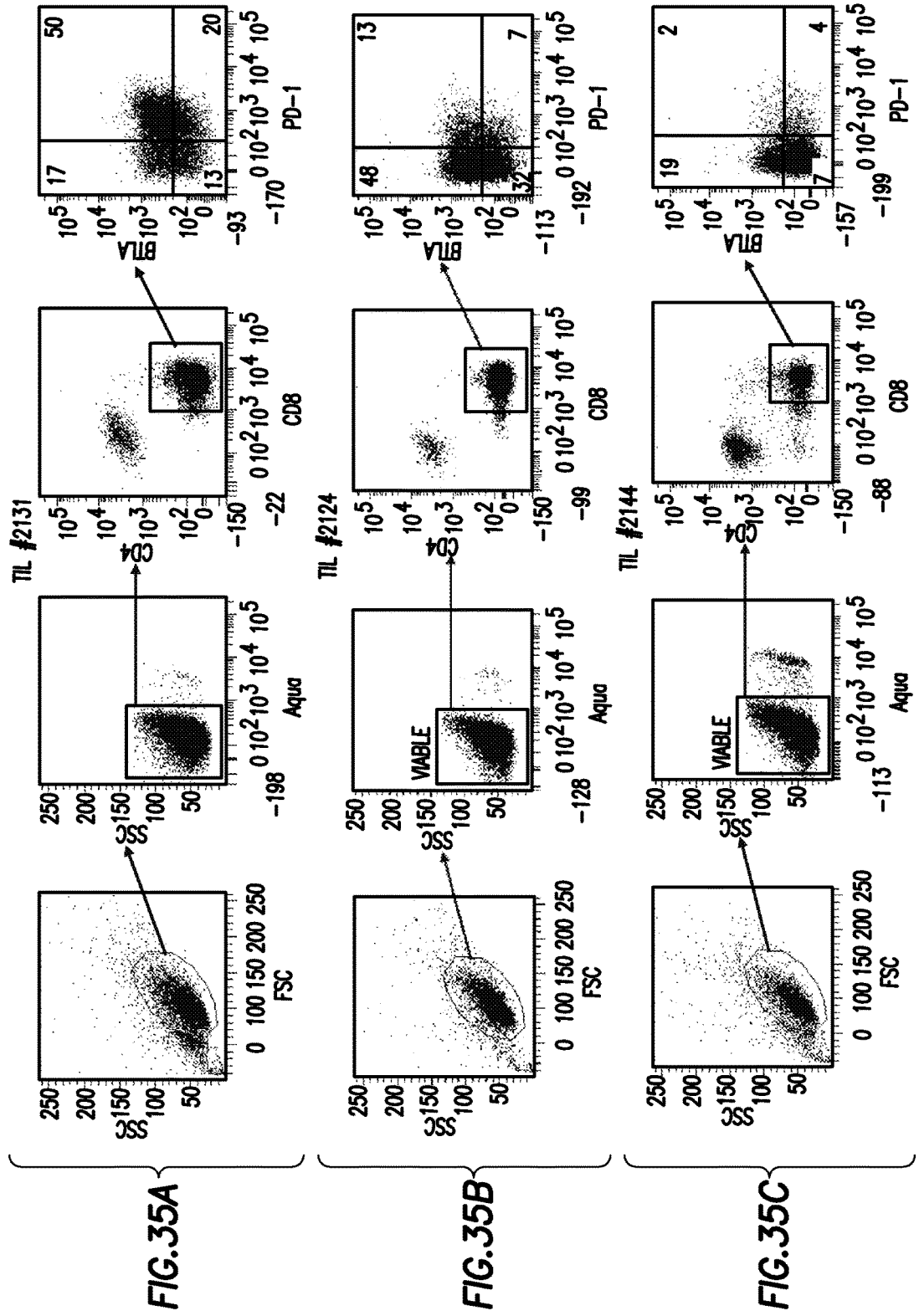

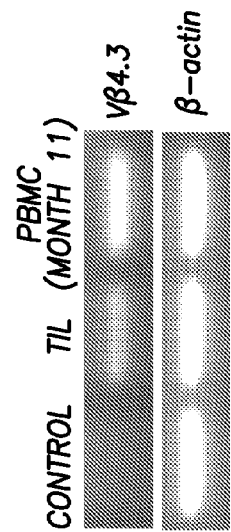
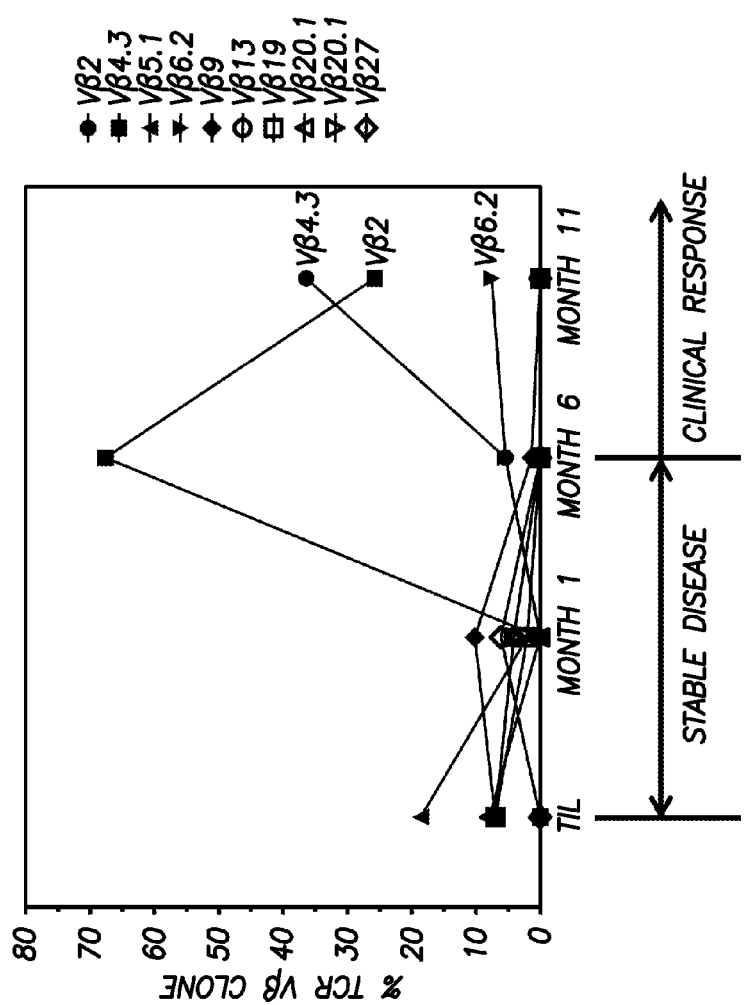
FIG. 36D
FIG. 36C

FIG.39A

RESPONDERS (n=15)

| PATIENTS | REACTIVITY |
|---|---|
| 2131 | Y |
| 2173 | Y |
| 2150/2153 | Y |
| 2124 | N |
| 2180 | N |
| 2215 | N |
| 2267 | Y |
| 2262 | Y |
| 2258 | Y |
| 2054/2256 | N |
| 2261 | Y |
| 2357 | Y |
| 2340 | Y |
| 2350 | Y |
| 2379 | Y |

11/15 (73%) REACTIVE
4/15 (27%) NON-REACTIVE

NON-RESPONDERS (n=16)

| PATIENTS | REACTIVITY |
|---|---|
| 2044 | Y |
| 2125 | N |
| 2132 | Y |
| 2114 | N |
| 2104 | Y |
| 2146 | N |
| 2136 | Y |
| 2175 | N |
| 2144 | N |
| 2247 | Y |
| 2281 | Y |
| 2245 | N |
| 2338 | Y |
| 2284 | Y |
| 2373 | Y |
| 2299 | N |

9/16 (56%) REACTIVE
7/16 (44%) NON-REACTIVE

FIG.39B

RESPONDERS (n=9)

| PATIENTS | REACTIVITY |
|---|---|
| 2131 | Y |
| 2173 | Y |
| 2150/2153 | Y |
| 2258 | Y |
| 2054/2256 | N |
| 2261 | Y |
| 2340 | Y |
| 2350 | Y |
| 2379 | Y |

8/9 (89%) REACTIVE
1/9 (11%) NON-REACTIVE

NON-RESPONDERS (n=8)

| PATIENTS | REACTIVITY |
|---|---|
| 2044 | Y |
| 2132 | Y |
| 2136 | Y |
| 2144 | N |
| 2281 | Y |
| 2338 | Y |
| 2284 | Y |
| 2373 | Y |

7/8 (88%) REACTIVE
1/7 (12%) NON-REACTIVE

B AND T LYMPHOCYTE ATTENUATOR MARKER FOR USE IN ADOPTIVE T-CELL THERAPY

CROSS-REFERENCE TO RELATED APPLICATION

This application claims the benefit of and priority in U.S. Patent Application Ser. No. 61/389,127 filed on Oct. 1, 2010. The application is herein incorporated by reference.

STATEMENT REGARDING FEDERALLY SPONSORED RESEARCH OR DEVELOPMENT

This invention was made with government support under 5RO1 CA111999-05 A2 awarded by the National Institutes of Health. The government has certain rights in the invention.

FIELD OF INVENTION

This invention relates generally to adoptive T-cell therapy ("ACT") using tumor-infiltrating lymphocytes ("TIL"), and more specifically to a new marker useful to determine which patient is more likely to respond to the therapy and to select and/or isolate the TIL having enhanced clinical activity for adoptive T cell transfer in patients by antibody-based selection or otherwise.

THE NAMES OF THE PARTIES TO A JOINT RESEARCH AGREEMENT

None.

REFERENCE TO SEQUENCE LISTING BACKGROUND OF THE INVENTION

None.

BACKGROUND OF THE INVENTION

Adoptive T-cell therapy ("ACT") used to treat melanoma has progressively grown throughout the years, expanding from mice models to current clinical trials. Although melanoma ACT (using transferred T lymphocytes) appears to be promising in many aspects, extensive works needs to be done in order for the treatment to be more successful. One key setback is the lack of persistence of the transferred TIL together with the loss of key co-stimulatory signals and telomeric repeats at the ends of chromosomes in TIL which have been extensively expanded ex vivo. A need exists therefore for a method and device to produce more potent tumor-infiltrating lymphocytes ("TIL") which have enhanced anti-tumor activity after adoptive transfer into patients.

BRIEF SUMMARY OF THE INVENTION

We have discovered that BTLA-positive ("BTLA-1-") lymphocyte signaling drives T cells and kills tumors. BTLA functions as a positive modulator of anti-tumor (anti-melanoma) T cell responses. BTLA+ T cells respond against tumor or cancer cells. We further discovered that BTLA-positive T cells ("TIL") in cancer patients respond better to IL-2 than BTLA-negative cells. Likewise, we have found BTLA-positive T-cells in cancers such as melanoma, and other cancer types including breast cancer, prostate cancer, lung, ovarian, colon can act as a positive marker for selection of enriched anti-tumor-cancer reactive T cells and can be used or applied for adoptive T-cell therapy or for therapeutic purposes. Moreover, agonistic anti-BTLA antibodies or BTLA ligands can be used to positively drive anti-tumor or anti-cancer T cell responses. Antibodies specific for BTLA can be used to select more highly cancer-reactive T cells for therapeutic purposes.

BRIEF DESCRIPTION OF THE DRAWINGS

FIGS. 1A, 1B, and 1C show the presence of tumor-reactive T-cells in metastatic melanomas.

FIGS. 6A and 6B show that more TCR clones persist in responders than in non-responders.

FIG. 11 shows the results of the analysis of CD8+ T-cell differentiation status in infused TIL.

FIG. 13 shows the distribution of different CD8+ T-cell differentiation states in TIL of all treated patients.

FIG. 14 shows that a more differentiated effector phenotype correlates best with positive clinical response.

FIGS. 15A through 15C show PD-1 and BTLA expression on CD8+ TIL.

FIGS. 18A through F show that melanoma, antigen-specific CD8+ TIL are highly enriched for BTLA+ cells.

FIGS. 19A and 19B show that there is high HVEM expression on melanoma cells and BTLA down-modulation on TIL.

FIGS. 20A and 20B show a loss of telomeres during ex vivo expansion of melanoma TIL for ACT.

FIGS. 26A through 26D show the recovery of total white blood cell counts (WBC), absolute lymphocyte counts (ALC), and absolute neutrophil counts (ANC) during adoptive transfer TIL therapy in 31 treated patients.

FIGS. 27A through 27J show objective tumor regression in patients receiving autologous TIL therapy.

FIGS. 31A through 31F show the comparison of total cells infused and major T-cell subsets in the infused TIL product between responders ("CR/PR") and non-responders ("PD/SD").

FIGS. 34A through 34H show the Expression of PD-1, BTLA, and TIM-3 negative costimulatoly markers on $CD8^+$ TIL and correlation to the type of clinical response to TIL therapy.

FIGS. 35A through 35C show co-expression of BTLA and PD-1 on $CD8^+$ T cells in melanoma TIL.

FIGS. 36A through 36D show tracking of changes in the frequencies of major TCR Vβ clonotypes in the infused TIL and peripheral blood after TIL infusion.

FIG. 39 shows a comparison of TIL anti-tumor reactivity versus melanoma cell lines and clinical response as discussed in Example II below.

DETAILED DESCRIPTION OF THE INVENTION

Figure 2:
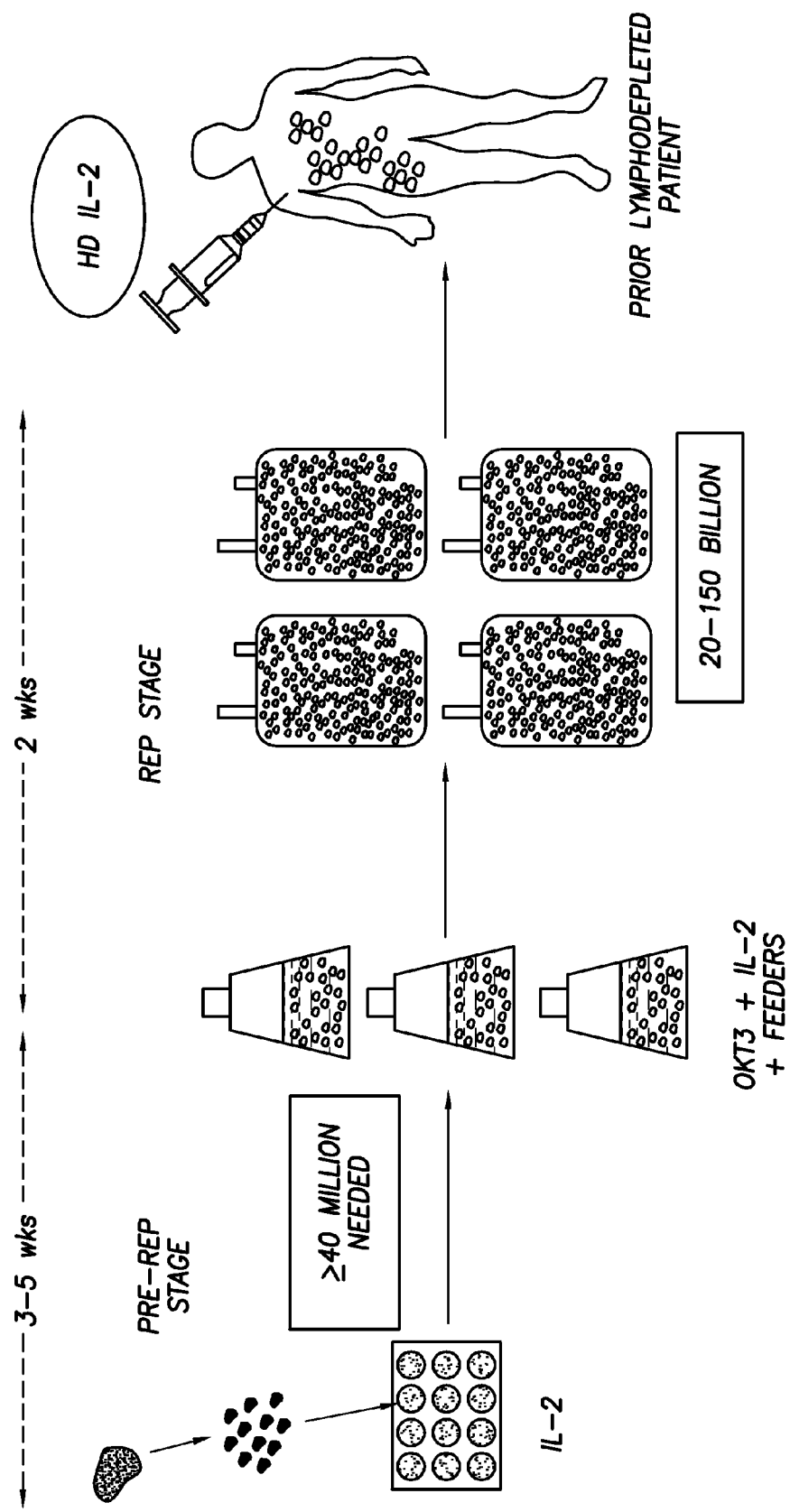
FIG. 2 illustrates the process of adoptive T cells therapy using ex vivo expanded melanoma TIL.
Figure 3:
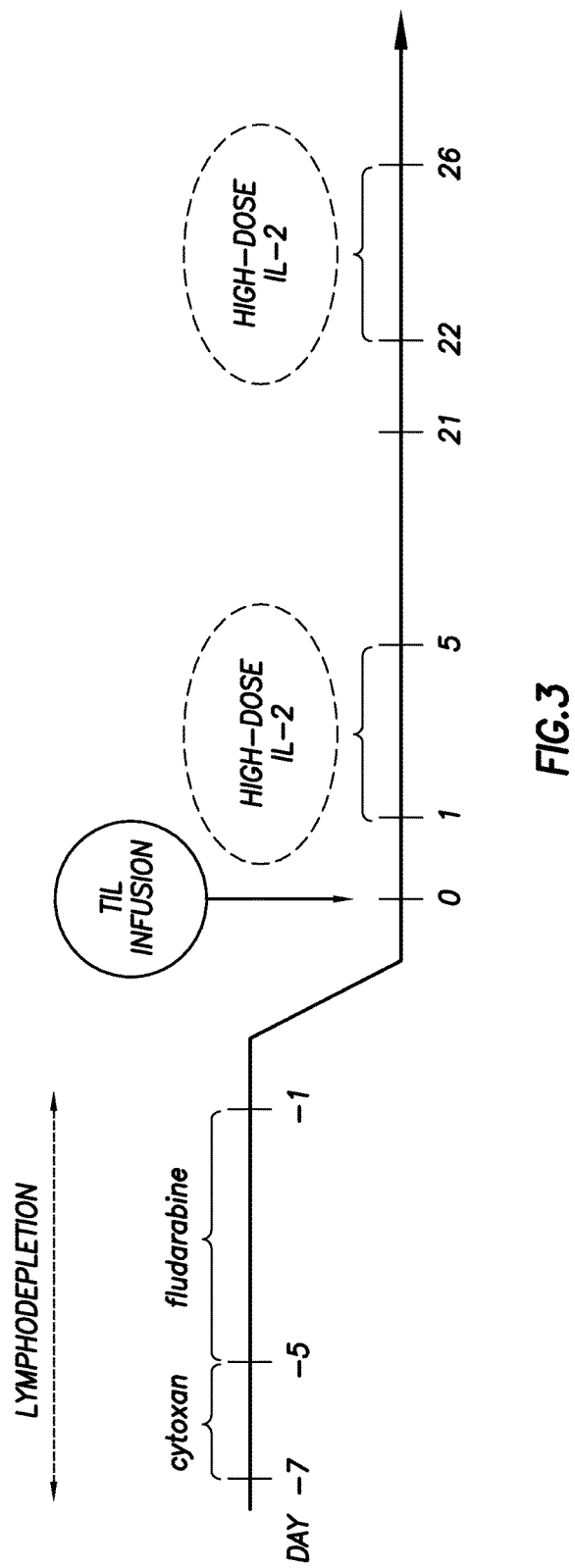
FIG. 3 illustrates the treatment timeline of adoptive T cells therapy using ex vivo expanded melanoma TIL.
Figure 4:
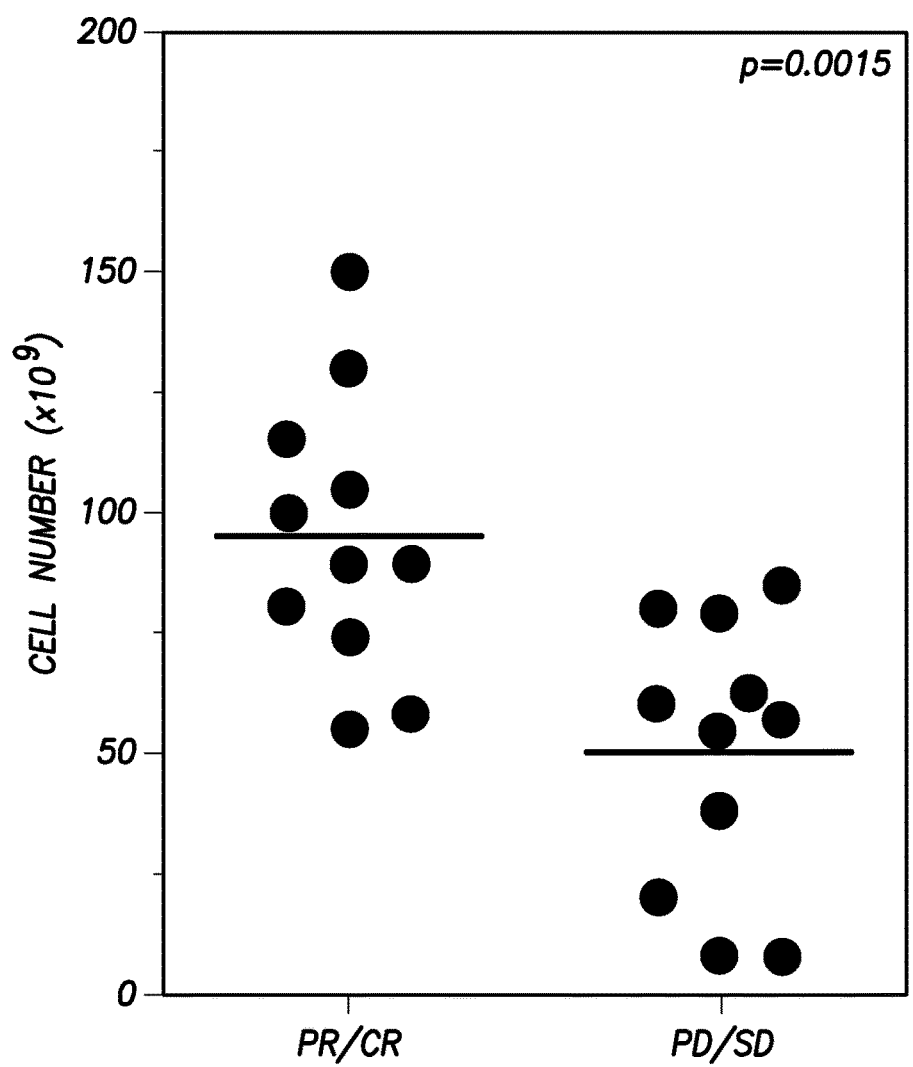
FIG. 4 shows the numbers of total TIL infused and the type of clinical response.
Figure 5B:
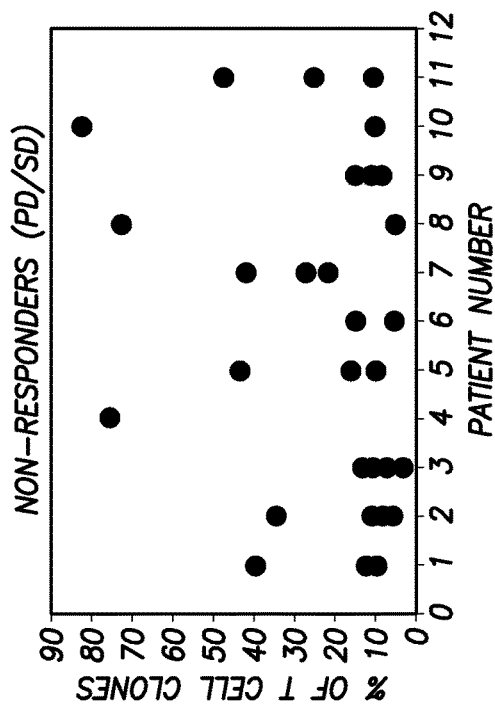
FIGS. 5A through 5D show the number and persistence of dominant clones.
Figure 5A:
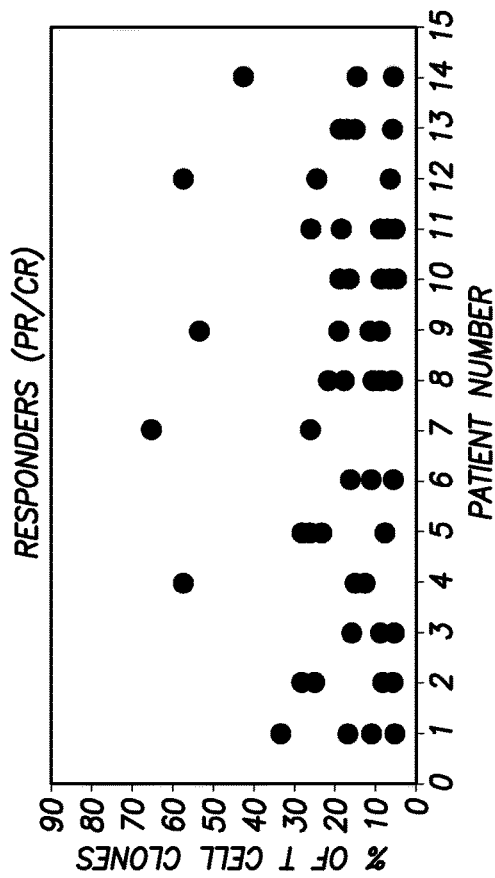
Figure 5D:
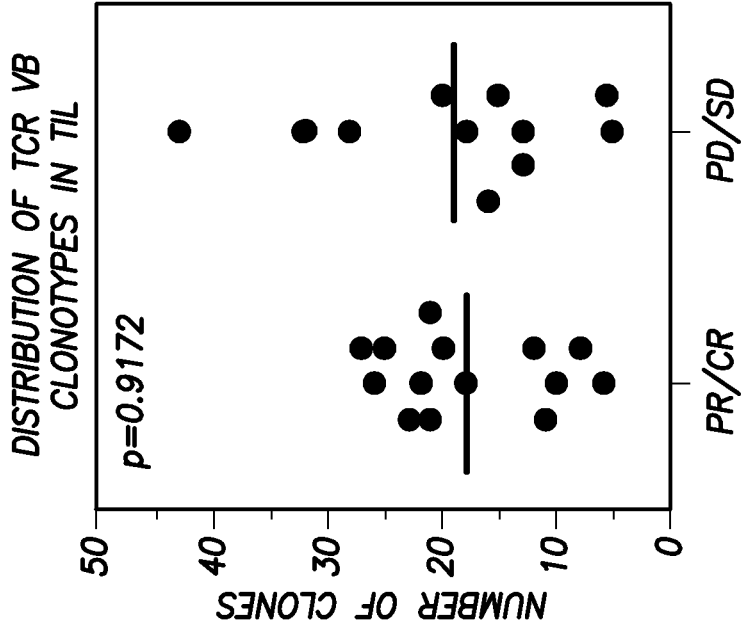
Figure 5C:
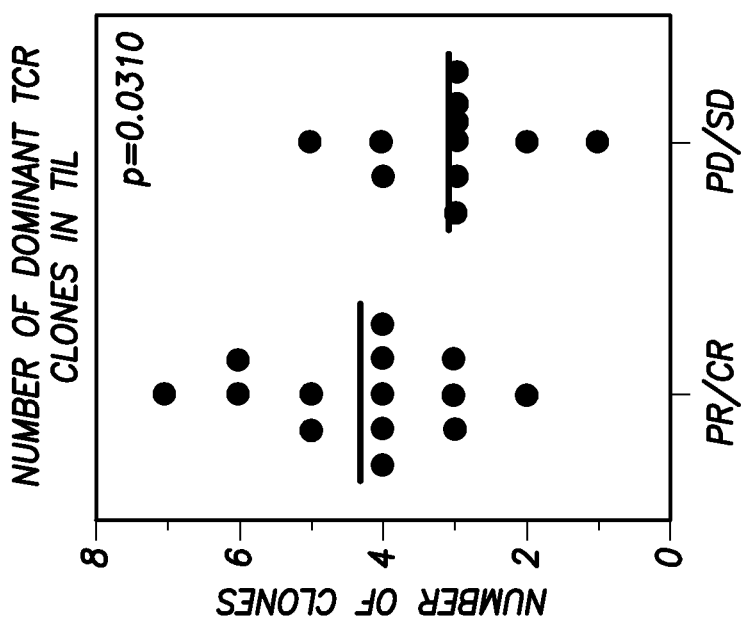
Figure 7A:
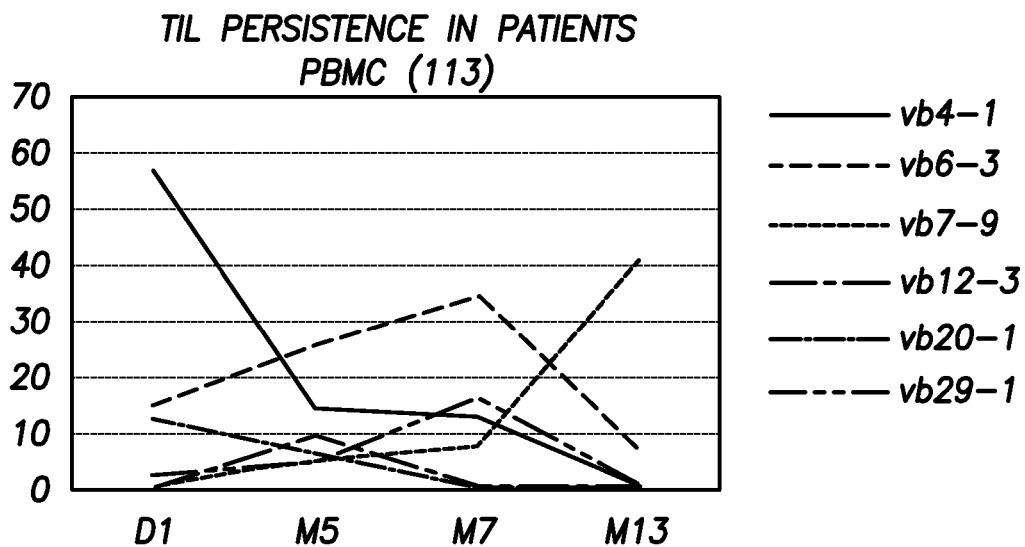
FIGS. 7A through 7F show that long-term persistence of dominant clones correlates with clinical response.
Figure 7D:
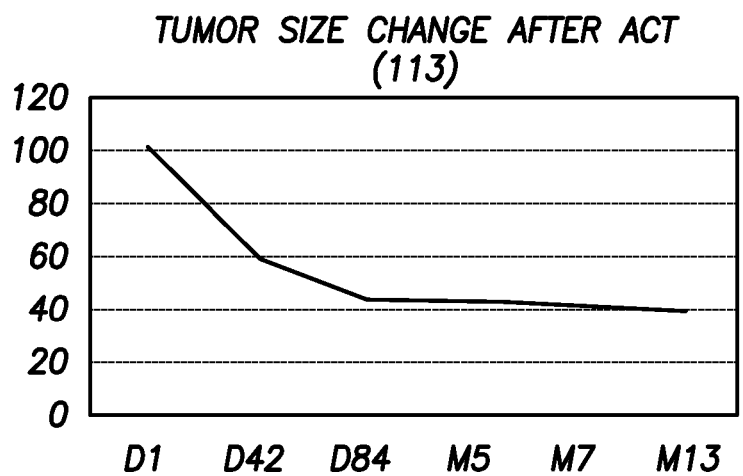
Figure 7B:
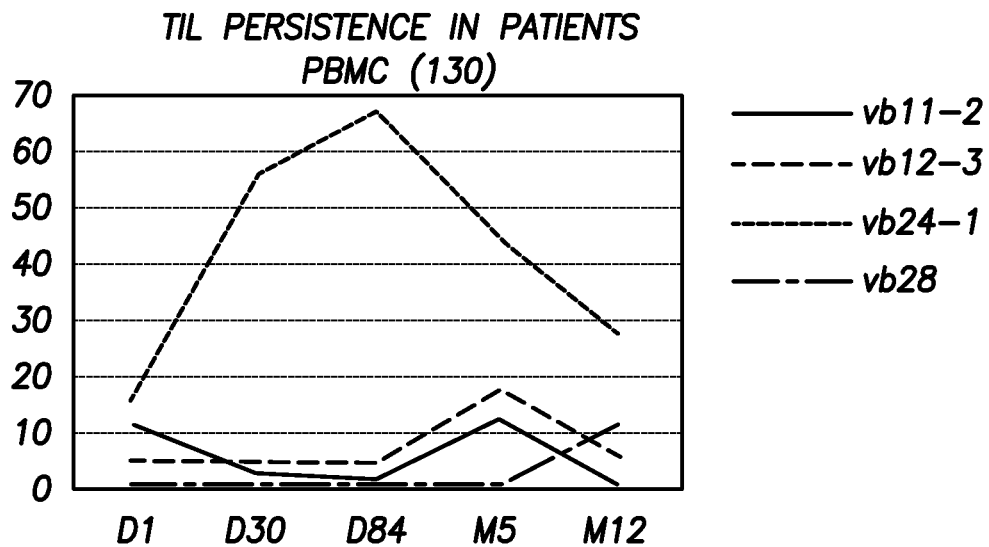
Figure 7E:
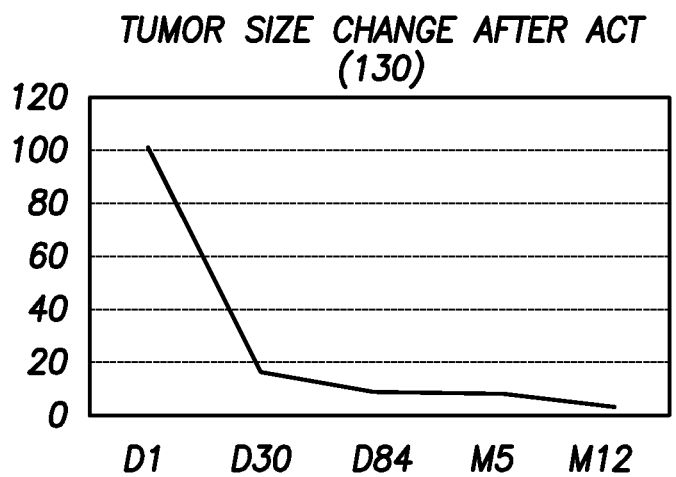
Figure 7C:
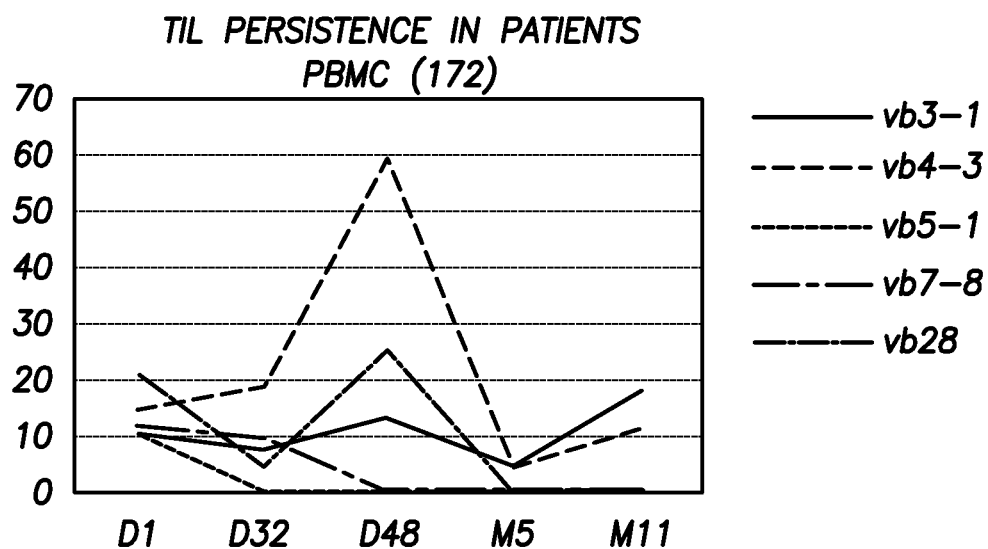
Figure 7F:
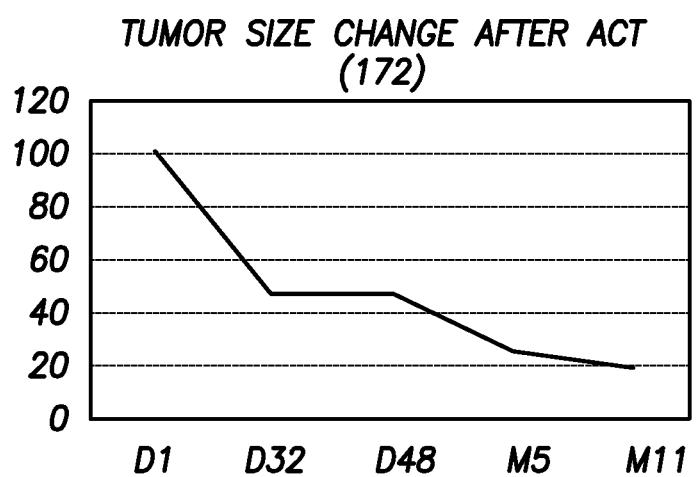
Figure 8A:
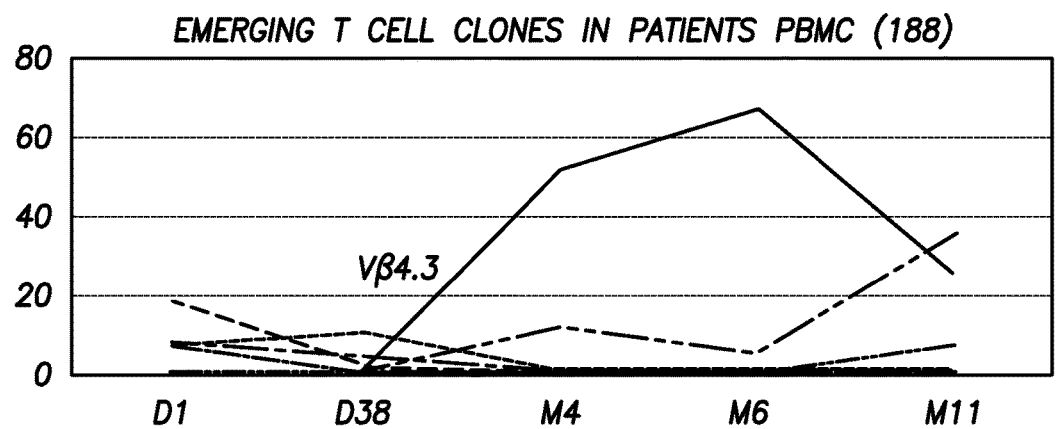
FIGS. 8A through 8D show that emerging T cell clones may contribute to delayed clinical responses (>3 months).
Figure 8C:
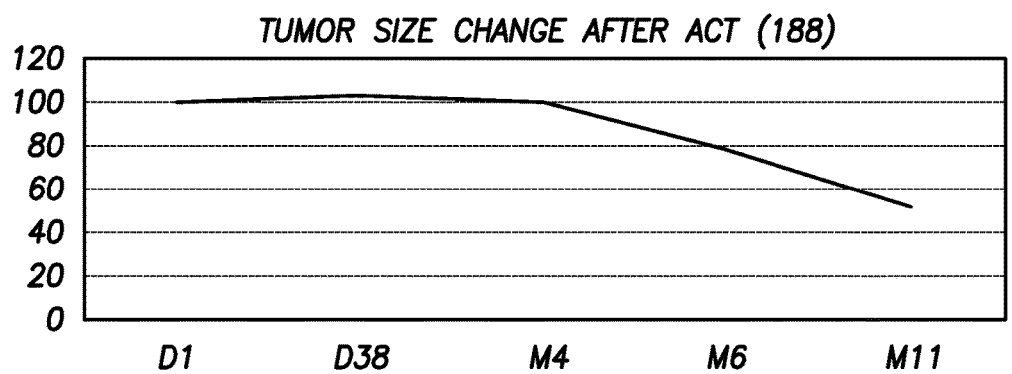
Figure 8B:
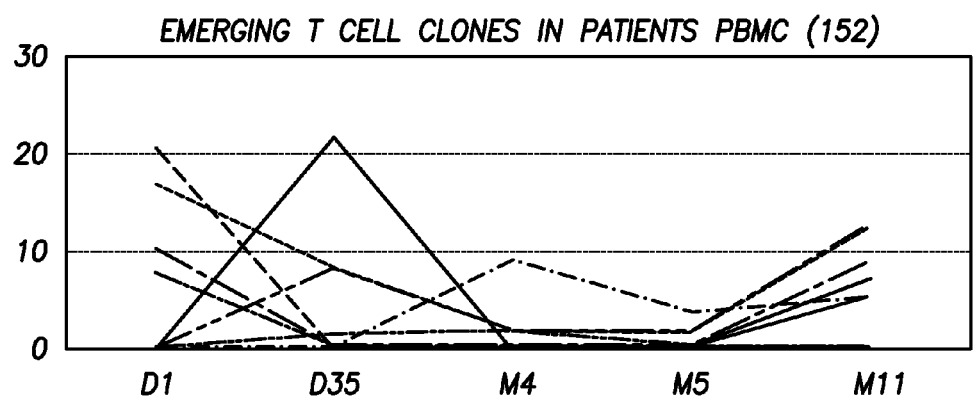
Figure 8D:
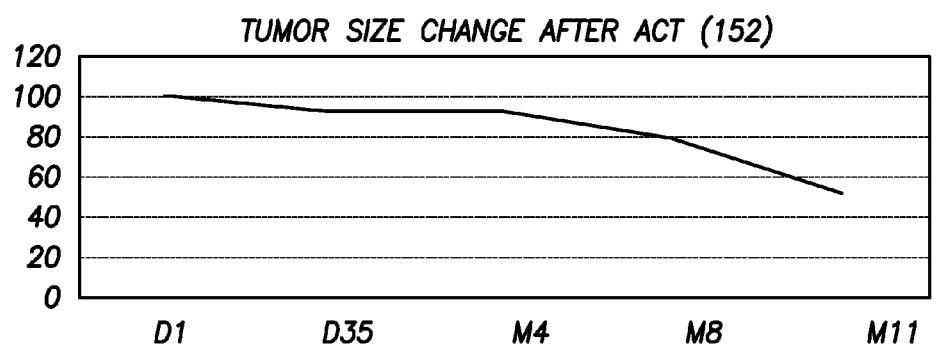
Figure 9B:
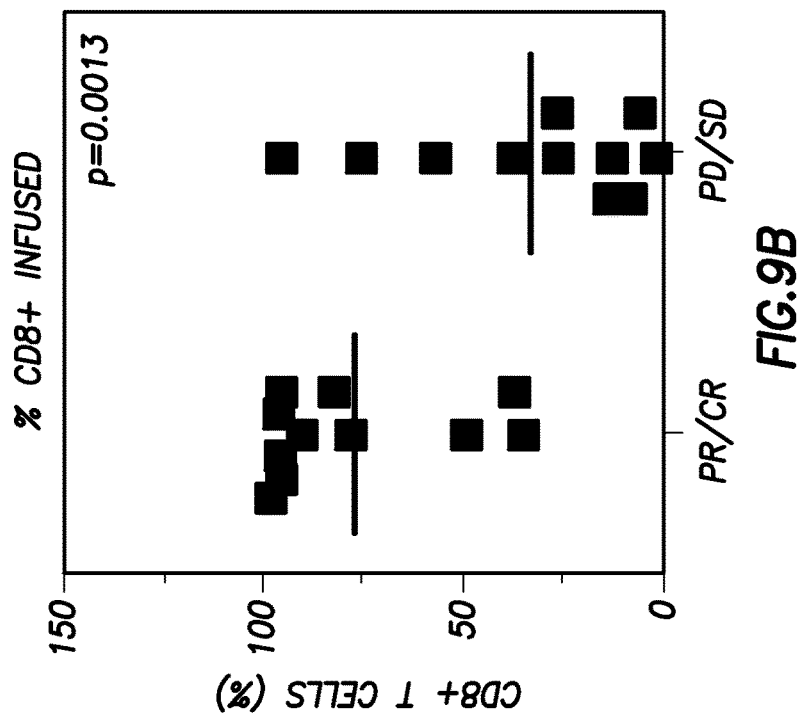
FIGS. 9A through 9D show that CD8+ TIL are critical in achieving a clinical response.
Figure 9A:
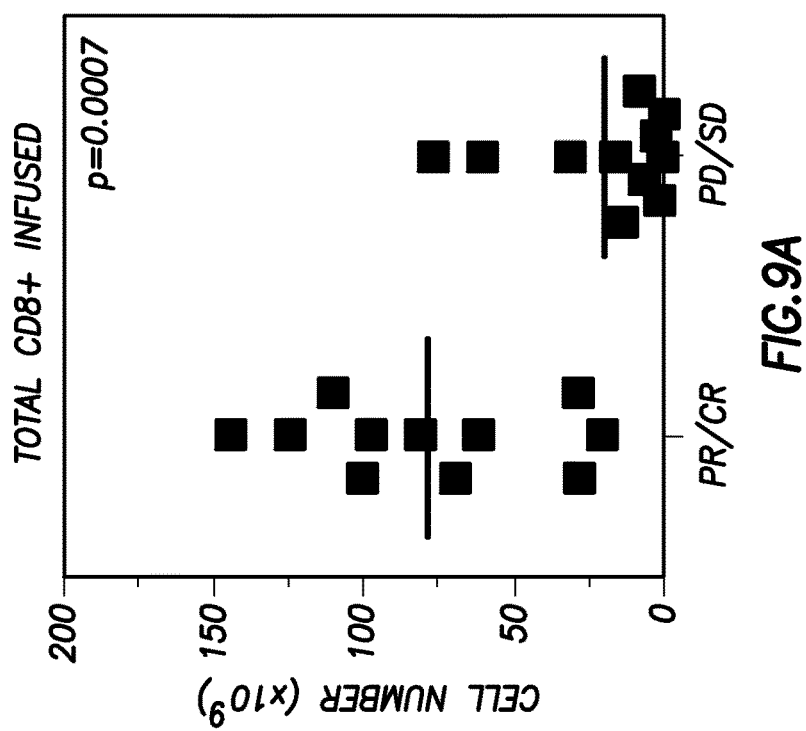
Figure 9D:
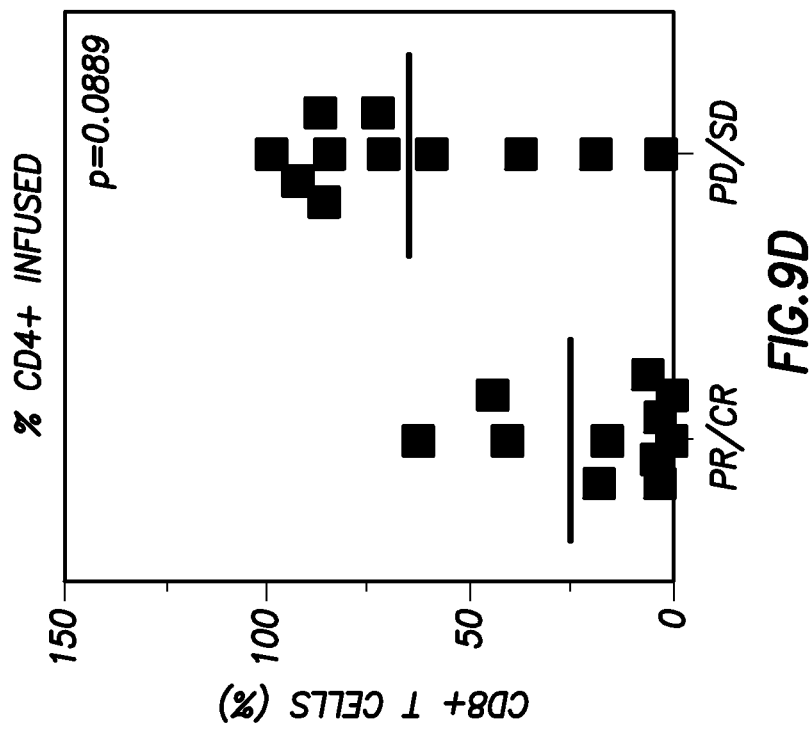
Figure 9C:
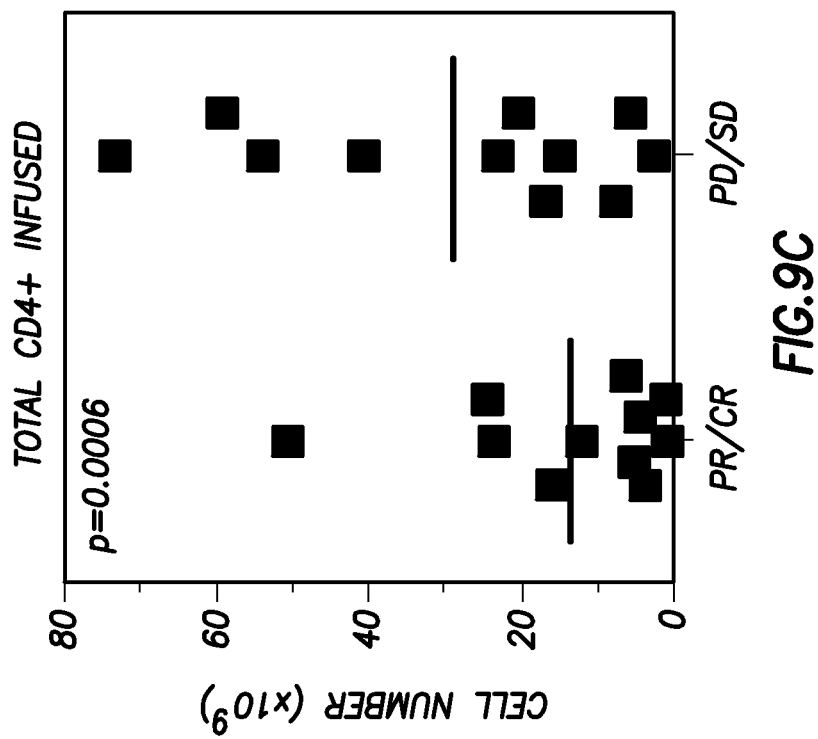
Figure 10:
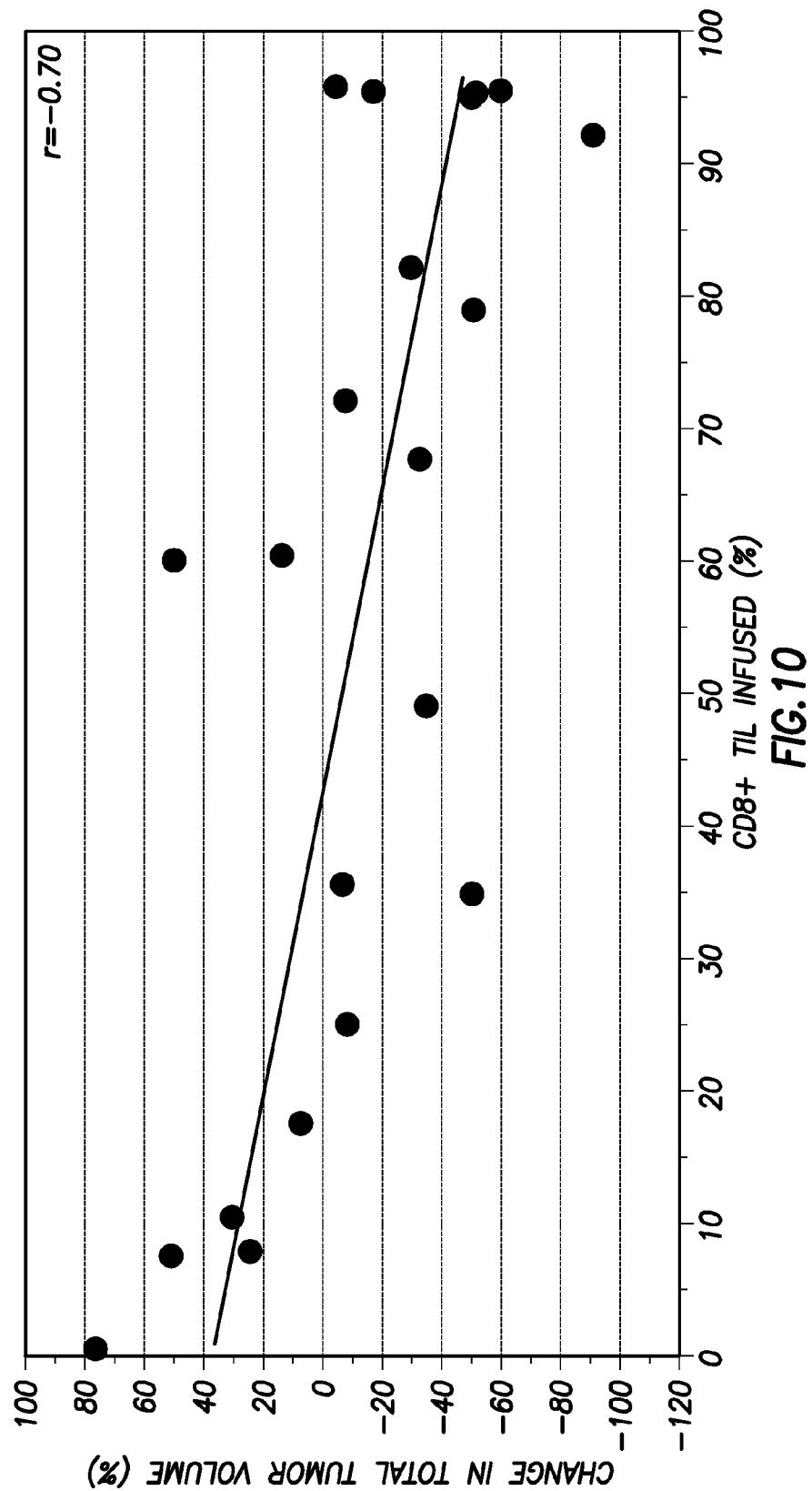
FIG. 10 shows that the percentage of CD8+ T cells infused correlates with degree of tumor shrinkage (n=22).
Figure 12:
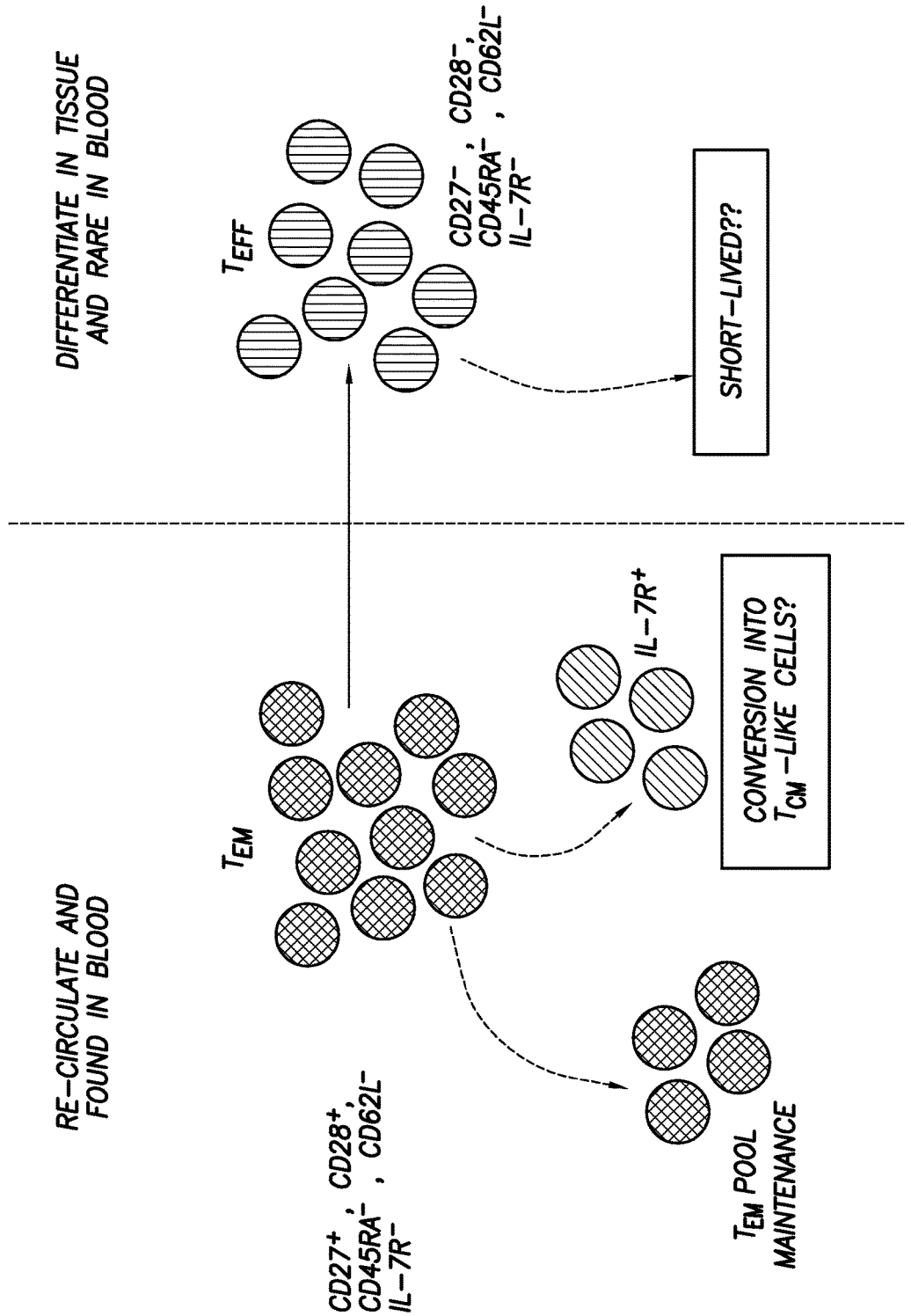
FIG. 12 illustrates the roles of $T_{EM}$ and $T_{EFF}$ cells in ACT.
Figures 16A, 16B:
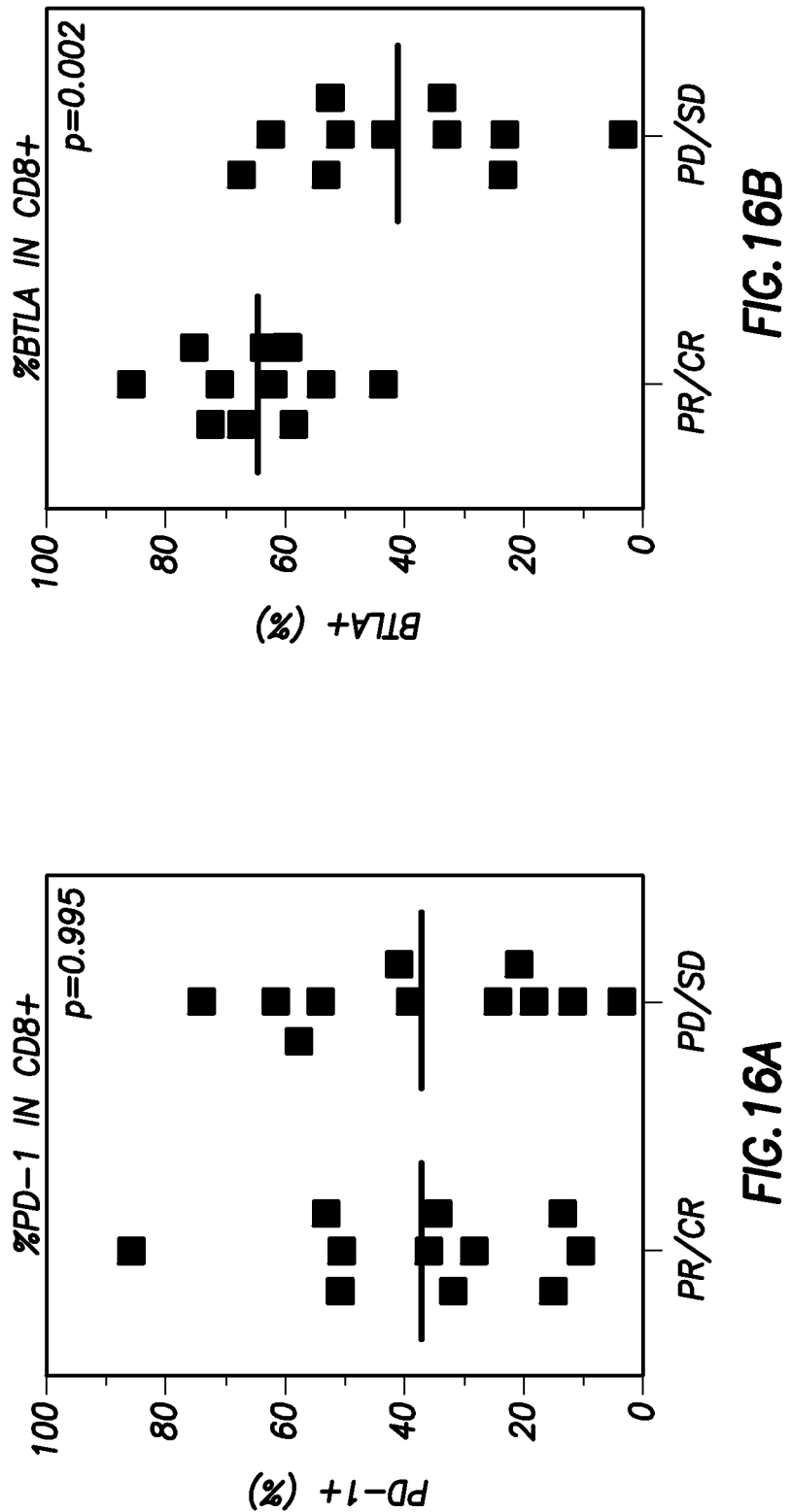
FIGS. 16A and 16B show that BTLA has a better correlation with the type of response (PR/CR or PD/SD) than PD-1.
Figure 17A:
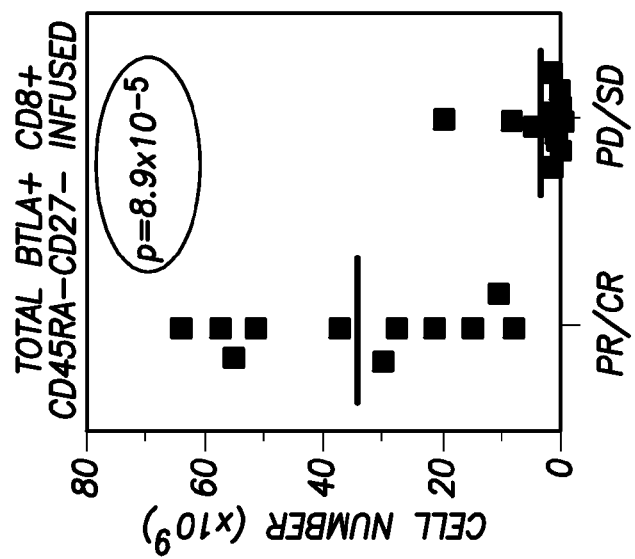
FIGS. 17A through 17C show that BTLA has a better correlation with the type of response than PD-1.
Figure 17B:
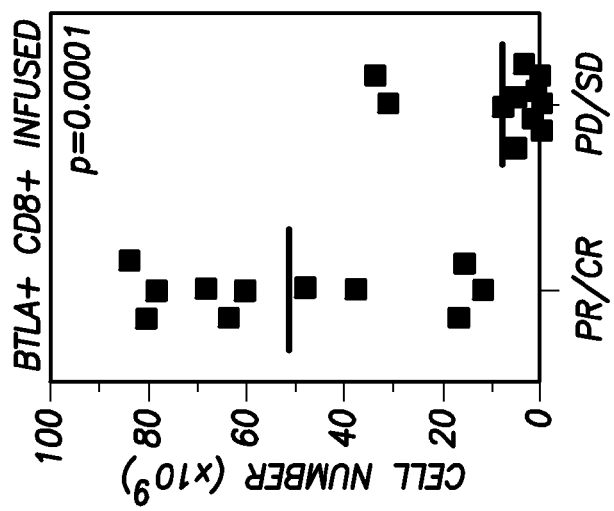
Figure 17C:
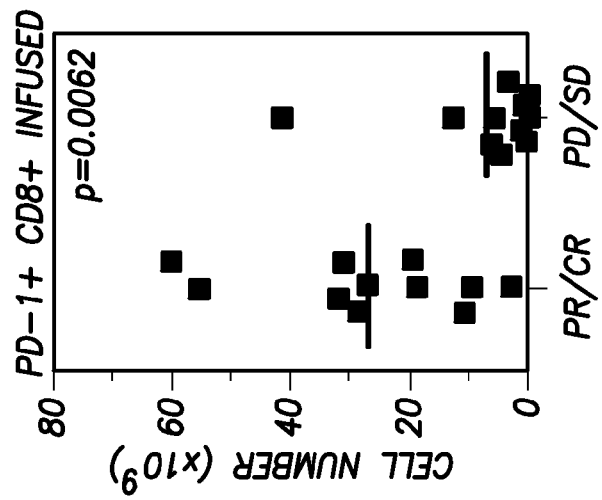
Figure 21:
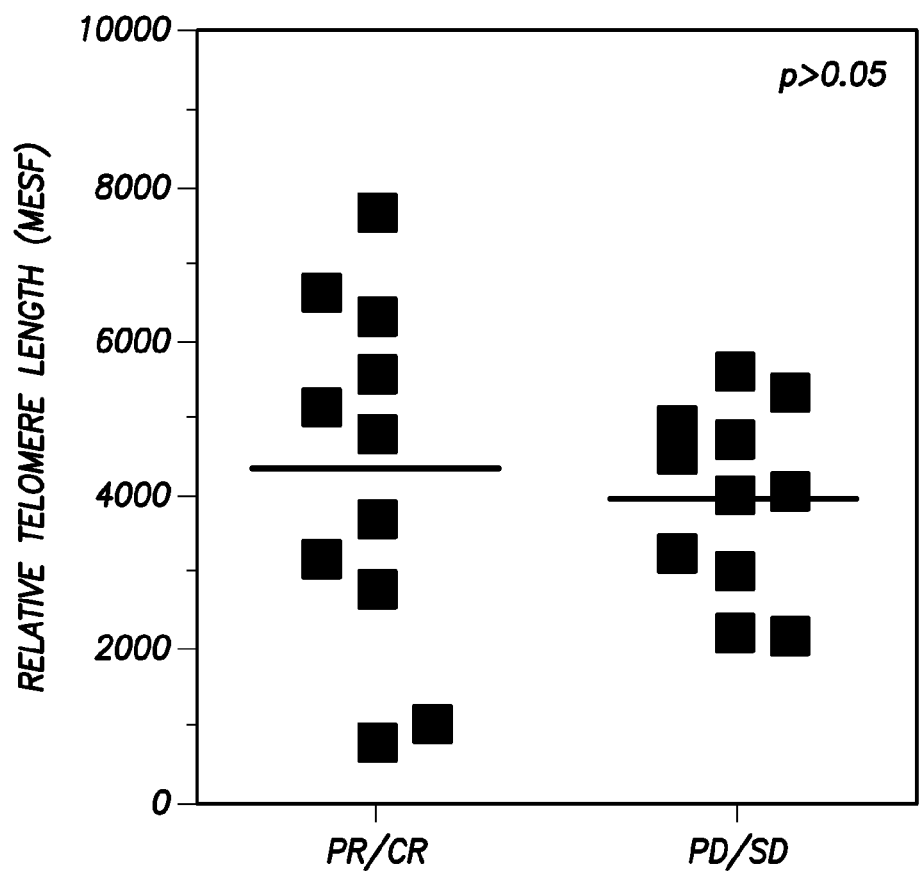
FIG. 21 shows that there is no difference in telomere length of infused TIL between responders and non-responders.
Figure 22:
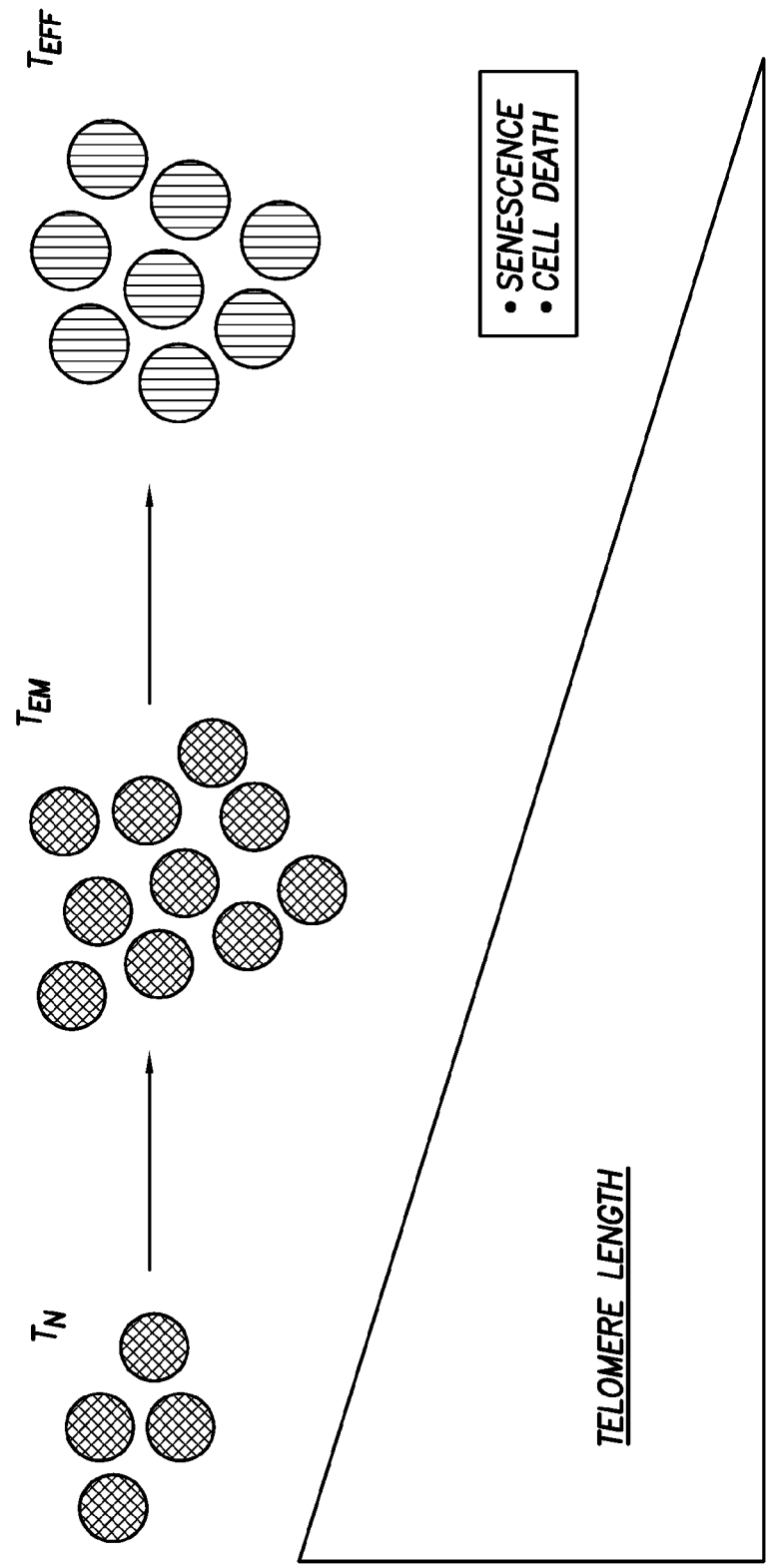
FIG. 22 is illustrative of the decrease in telomere length leading to senescence and cell death that occurs with T-cell differentiation.
Figure 23:
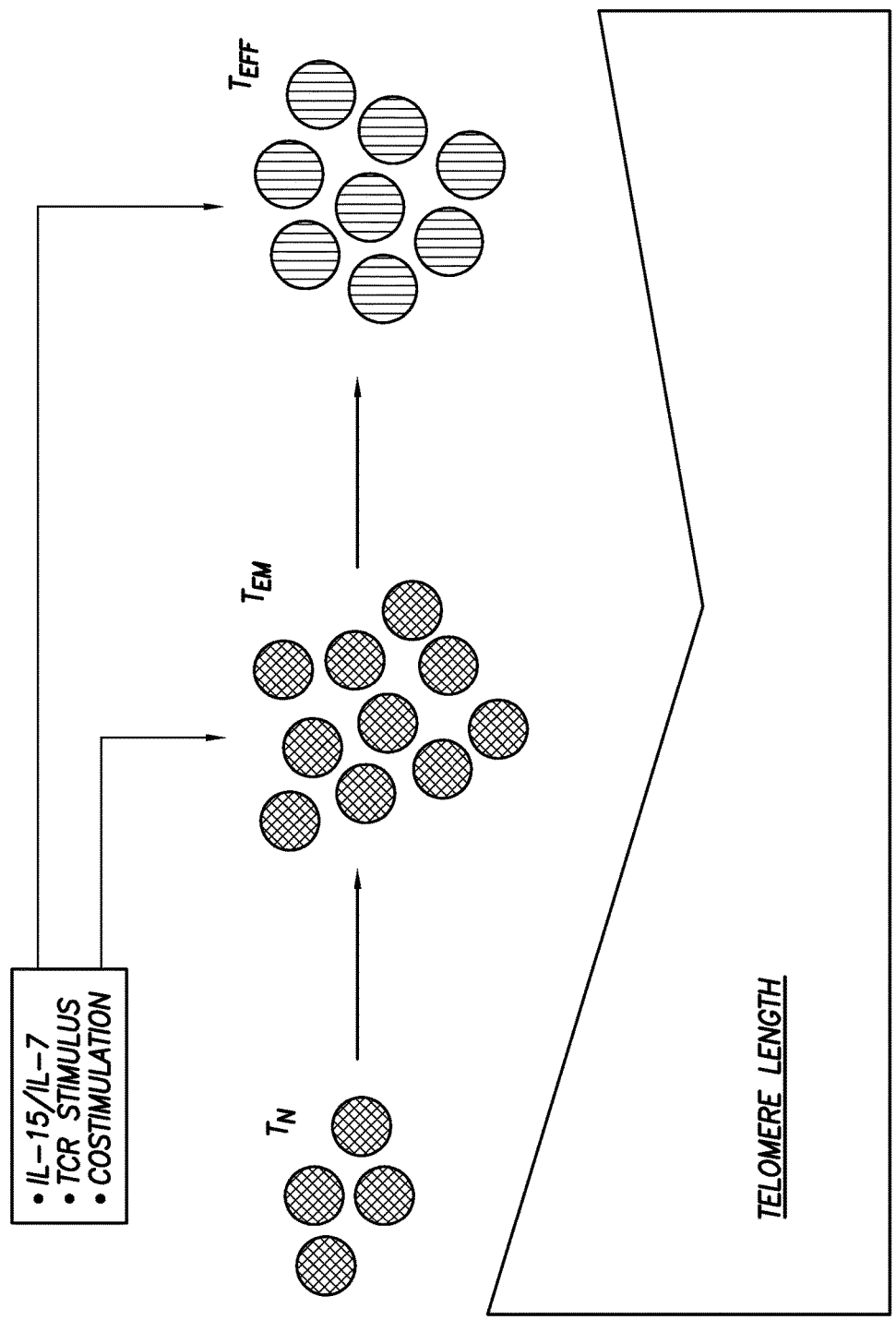
FIG. 23 is illustrative of the changes in telomere length that occurs with T-cell differentiation accompanied by IL-15/IL-7, TCR stimulation, and co-stimulation.
Figure 24:
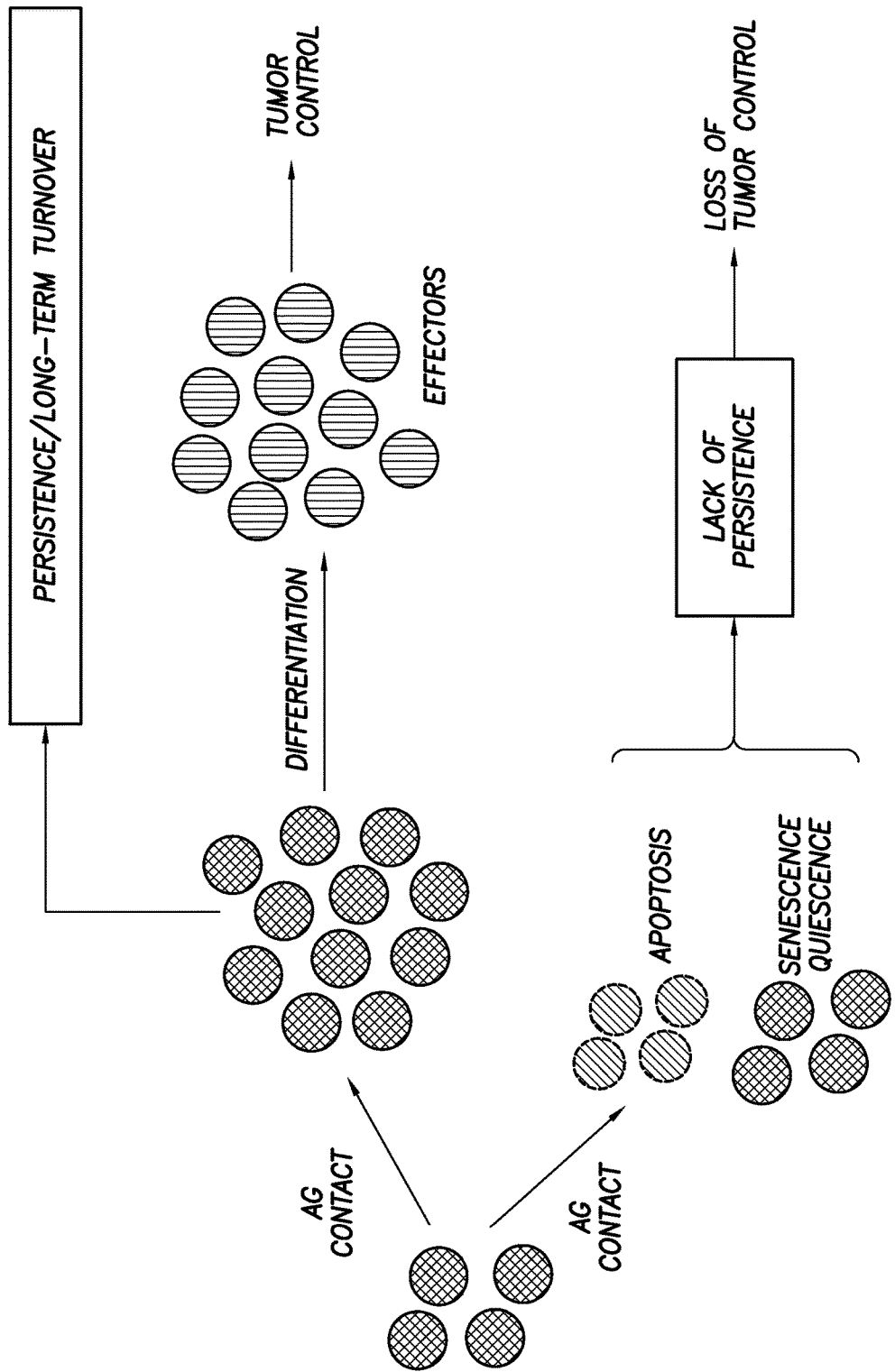
FIG. 24 shows the possible fates of adoptively-transferred TIL.

Metastatic melanoma is an aggressive form of cancer highly resistant to traditional forms of therapy, such as chemotherapy and radiation therapy. Response rates and survival times for patients with advanced stages (IIIc and IVc) in response to chemotherapy, such as dacarbazine and temozolomide, have been relatively poor. Due to its relative refractoriness to chemotherapy and radiation therapy, melanoma has been widely studied as a target for immunotherapy. In addition, most melanoma metastases contain lymphocytic infiltrates and T cells recognizing major melanoma antigens, such as Melan-A/MART-1 and in some cases, gp100, and can be readily detected in many tumors.

Capitalizing on these observations, cytokine therapies, such as IL-2, were introduced to boost T-cell and NK cell activation in patients. Although the overall response rate to high dose IL-2 in patients with metastatic melanoma is low, a small percentage of patients have durable complete responses, and this treatment has been considered a (proof-of-concept that immune activation can indeed induce durable long-term remissions, while others therapies have failed. Thus, further enhancing these immunological mechanisms is a high priority.

Adoptive cell therapy ("ACT") using tumor-infiltrating lymphocytes ("TIL") expanded ex vivo together with HD IL-2 therapy has been one of the major approaches to improve upon the response rates with IL-2. Combining a preparative lymphodepleting chemotherapy regimen using cyclophosphamide and fludarabine in melanoma patients prior to infusing the TIL and HD IL-2 regimen facilitates the clonal repopulation of the TIL in vivo and improved the clinical response rate. The TIL shows a better persistence with lymphodepletion prior to infusion. As such, the lymphodepletion regimen prior to adoptive transfer of T cells has become an essential component of ACT because it eliminates lymphocytes that would compete with the infused TIL for homeostatic cytokines, such as interleukin-7 (IL-7) and Interleukin-15 (IL-15). Lymphodepletion also eliminates endogenous $CD4^+Foxp3^+$ T regulatory cells (Tregs) that can inhibit effector T-cell function and the continued proliferation of infused TIL in vivo after adoptive transfer.

ACT involves the isolation of viable tumor tissue and the expansion of TIL with IL-2 over 4-5 weeks from tumor fragments placed in culture, TIL are then further expanded in larger-scale using anti-CD3 activation and exogenous IL-2 in the presence of autologous or allogeneic irradiated feeder cells. This protocol has become known as the "rapid expansion protocol" (REP) and can yield as much as 100-1.50 billion cells for infusion. Durable responses to TIL therapy were improved by the addition of a preparative lymphodepleting regimen using a combination of cyclophosphamide and fludarabine (ref). Indeed, lymphodepleting regimen prior to cell transfer resulted in an increase in persistence of the transferred cells, which in turn correlated with better clinical outcome.

The extensive expansion of TIL in vitro leading to telomere shortening may be a negative factor in ACT. Longer telomere length of the infused TIL product have been reported to correlate with objective clinical responses in melanoma ACT; however additional clinical trials will confirm this hypothesis. This could be particularly relevant due to the possibility of telomerase activation in T cells that can occur after TCR stimulation with co-stimulatory molecules such as 4-1BB and CD28.

Overall, knowing the nature of T cells mediating objective anti-tumor responses during ACT allows selection of the most active cell subsets to transfer into patients and/or how to tailor TIL expansion procedures to preferentially expand these active T-cell populations for therapy to improve clinical response rates.

In a preliminary analysis of 25 treated metastatic melanoma patients (discussed in Example I below) at M.D. Anderson Cancer Center, we have found a strong correlation between patients undergoing a clinical response (partial or complete response) and the increased expression of a co-stimulatory molecule called "B and T lymphocyte attenuator" ("BTLA") on the CD8+ T cells in the infused TIL product. Patients undergoing a clinical response had a significantly higher percentage of BTLA-F-CD8+ TIL infused ($p<0.01$), and this association between clinical response became even more significant when the BTLA marker on CD8+ TIL was combined with other markers such as gp100, MART-1, or tyrosinase using peptide pulsed autologous mature dendritic cells which indicate an enhanced state of cytotoxic T-cell differentiation (CD45RA−, CD27−, and CD28−) in the infused TIL cells. Additional data has found that a higher proportion of melanoma antigen-specific CD8+ TIL (MART-1 and gp100 specific cells) express BTLA than nonspecific T cells. Moreover, we have found that BTLA+ TIL proliferate more vigorously than BTLA− TIL after purification using fluorescence-activated cell sorting (FACS).

Hence, BTLA expression is a marker for more potent TIL possessing enhanced anti-tumor activity after adoptive transfer into patients and BTLA can be used as a selective marker for these cells to generate BTLA-enriched TIL products for ACT. Manipulation of BTLA signaling in melanoma TIL can greatly enhance anti-tumor effector activity during ACT using either an agonistic (activating) or a blocking antibody that can be used either during TIL expansion ex vivo to improve the cell product, or after TIL infusion in patients as an method to boost TIL anti-tumor activity in vivo.

Hence, described herein is the use of BTLA-positive ("BTLA+") T cells as a biomarker for tumor infiltrating lymphocytes (TIL) which mediate clinical responses in Adoptive T-Cell Therapy ("ACT") in cancer patients, particularly melanoma patients. This marker may be used in ACT for other cancers, such as lymphoma and other solid tumors. This marker can also be used to select or purify T cells found in the blood or TIL with better anti-tumor activity properties for ACT applications.

The BTLA-positive T cell marker is also sometimes referred to herein as BTLA+, BTLA marker, BTLA positive marker, BTLA-positive marker, BTLA positive, BTLA+ CD8+ T cell BTLA+CD8+ TIL, BTLA+ T cell, BTLA positive T cell, BTLA+TIL, BTLA positive TIL, BTLA tumor antigen-specific T cell, and/or BTLA-positive TIL. The marker may be referred to in the singular (T cell) or plural (I cells), BTLA-positive T cells allow selection of expanded TIL having optimal anti-tumor activity for ACT in the clinic by selecting specifically expanded BTLA+CD8+ T cells for adoptive transfer into patients, rather than a bulk TIL population with mixed activity that would be suboptimal. The BTLA+ CD8+ TIL can be selected at different stages of the ex vivo TIL expansion process for ACT, namely, during initial expansion out of cultured tumor fragments, or during large-scale rapid expansion used to generate the final TIL infusion product.

For example, before the rapid expansion protocol (REP) BTLA+TIL can be positively selected using antibody-coated beads or using clinical Fluorescence Activated Cell Sorter (FACS), resulting in a highly pure BTLA+ expanded TIL population for adoptive transfer into patients that will have optimal proliferative and effector functions in vivo and an improvement in the efficacy of ACT. Hence, also provided herein is a new CD8+BTLA+TIL selection protocol and other clinical-grade cell selection processes.

EXAMPLE I

Adoptive T-cell therapy ("ACT" and sometimes referred to herein in as "adoptive cell therapy") using autologous tumor-infiltrating lymphocytes ("TIL") is a promising treatment for metastatic melanoma unresponsive to conventional therapies. The preliminary results of a Phase II clinical trial testing the efficacy of ACT in metastatic melanoma patients regardless of HLA subtype is reported in this example. The preliminary analysis was concluded in October of 2010 and the data associated with this study is provided in FIGS. 1 to 24.

Autologous TIL, initially grown from tumor fragments, were expanded in large-scale under GMP conditions using anti-CD3 and IL-2 and then infused into patients following transient lymphodepletion. This was followed by high-dose IL-2 therapy.

The best overall response was determined using the "immune-related response criteria" of Wolchok et al. (*Clin. Can. Res.* 2009, 15: 7412-7420). This was correlated with T-cell phenotype and differentiation status as well as telomere length. The persistence of specific TCR clonotypes after infusion was also tracked and correlated to clinical response.

Altogether, 30 patients were treated with expanded TIL ranging from 8-150 billion cells with clinical response data available from 25 patients (as of Jun. 20, 2010). Overall, 13/25 (52%) patients have had a clinical response (PR/CR), with one patient exhibiting an ongoing PR for over 22 months and another patient having a CR. A higher percentage and number of CD8+ T cells ($P<0.05$) and a lower percentage of CD4+ T cells ($P<0.05$) in the infused TIL was associated with a higher probability of clinical response. A greater decrease in size of the major recorded lesions was also significantly correlated with an increased percentage and total number of CD8+TIL infused ($P<0.05$), while an opposite trend was observed for CD4+TIL.

Phenotypic analysis using multi-color flow cytometry revealed that infused TIL of clinical responders had significantly more CD8+ T cells with a differentiated effector phenotype (CD45RA-CD27-). Unexpectedly, we found that responders also had a higher percentage of CD8+TIL expressing the negative costimulation molecule "B- and T-lymphocyte attenuator" (BTLA) and were infused with significantly higher numbers of CD8+BTLA+ T cells than non-responders ($P<0.002$). Tumor regression was also associated with the persistence of dominant TIL TCR V-beta clonotypes in vivo for at least 3 months, while expansion of subdominant TIL clonotypes after 6 months was associated with clinical response after a prolonged period of disease stabilization in some patients. No significant difference in relative telomere length of TIL between responders versus non-responders was evident.

Preliminary, the ACT trial achieved a high clinical response rate for metastatic melanoma. CD8+ T cells appear to be critical in driving tumor regression. Our results also showed that the differentiation status of TIL and specific phenotypic subsets (e.g., BTLA+) are more predictive of clinical response than relative telomere length. In addition, the finding that some patients have delayed clinical responses after a period of s disease suggests that it is critical not to perform additional therapies on patients compromising T-cell function or survival until clear evidence of disease progression was found.

Our immunophenotyping of the infused TIL products was designed to determine whether any significant differences exist between responding and non-responding (progressive disease) that would suggest a fundamentally different biology of the TIL between these two sets of patients. The analysis was performed using staining with fluorescent antibodies for cell surface and intracellular T-cell markers and revealed that CD8+ cytotoxic T lymphocytes (CTL) that were positive for the BTLA marker was associated with positive clinical response.

Positive clinical response was associated with both a higher percentage and higher numbers of CD8+BTLA+TIL infused.

Table 1 below shows the raw data of the BTLA staining results with percentage BTLA+ cells in the CD8+ TIL infused, as well as total number of CD8+BTLA+ TIL infused for the two sets of patients (responders (PR/CR) and non-responders (PD)).

TABLE 1

SUMMARY OF TIL BTLA PHENOTYPE
AND TYPE OF CLINICAL RESPONSE

| PATIENT MRN# | RESPONSE TYPE | TOTAL TIL INFUSED INFUSED (billions) | % BTLA+ IN CD8+ TIL | TOTAL CD8+BTLA+ TIL INFUSED |
|---|---|---|---|---|
| 679321 | PD | 8 | 62.4 | 0.2885376 |
| 674162 | PD | 85 | 3.53 | 0.2292382 |
| 711726 | PD | 79.8 | 50.95 | 30.84730047 |
| 675989 | PD | 54.6 | 23.91 | 7.48896221 |
| 674162 | PD | 62.5 | 67.52 | 5.38472 |
| 687927 | PD | 38 | 23.55 | 3.3433464 |
| 756171 | PD | 57 | 33.03 | 4.96847169 |
| 716172 | PD | 80 | 43.96 | 33.6276416 |
| 716237 | PD | 60 | 52.48 | 0.3526856 |
| 717959 | PD | 19.9 | 33.81 | 0.931854315 |
| 727984 | PD | 8 | 53.39 | 1.11136624 |
| 709115 | CR | 89 | 59.82 | 48.182019 |
| 740402 | PR | 89 | 85.3 | 60.2013266 |
| 771224 | PR | 115 | 72.67 | 79.9936826 |
| 514240 | PR | 104.9 | 63.75 | 63.9045555 |
| 779512 | PR | 55.4 | 74.81 | 15.37185407 |
| 775593 | PR | 58 | 58.23 | 16.58611674 |
| 794528 | PR | 130 | 67.52 | 83.8436352 |
| 693301 | PR | 99 | 70.57 | 68.50893258 |
| 783826 | PR | 74 | 61.66 | 37.81149012 |
| 739432 | PR | 80.6 | 43.08 | 12.09383978 |
| 772579 | PR | 150 | 54.08 | 77.850864 |

Table 2 below summarizes the averages of these parameters between the two outcome groups and the p values derived using a two-tailed student t test for significance. These results indicate a high statistical relevance, especially of the total number of infused CD8+BTLA+TIL

TABLE 2

SUMMARY OF AVERAGE BTLA+ TIL
INFUSED WITH TYPE OF CLINCIAL RESPONSE

| PARAMETER | TYPE OF RESPONSE | | |
|---|---|---|---|
| | PD | PR/CR | P VALUE |
| % BTLA+ IN CD8+ TIL | 40.78 | 64.77 | 0.001966234 |
| TOTAL CD8+BTLA+ TIL INFUSED | 8.05 | 51.29 | 0.000103686 |

Products and services presented include: (1) the selection of highly effective TIL effector cells using a BTLA+ cell selection protocol and/or kits specifically designed for ACT of melanoma using a clinical grade device; (2) a biomarker for active TIL in ACT predicting which patient will respond to ACT; and (3) drugs or antibody therapies that can manipulate BTLA expression or signaling on cells and enhance the efficacy of ACT used either during TIL expansion or after TIL infusion into patients as a form of immunomodulatory therapy enhancing TIL function in vivo.

BTLA is a marker for TIL mediating clinical responses in adoptive cell therapy. However, this finding may not necessary mean that the actual function of BTLA is a positive signaling pathway for TIL. If BTLA is a negative signaling molecule in the TIL and that by blocking its activity improves TIL effector function against cancer cells, then monoclonal antibodies are useful against BTLA to block BTLA signaling and improve TIL effector functionality.

EXAMPLE II

In this continued study, we undertook a Phase II ACT clinical trial for metastatic melanoma using expanded TIL followed by HD IL-2 in 31 patients treated with a prior cyclophosphamide and fludarabine lymphodepleting regimen. Our purpose was to determine clinical response rates and to determine phenotypic markers of the infused T-cells that were most highly associated with clinical response. In addition, we determined TIL persistence and telomere length comparing responders and non-responders to determine predictive markers of therapy effectiveness.

Materials and Methods Patient Population and Prior Therapy

Patient enrollment, TIL expansion and infusion, and HD IL-2 therapy was carried out under a protocol (2004-0069) approved by the Institutional Review Board of the MD Anderson Cancer Center and an FDA-approved IND (NCT00338377). Both male and female patients with Stage 1V melanoma, Stage III in-transit disease, or recurrent regional nodal disease (Stage Ilk) over the age of 18 were enrolled following informed consent. One patient under the age of 18 (a 15-year old female; Patient #2247) was enrolled after a compassionate exemption was approved by the FDA. All types of prior therapy were allowed, including chemotherapy, biochemotherapy, targeted therapy with tyrosine kinase inhibitors and anti-angiogenic agents, and immunotherapy. Patients with brain metastases of ≤1 cm and stable for at least 1 month were included. Please refer to clinical trial NCT00338377 in the NCI website (http://www.cancer.gov/clinicaltrials) for further details on patient inclusion and exclusion criteria. Table 3 and Table 4 herein further provide further information on the accrued patient clinical and demographic characteristics. All patients were HLA typed at the HLA-A locus in the MD Anderson HLA Typing Laboratory. Expanded TIL was used for functional and phenotypic analysis under an IRB-approved protocol (LAB06-0755) approved by the MD Anderson Cancer Center IRB.

TABLE 3

Demographics and Clinical Characteristics of Enrolled Patients

| Parameter | Number |
|---|---|
| Total patients | 31 |
| Sex | |
| Male | 20 (65%) |
| Female | 11 (35%) |
| Age (years) | |
| <20 | 1 (3%) |
| 20-49 | 17 (55%) |
| 50-70 | 13 (42%) |
| HLA-A0201 status | |
| Positive | 10 (31%) |
| Negative | 22 (69%) |
| ECOG Performance status* | |
| 0 | 18 (58%) |
| 1 | 13 (42%) |
| Stage | |
| IIIc | 9 (6.5%) |
| IVa | 1 (3%) |
| IVb | 8 (26%) |
| IVc | 20 (64.5%) |
| Prior therapy | |
| Chemotherapy | 5 (16%) |
| Biochemotherapy | 9 (29%) |
| Cytokine (IL-2/IFN-α/GM-CSF) | 12 (39%) |
| Targeted therapy | 4 (13%) |
| Unknown | 1 (3%) |

TABLE 4

Patient Treatment, Sites Of Disease, And Clinical Outcome

| Patient number | Sites of disease | | | | | | | infused cells ($\times 10^9$) | Clinical response[b] | | PFS[c] mos. | OS[c] (mos.) |
|---|---|---|---|---|---|---|---|---|---|---|---|---|
| | SC[a] | LN | Lung | Liver | Other visceral | Bone | Brain | | irRC | RECIST | | |
| 2131 | | X | X | | | | | 89 | PR | PR | 15 | 31+ |
| 2173 | X | | | | X | X | | 115 | PR | PR | 7 | 15 |
| 2150/2153 | | X | X | X | X | | | 89 | PR | PR | 27+ | 27+ |
| 2124 | X | X | | | | | | 104.9 | PR | PR | 27+ | 27+ |
| 2180 | | X | | | | | | 58 | PR | PR | 9 | 26+ |
| 2215 | | X | | X | X | X | | 130 | PR | PR | 23+ | 23+ |
| 2262 | | X | | | X | | X | 99 | PR | MR | 2 | 18+ |
| 2258 | | X | X | X | | | | 74 | PR | PR | 16+ | 17+ |
| 2054/2256 | X | X | | | | | | 80.6 | PR | PR | 16+ | 16+ |
| 2261 | X | X | | | | | | 150 | CR | CR | 12+ | 12+ |
| 2267 | X | X | X | | | | | 57 | PR | PD | 2 | 14+ |
| 2357 | X | | X | X | | X | X | 109 | PR | PR | 9+ | 9+ |
| 2340 | X | X | X | | X | | X | 46 | PR | PR | 9+ | 9+ |
| 2350 | X | | X | | X | | X | 105 | PR | PR | 7+ | 7+ |
| 2379 | X | | X | | | | | 100 | PR | PR | 4+ | 4+ |
| 2044 | | X | X | X | | | | 19.9 | SD | SD | 3 | 4 |
| 2125 | X | X | | X | X | | | 68 | SD | SD | 4 | 6 |
| 2132 | X | | | X | X | | | 35 | SD | SD | 4 | 5 |
| 2114 | X | X | X | | | | | 8 | SD | SD | 3 | 25 |
| 2104 | | X | | | | X | | 85 | PD | PD | 2 | 5 |
| 2146 | X | | X | X | X | X | | 8 | SD | PD | 1 | 8 |
| 2138 | | X | X | X | | | X | 79.8 | PD | PD | 1 | 7 |
| 2175 | | X | X | | | | | 55.4 | SD | SD | 25+ | 25+ |
| 2144 | X | X | X | | | | | 54.6 | PD | PD | 3 | 18 |
| 2247 | X | X | X | X | | X | X | 60 | PD | PD | 1 | 5 |
| 2281 | | X | | X | X | | | 62.5 | PD | PD | 1 | 6 |
| 2245 | | X | | | | X | | 38 | PD | PD | 2 | 4 |
| 2338 | | X | | | | | X | 35 | PD | PD | 6 | 10+ |
| 2284 | | X | X | | | | | 86 | SD | PD | 6 | 8+ |
| 2373 | X | X | X | | | | | 59.2 | PD | PD | 3 | 5+ |
| 2299 | | X | X | | | | | 53.8 | SD | SD | 5+ | 5+ |

[a]Abbreviations: CR, complete response; PR, partial response; MR, mixed response; SD stabilization of disease; PD, progressive disease; PFS, progression-free survival; OS, overall survival; SC, subcutaneous; LN, lymph node.
[b]Best overall response measured by irRC criteria or RECIST.
[c]Based on irRC (as of Mar. 1, 2011).

Tumor Isolation and Initial TIL Expansion from Tumor Fragments

TIL were obtained from resected tumors and expanded under current Good Manufacturing Practices (cGMP) conditions in the GMP Cell Processing Facility at MD Anderson Cancer Center. In most cases, one solitary tumor nodule was selected for TIL expansion, while in some cases two to three smaller nodules were used. In previous studies we have found no association between the success of TIL expansion and the site of tumor resection. TIL were expanded from 3-5 mm$^3$ cut tumor fragments according to previously published methods after removing extraneous connective, necrotic, and non-tumor tissue using manual dissection. Briefly, multiple tumor fragments (1 per well in 24-well plates) were placed in culture with TIL culture medium (RPMI-1640 supplemented with 10% human AB serum, 10 mM HEPES pH 7.4, 100 Units/ml Penicillin G, 100 µg/ml Streptomycin, 50 µg/ml Gentamicin and 50 µM β-mercaptoethanol) and 6,000 IU/ml of IL-2 (Proleukin™; Prometheus, San Diego, Calif.). The cells were cultured for up to 5 weeks. Cultures with visible TIL were allowed to grow to confluence and sub-cultured by splitting 1:1 with TIL culture medium containing 6,000 IU/ml of Viable cell counts were performed using Trypan Blue exclusion with a hemocytometer or a Cellometer™ automated cell counting instrument (Bethesda, Md.). Patients with initial total TIL outgrowth of at least $48 \times 10^6$ from all cultured tumor fragments were eligible to receive ACT after secondary large-scale expansion of the cells using a rapid expansion protocol ("REP") as described below. The TIL obtained after 5 weeks in culture from tumor fragments were designated as "pre-REP" TIL. The pre-REP TIL were cryopreserved after testing for anti-tumor reactivity (see below) and thawed when needed for secondary expansion to treat patients, Melanoma Cell Lines and Measurement of Anti-Tumor Cell Reactivity of Pre-REP TIL We attempted to generate an autologous melanoma cell line for each patient from the tumor sample used for pre-REP TIL outgrowth. Briefly, leftover tumor nodule tissue was digested using a cocktail of enzymes consisting of collagenase, hyaluronidase Type V, and DNase I Type IV (Sigma-Aldrich, St. Louis, Mo.) and the tumor cells enriched after centrifugation over a Ficoll gradient, as described previously. The tumor cells were plated into 6-well plates and then transferred to T-25 and T-75 flasks as the cells expanded. The lines were expanded for 5 weeks and used as autologous tumor targets to measure pre-REP TIL anti-tumor reactivity. As shown in Table 5 below, we were successful in 17/31 cases to generate an autologous tumor line for testing. In cases where an autologous tumor line was not available, allogeneic HLA-A-matched tumor cell lines from our bank were used as targets to determine TIL reactivity. TIL from successfully expanded tumor fragment cultures (at least $48 \times 10^6$ TIL) were tested for anti-tumor reactivity by measuring IFN-γ production using ELISA on culture supernatants collected from triplicate 2.4-h co-cultures of 1×10⁵ TIL with 1×10⁵ autologous or HLA class I-matched allogeneic melanoma lines in 96-well plates. In some cases, both autologous targets as well as a HLA-A-matched allogeneic targets were used. At least one to two HLA-A-unmatched (at both loci) tumor cell lines were used as control. Pre-REP TIL (1×10⁵/well) plated alone with culture medium served as an additional background subtraction control. Positive control for IFN-γ production consisted of wells with TIL alone treated with PMA (50 pg/ml) and Ionomycin (2 ELISA was done using ELISA kits from Pierce (St. Louis, Mo.). An average ≥100 pg/ml after background subtraction and subtraction of HLA-A-unmatched controls was considered as positive.

TIL Therapy and Blood Sampling

Each patient received a course of lymphodepleting chemotherapy before TIL infusion (day 0) with cyclophosphamide (60 mg/kg) on day −7 and −6 and fludarabine (25 mg/m²) given from day −5 to day −1. The harvested autologous TIL (500 ml cell suspension in saline) were intravenously infused into each patient over a 20 min period by gravity using a regular infusion line with an in-line 100 μm mesh to remove any large aggregates or debris. The following morning, the patients received bolus IL-2 (720,000 IU/kg) every 8 h to tolerance. A second course of HD IL-2 therapy was given approximately 21 days after TIL infusion in a similar manner. Hematologic and biochemical parameters were monitored daily during IL-2 administration. Intravenous blood samples (10 ml) were collected from patients before and after lymphodepletion on day −7 and day 0 before chemotherapy and before TIL infusion, respectively. Subsequent blood samples (50 ml) were collected on days 7, 14, 21, 35, and 70 after TIL infusion. The samples were analyzed using a complete blood analysis (CNT/DIF/PLT) in the Division of Pathology and Laboratory Medicine at MD Anderson Cancer Center.

Measurement of Clinical Responses by irRC and RECIST

Tumor response to therapy was done using immune-related response criteria (irRC) which is a modified version of the WHO criteria. All measurable lesions, up to a maximum of five lesions per organ and ten lesions in total were identified as index lesions to be measured and recorded on the medical record at baseline. Lesions were selected based on their size (lesions with the longest diameters), their suitability for accurate repeat assessment by imaging techniques, and how representative they were of the patient's tumor burden. Lesions that were accurately measured in two perpendicular diameters, with at least one diameter ≥10 mm, were defined as measurable lesions. In the case of cutaneous lesions, ≥5 mm in diameter were considered measurable. The area for each index lesion was calculated as the product of the largest diameter with its perpendicular and a sum of the products of diameters (SPD) for all index lesions was calculated and considered the baseline sum of the products of diameters. Measurable lesions, other than index and all sites of non-measurable disease were identified as non-index lesions. Non-index lesions were recorded on the medical record and evaluated at the same assessment time points as the index lesions. Complete assessment of evaluable lesions with physical examination and appropriate CT scans were performed at baseline and repeated approximately at 6 weeks (+/−7 days) and at 12 weeks (+/− 7 days) after the cell infusion. Immune-Related Best Overall Response (irBOR) was the best confirmed irRC overall response over the study as a whole, recorded between the date of first dose until the last tumor assessment before subsequent therapy (except for local surgery or palliative radiotherapy for painful bone lesions) for the individual subjects in the study. For assessment of irBOR, all available assessments per subject were considered. If a lesion was surgically resected or treated with definitive radiosurgery, the size of the lesion prior to the definitive local therapy was included in the calculated irBOR. Complete responses and progressions were confirmed by a second, consecutive assessment at least tour week apart.

TABLE 5

Derivation of the irRC Best Overall Score

| Measureable response | Non-measureable response | | |
|---|---|---|---|
| Index and new M lesions | Non-index lesions | New NM lesions | Overall response |
| Decrease 100% | No | No | irCR |
| Decrease 100% | Stable | Any | irPR |
| Decrease 100% | Progression | Any | irPR |
| Decrease ≥50% | No/Stable | Any | irPR |
| Decrease ≥50% | Progression | Any | irPR |
| Decrease ≥50 to <25% | No/Stable | Any | irSD |
| Decrease ≤50 to <25% | Progression | Any | irSD |
| Increase ≥25% | Any | Any | irPD |

M = measureable;
NM = Non-measureable

Flow Cytometry Analysis of Infused TIL

Antibodies to human CD4, CD8, CD27, CD28, CD62L, CD45RA and CD272 (BTLA, clone J168-540.90.22) were from BD Biosciences (San Jose, Calif.). Antibodies to human CD279 (PD-1, clone EH12.2H7) and Perforin (clone dG9) were obtained from BioLegend (San Diego, Calif.). Anti-human TIM3 (clone F38-2E2) was from eBiosciences (San Diego, Calif.), anti-human LAG-3 (clone 17B4) was obtained from Enzo Life Sciences (Plymouth meeting, PA) and anti-human CD270 (HVEM, clone ANC3B7) was purchased from Ancell (Bayport, Minn.). Staining of all TIL infusion products was done on samples cryopreserved immediately following harvesting of the clinical TIL products and washing and concentrating using the Cobe 2991 machines.

Briefly the samples were thawed in pre-warmed complete media (RPMI-1640 supplemented with 10% human AB serum, 10 mM Hepes, 100 Units/ml Penicillin G, 100 μg/ml Streptomycin, 50 μg/ml Gentamicin and 50 μM β-mercaptoethanol), washed in PBS, and first stained with a fixable viability dye (LIVE/DEAD® Fixable Aqua Dead Cell Stain, Invitrogen) for 30 min at 4° C. Cells were then washed twice in FACS Wash Buffer/FWB (D-PBS, 1% BSA), re-suspended in FACS staining buffer/FSB (D-PBS, 1% BSA, and 10% goat serum) and stained with antibody mixtures at the manufacturer's recommended concentration or otherwise experimentally optimized concentrations for 20 minutes in the dark, at room temperature. The Perforin intracellular staining was done according to manufacturer's instructions. Samples were subsequently washed twice in FACS wash buffer and fixed in 1% paraformaldehyde solution in PBS containing 0.2% ethanol. Acquisition was done the next day, samples were read on a FACSCanto II instrument (BD Biosciences) and data analysis was performed using FlowJo software (Tree Star, Inc., Ashland, Oreg.). Live cells were first gated using FSC and SSC parameters and dead cell exclusion was then performed by gating Out the Aqua positive cells before gating on any antibody positive populations. For CD8⁺ differentiation status determination, the Aqua negative cells were gated on CD8⁺CD4⁻ cells. This CD8⁺ population was then further selected for CD45RA⁻ (which constitute the overwhelming majority of TIL) and the resulting population was analyzed on a plot of CD62L versus CD27 where CD27⁺CD62L⁺ cells were designated TCM (central memory), CD27⁺CD62L⁻ TEM (effector-memory), and CD27⁺CD62L⁻ TEFF (effector).

Tracking of TCR Vβ Clonotypes Post-Infusion by Gene Cloning and Sequencing

Total RNA was isolated from TIL or patients PBMC after adoptive transfer using Qiagen RNeasy Kit (74104). RNA quality was monitored by running an agarose gel to check RNA degradation. TCR Vβ specific cDNA was synthesized using Clonetech 5' RACE smarter kit. The primer in cDNA synthesis specifically binds to the Vβ constant region and can recognize both C1 and C2. During cDNA synthesis, a 5' end adapter was added to each cDNA. Nested primers for adapter and Vβ constant regions were used for PCR amplification. The resulting Vβ specific PCR products were purified from an agarose gel and ligated into a TA cloning vector (Invitrogen). For TCR Vβ gene analysis, 96 TCR Vβ positive DNA samples were prepared and confirmed, and then sequenced. To characterize each individual TCR Vβ clones, each sequence data was further analyzed using the IMGT program, Detection of Telomere Length in TIL by Southern Blotting TIL genomic DNA was isolated using a Qiagen DNA Prep kit following the manufacturer's instructions. Genomic Southern blotting was performed using a TeloTAGGG Telomere Length Assay kit (Roche Diagnostics, Indianapolis, Ind.). Briefly, 2 µg genomic DNA was digested by restriction enzymes HinfI and RsaI and then separated on a 1% agarose Known telomere repeat lengths ranging from 21.4 to 1.9 kb were run along side the digested samples. The fractionated DNA was transferred overnight onto Nytran supercharged membranes using the Turbo blotter system with 20×SSC buffer (Schleicher and Schell Bioscience). Following 3 hours of hybridization at 42° C. with the digitoxigenin (DIG)-labeled telomere repeat probe supplied with the kit, the membrane was washed and incubated with anti-DIG-alkaline phosphatase solution for 30 mm at room temperature. The telomere length signal was detected by chemoluminescence reagents (Pierce, St. Louis, Mo.) and the blots exposed to X-ray film. The exposed films were imaged using a Perfection V700 Flatbed Scanner (Epson) and saved as TIFF image files for analysis. The telomere lengths were determined using the ImageJ analysis program downloaded from the National Institutes of Health (NIH, Bethesda, Md.) website (rsbweb.nih.gov/ij/).

A standard curve of migration distance from the first and longest telomere standard (21.4 kb) to the last and shortest telomere standard (1.9 kb) was established, with the 21.4 kb band designated as 0 mm and a migration distance assigned to each subsequent standard in mm from this point. All detected telomeres detected were within this range. The position of the maximal telomere signal density in each sample in the other lanes was determined and this position was then converted into telomere size in kb by matching this same location in the lanes with the standards and then converting this mm length to actual telomere length in kb using the standard curve.

Determination of HVEM Impact on TIL Cell Survival

TIL expanded from melanoma tumors with high-dose IL-2 (3,000-6,000 ti/ml human IL-2) were tested in two scenarios for whether HVEM (the ligand for BTLA) could facilitate the survival of CD8⁺ TIL. These experiments used a murine fibroblast cell line expressing an Fc receptor (CD32) with or without human HVEM on the cell surface. The L cells were irradiated with 5,000 Rads and plated into 24-well plates for 6 hours to form a monolayer of cells. After washing of non-adherent L cells, 5×10⁵ CD8⁺ TIL were added to the cultures and the incubated for 5 days. After 5 days, the cell were harvested and analyzed by flow cytometry for the degree of apoptosis in the CD8⁺ cell subset. Here, the cells were washed 2 times with PBS and re-suspended in 100 µl Annexin V binding buffer (BD Biosciences, San Jose, Calif.) and stained with anti-CD8 Pacific Blue (RPA-T8, BD) and Annexin V APC (BD) for 20 mm in the dark at room temperature. Cells were then washed to remove excess antibody, re-suspended in Annexin V binding buffer, and stained with MAD (BD) for 10 min in the dark at RI. Cells were run on a FACSCanto II (BD) flow cytometer and analyzed with FlowJo (TreeStar version 7.6.5).

Statistical Analysis

Figure 25A:
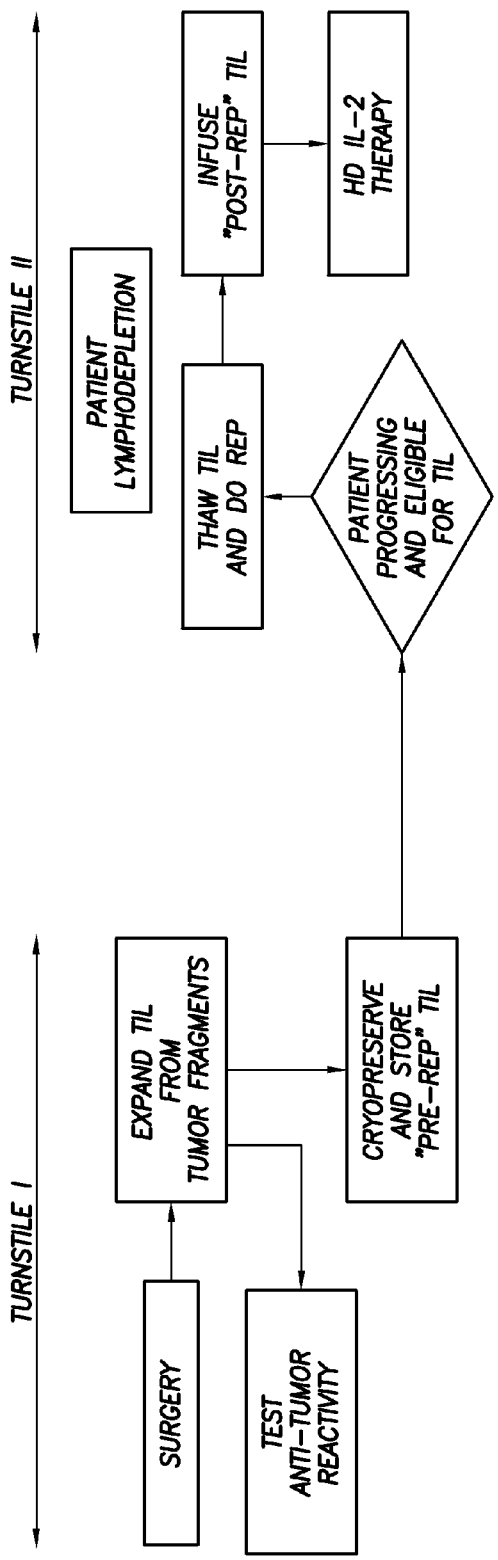
FIGS. 25A and 25B are illustrative of the scheme of TIL adoptive cell therapy clinical trial.
Figure 25B:
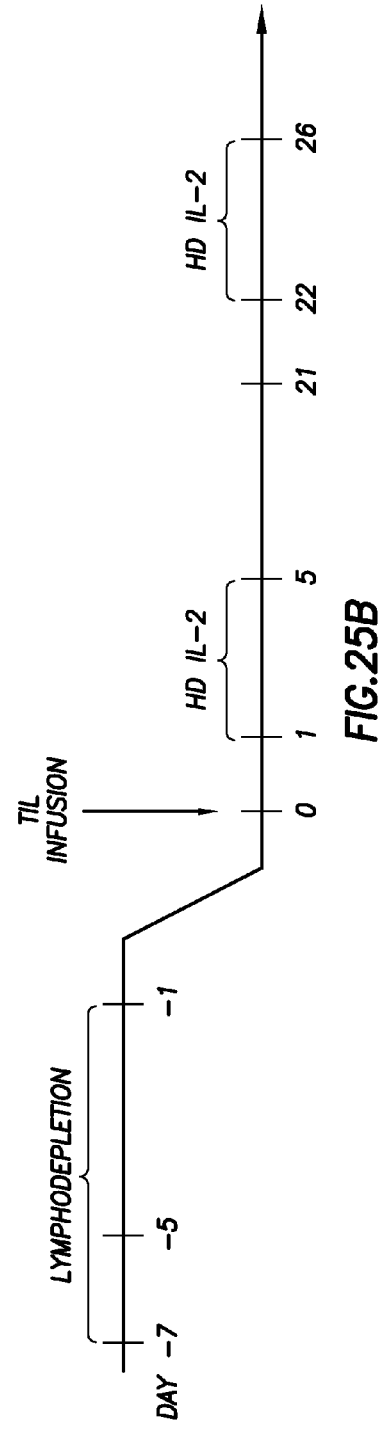

For categorical variables, Fisher's exact test and its generalizations were used to assess association with tumor response. The number and percent is provided for each level of the categorical variable, for responders and non-responders. For continuous variables, the Wilcoxon rank-sum test was used to assess association with tumor response, with P-values were computed using the normal approximation. The median, minimum, and maximum of each continuous variables is given, for responders and non-responders. All P-values are two-sided with P<0.05 considered as being significant. No adjustment for multiple comparisons was performed, although it is very important to note that, using the Bonferroni correction for multiple comparisons, to ensure an overall false negative probability of 0.05, each P-value would need to be less than 0.05/24=0.0021 for the test for that variable to be considered significant. All statistical analyses were performed using SAS 9.2 for Windows (Copyright© 2011 by SAS Institute Inc., Cary, N.C.) or Graph Pad Prism 5 software, Patient Population and TIL Therapy Patients of any HLA subtype with Stage IIIc-IV disease were recruited into the study. FIG. 25A shows the overall design that contained two major stages or "turnstiles". Turnstile I consisted of an initial expansion of TIL from a tumor harvest from an accessible metastatic site by surgery and expansion of the TIL from a minimum of twelve 3-5 mm³ tumor fragments with IL-2 (6,000 IU/ml) for up to 5 weeks. These "pre-REP" TIL were cryopreserved and thawed when the patient needed the actual expanded TIL therapy due to disease progression (Turnstile II of the protocol). FIG. 25B summarizes the process flow for the TIL infusion and high-dose (HD) IL-2 therapy.

The cryopreserved pre-REP TH, from the 31 patients were thawed and subjected to the REP to generate the final TIL infusion product (Turnstile II in FIG. 25A). Patients were lymphodepleted using cyclophosphamide (Cy) and fludarabine (Flu) and then infused with TIL. This was followed by two cycles of HD IL-2 therapy, with the first cycle beginning the following day after TIL infusion and the second cycle starting at approximately 22 days after TIL infusion (FIG. 25B). Table 3 above summarizes the demographic and clinical characteristics of the treated patients (n=31).

Most patients were Stage IV at the time of TIL infusion and had received a variety of different prior therapies within 2 months of therapy, including biochemotherapy, radiotherapy, targeted therapy, and immunotherapy with IL-2, IFN-α or GM-CSF. The median age was 46 years with 35% females and 65% males. Table 2 shows number of TIL infused for each patient after the REP. The mean fold-expansion of TIL over the entire treated population was 1,730 (±811, range 359-4,260). The total TIL infused ranged from 8-150×10⁹ cells.

Treatment-Related Toxicity and Measurement of Hematopoietic Parameters

Patients experienced only transient, reversible adverse reactions (e.g., fever, chills, shortness of breath, increased heart rate) in the few hours following TIL transfer. No Grade 3 or 4 toxicities according to the National Cancer Institute Common Toxicity Criteria (NCICTC) were noted after TIL infusion before HD IL-2 therapy. Hematologic toxicities due to the preparative chemotherapy were anticipated and transient. Neutropenia and lymphopenia were observed in all patients necessitating treatment with antibiotics. All patients were also treated with platelet transfusions and red blood cell transfusion and increased back to normal levels.

Figure 26B:
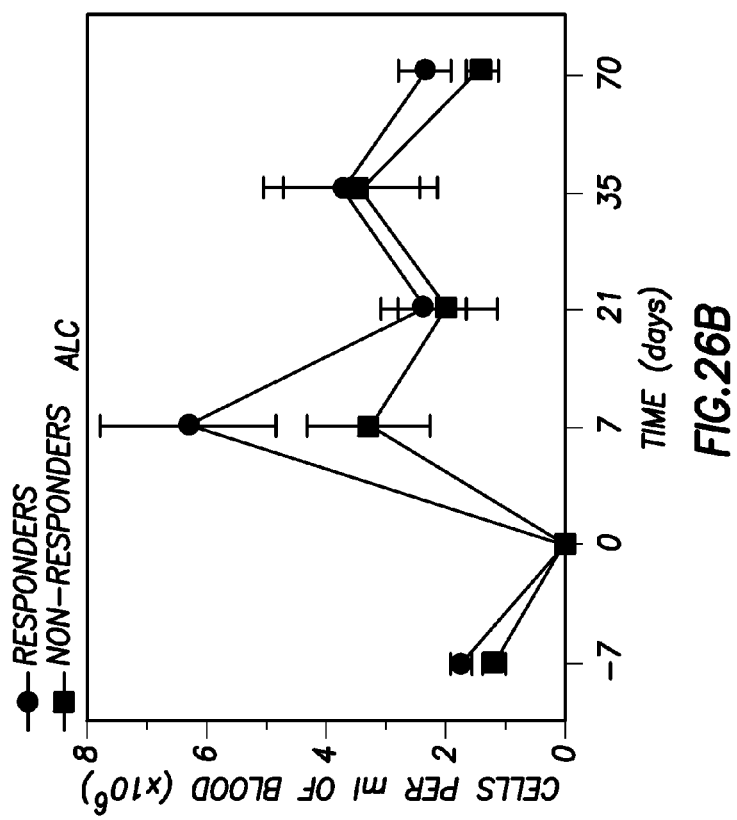
Figure 26A:
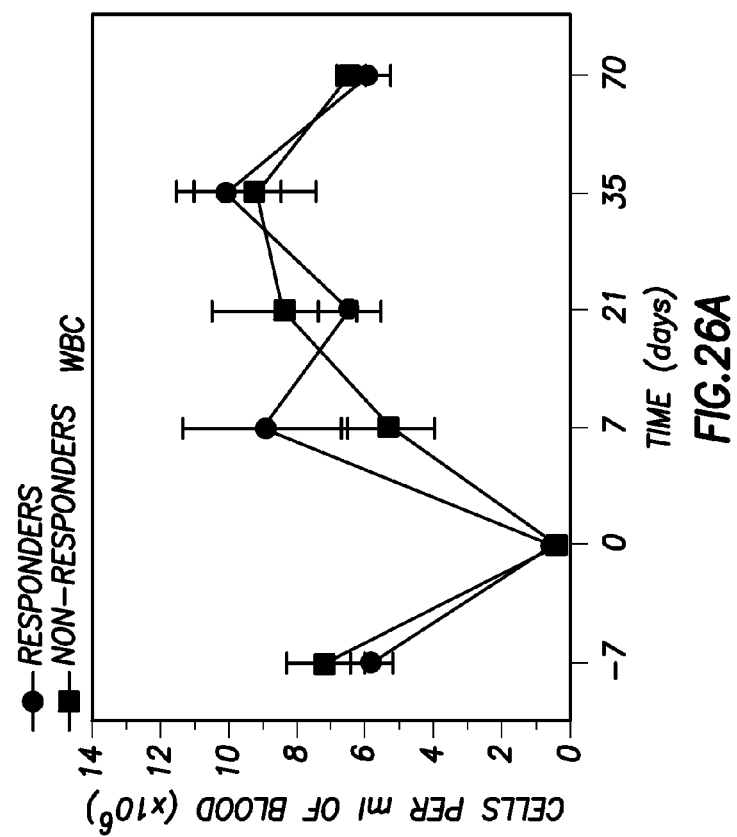

FIGS. 26A through D show the drop of total white Hood cells (WBC), absolute neutrophil count (ANC), and absolute lymphocyte count (ALC) after the preparative chemotherapy and also shows the recovery of these populations following TIL infusion over a 70-day period in all patients, comparing the responders and non-responders. FIGS. 26A-C show changes in WBC (FIG. 26A), ALC (FIG. 26B), and ANC (FIG. 26C) from day −7 and after lymphodepletion (day 0) and TIL transfer (days 7, 21, 35, and 70) in responding (n=15) and non-responding patients (n=16).

In each case, baseline levels for each cell type was recovered with lymphocytes showing an overall elevated level over day −7. There was a spike in ALC on day 7 and day 35 representing samples taken after each cycle of HD IL-2 therapy. Notably, responders had a higher mean ALC on day 7 after the first IL-2 cycle although not significantly different (p=0.079) (FIGS. 26A through C).

However, this day 7 ALC was not significantly correlated with the total number of TIL infused (r=0.322 by Pearson correlation co-efficient analysis). FIG. 26D shows all 31 patients. However, two sub-groups of patients become evident in the graph; those with day 7 ALC>7×10⁶/ml and those <7×10⁶/ml. The patient with an ALC>7 had a narrower range of total infused between 58 and 109 billion, while the day 7 ALC of <7 was associated with a wider range of infused TIL (between 8 and 150 billion). Bars in graphs are standard error of the means.

The usual Grade 3 and 4 toxicities according) the NCICTC were found with bolus HD IL-2 infusion (pulmonary, renal, and liver dysfunction, and mental confusion). However, all these were transient in nature and responded to standard interventions and/or resolved after IL-2 therapy. Most patients (28/31) received two cycles of IL-2 therapy; three patients did not receive the second cycle of TIL-2 due to disease progression (#2247) or due to a clinical decision based on toxicities during cycle 1 of IL-2.

Clinical Responses and Correlation with Patient Clinical Parameters

In this study we determined clinical response rates according to the new irRC criteria established by Wolchok et al. that more closely reflects the dynamics of a response one would expect with immunotherapies as opposed to chemotherapies. Clinical responses were determined by CT scans and measurement of visible lesions (e.g., subcutaneous lesions near the skin surface) at 6, 12, and 16-20 weeks after TIL infusion and every 3 months after that.

FIGS. 27A through F are CT scans and photographs of sites of tumor regression following TIL infusion in two representative patients on the trial. FIGS. 27A through 27D shows regression of a large subcutaneous mass in the right shoulder and complete regression of a large inguinal lymph node lesion after 1 month in Patient #2150/2153, FIGS. 27E through J shows partial regressions of abdominal tumors after 1 month that increased further 18 months post TIL infusion in Patient #2054/2256.

Figure 28A:
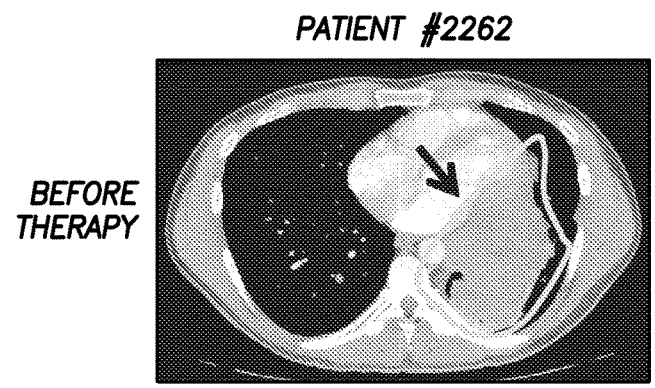
FIGS. 28A through C show durable partial response of an intra-thoracic melanoma mass near the aorta and heart in one patient at 6 weeks and 18 months after TIL infusion.
Figure 28B:
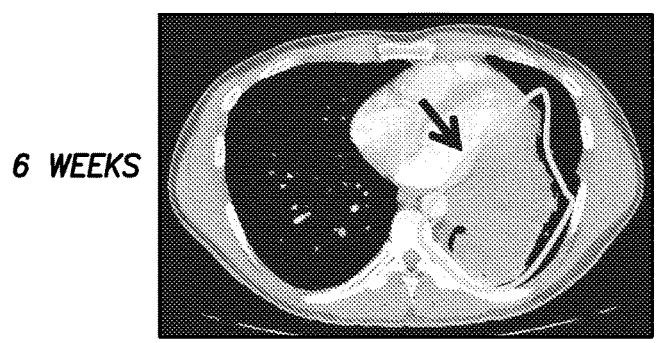
Figure 28C:
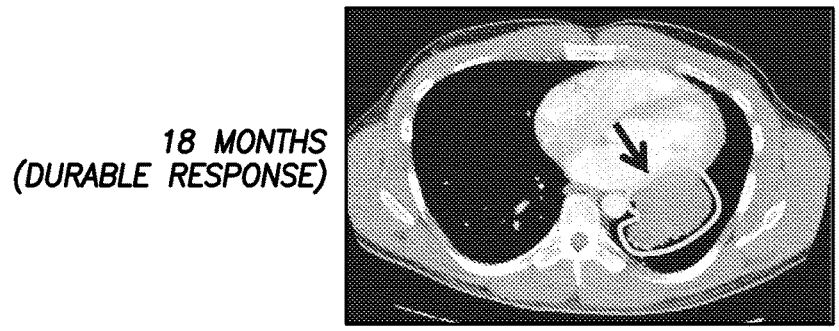

We also noted in some cases that a mass underwent a durable partial regression by CT, and the remnant lesion was no longer 2-fluorodeoxyglucose (FDG) avid by positron emission tomography (PET). An example of this is shown in FIGS. 28A through 28C for Patient #2262. Here, a large tumor mass attached to the aorta and the heart shrunk by >50% in volume and the remnant lesion persisting did not show any activity by PET scanning FIGS. 28A through 28C show the durable partial response of an intra-thoracic melanoma mass near the aorta and heart in one patient at 6 weeks (FIG. 28B) and 18 months (FIG. 28C) after TIL infusion. The lesion shrank by >50% and has remained stable for more than 18 months. PET scanning found that the remnant mass did not label with 2-fluoro-deoxyglucose (FDG).

Table 4 above shows the best overall response ("BOR") of each patient determined using both irRC and RECIST together with progression-free survival ("PFS") and overall survival ("OS") time, sites of metastatic disease, and the number of TIL infused. Patients with multiple metastatic sites responded to therapy. No association was found between a number of patient categorical variables (gender, tumor substage, and type of prior therapy) and the type of clinical response.

Table 7 below shows the association between patient gender, disease stage, prior therapy and status of TIL anti-tumor reactivity with clinical response.

|  |  | Tumor Response | | | | | |
|  |  | No | | Yes | | Total | |
| Variable |  | Count | % | Count | % | N | P-value[a] |
| Gender | Female | 4 | 36.36 | 7 | 63.64 | 11 | 0.2734 |
|  | Male | 12 | 60.00 | 8 | 40.00 | 20 |  |
| Tumor Substage | IIIc | 0 | 0.00 | 2 | 100.00 | 2 | 0.2900 |
|  | Iva | 0 | 0.00 | 1 | 100.00 | 1 |  |
|  | IVb | 6 | 66.67 | 3 | 33.33 | 9 |  |
|  | IVc | 10 | 52.63 | 9 | 47.37 | 19 |  |
| Prior therapy | Chemotherapy | 5 | 55.56 | 4 | 44.44 | 9 | 1.0000 |
|  | Biochemotherapy | 4 | 44.44 | 5 | 55.56 | 9 |  |
|  | Immunotherapy | 6 | 50.00 | 6 | 50.00 | 12 |  |
| TIL anti-tumor reactivity | No | 7 | 63.64 | 4 | 36.36 | 11 | 0.4578 |
|  | Yes | 9 | 45.00 | 11 | 55.00 | 20 |  |

Figure 29:
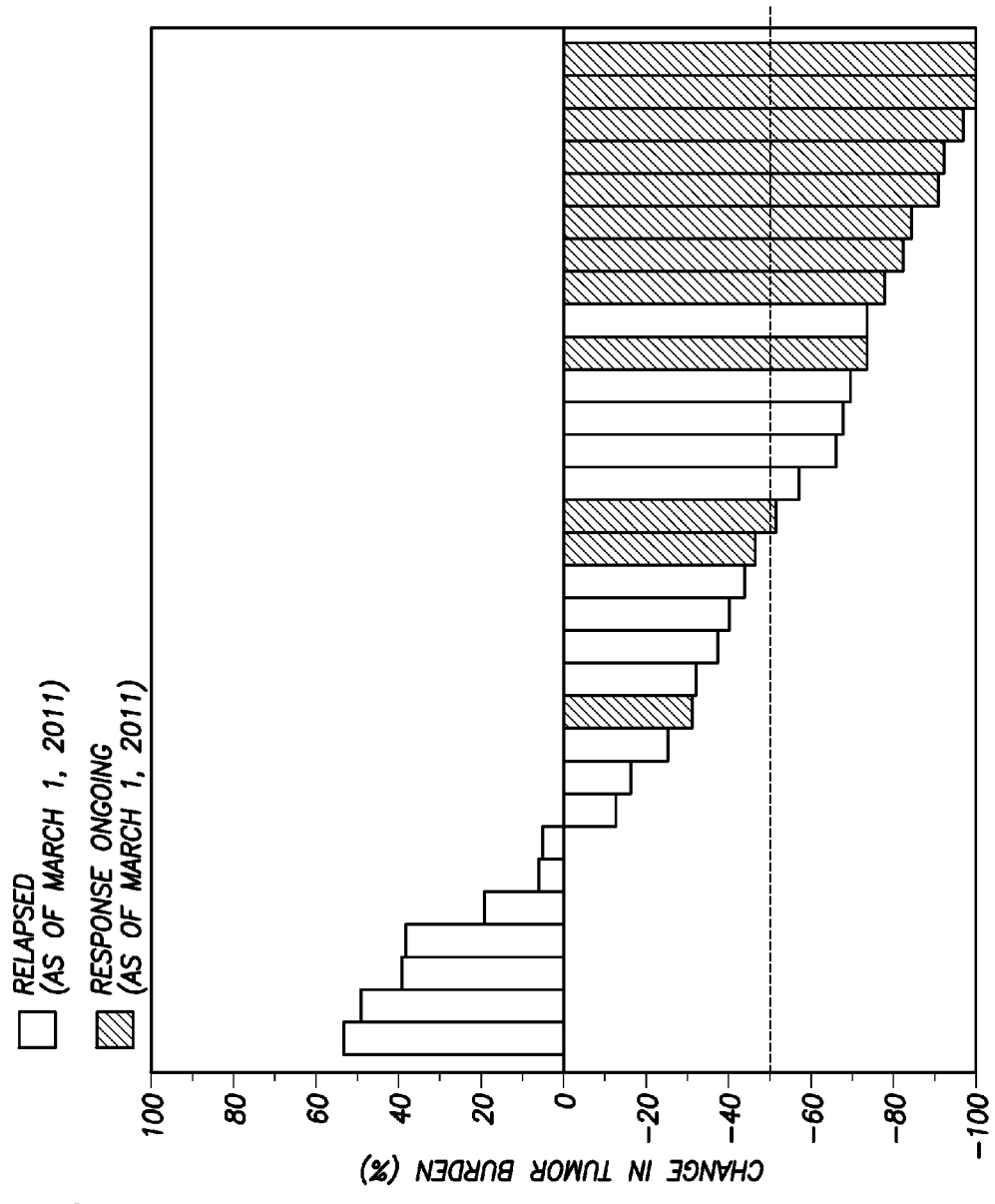
FIG. 29 is a waterfall plot of change in tumor burden in all treated patients (n=31).

In addition, age at time treatment of responders (median 44.0) and non responders (median 49.5) was not significant (p=0.906). Using irRC, the BOR (partial and complete responses) was 48.4% (15/31) while RECIST-based BOR was found to be 41.9% (13/31). Many of the clinical responses have been quite extensive, with >70% reduction in tumor burden found in the majority of responders, as shown in a waterfall plot analysis. As shown in FIG. 29, the best overall irRC response is shown for all patients. The patients were treated between Aug. 23, 2007 and Oct. 6, 2010. The hatched bars indicate patients that have continued to respond as of Mar. 1, 2011, while the empty bars indicate patients who subsequently had progressive disease after experiencing the objective response. Of the 15 patients who responded, 10 had ≥70% reduction in their tumor burden.

Overall, two patients scored as responders with irRC, but were non-responders using RECIST. Both had small recurrences shortly after TIL ACT at the same time or just prior undergoing important tumor regression of other sites of disease. One of these patients (#2262) developed small brain lesion 2 months after TIL ACT that was surgically removed. This patient is now progression-free after surgery for >17 months and other sites of disease are continuously shrinking. The other patient (#2267) developed new lesions 2 months after TIL treatment that were treated. This patient is still alive >16 months after therapy.

Figure 30A:
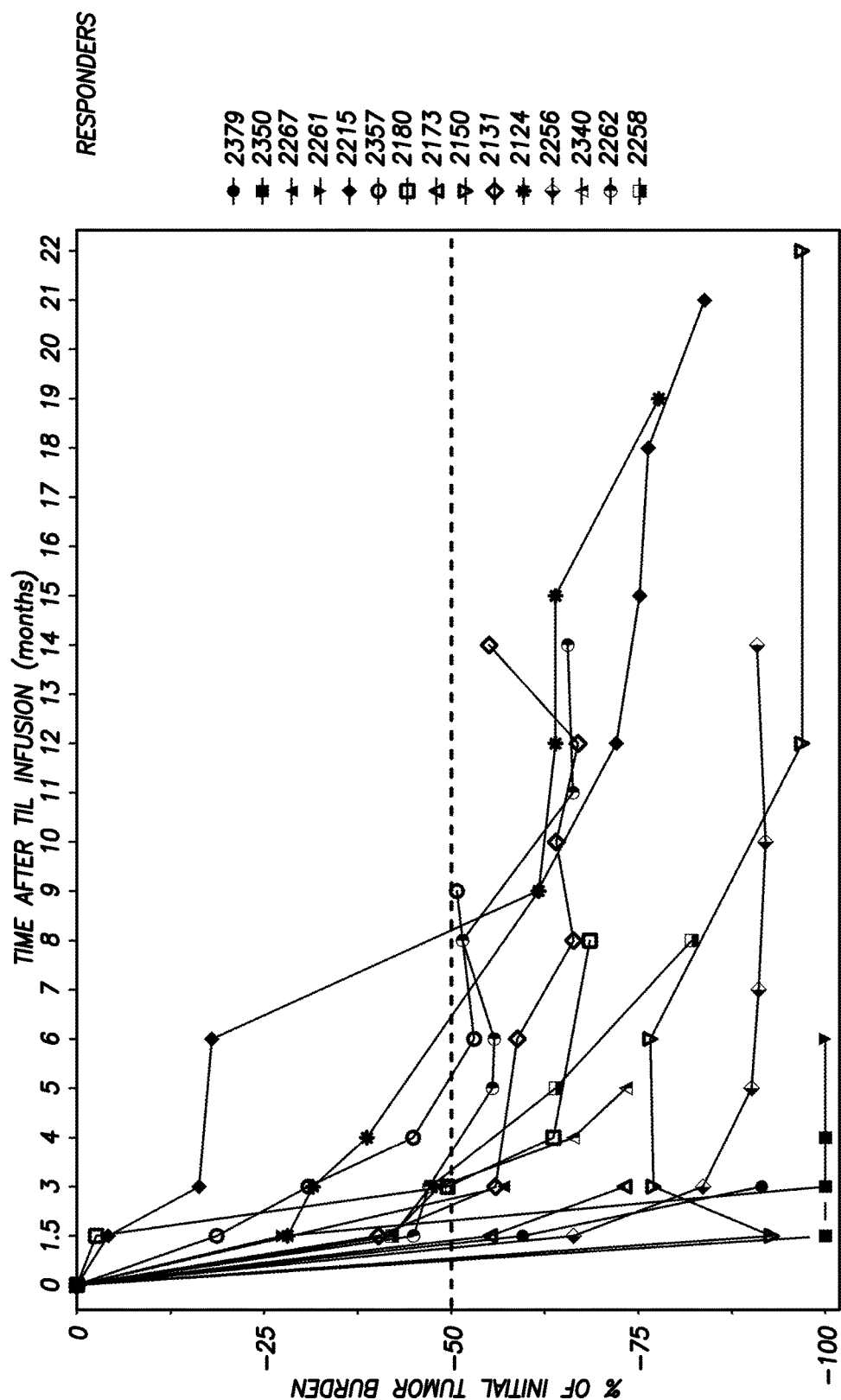
FIG. 30 shows changes in tumor burden over time following TIL transfer therapy in responders and non-responders.
Figure 30B:
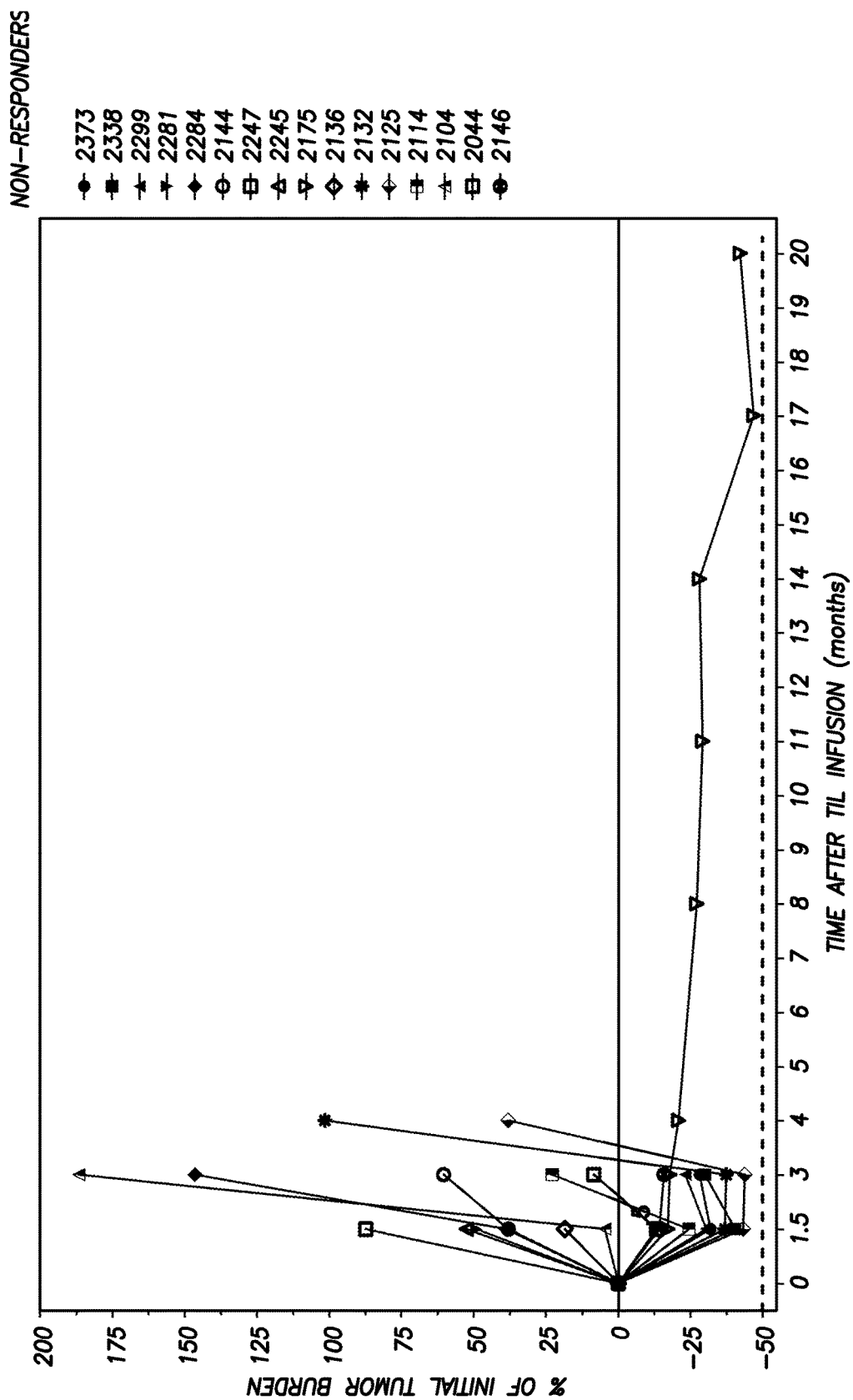

Progression-free survival (PFS) and overall survival (OS) also showed profound differences between responders and non-responders, with 9/15 (60%) of the responders experiencing >10 month PFS and 11/15 (73%) having >12 month OS (Table 4). Three of the responding patients have continued relapse-free responses for over 2 years. Notably, one additional patient (#2175), whose best response was disease stabilization, has remained progression free for over 2 years. We also tracked the changes in tumor burden over time in all treated patients. As shown in FIGS. 30A and 30B, total tumor burden (in $cm^3$) was determined using irRC before TIL therapy and at the indicated time points in months. The pre-therapy time point is designated as 0 months. The percentage change in tumor burden at each time point was then calculated and plotted for the responding (FIG. 30A) and non-responding (FIG. 30B) patients. The hatched line is drawn at the −0.50% tumor burden change marking the point at which tumor regression becomes significant in terms of the irRC criteria. This analysis found that most responding patients experienced objective tumor regression (≥50% decrease in tumor burden by irRC) by 3 months following TIL infusion (FIG. 30A). However, we noted that a subset of patients (Patients #2215, #2124, and #2357) had a protracted period of stable disease for over 4 months before experiencing objective tumor regression (FIG. 30A). Analysis of the non-responding patients revealed some interesting trends, with three major patterns emerging (FIG. 30B). There was a group of patients that exhibited immediate disease progression and a second group that experienced a decrease in tumor burden <50% over the first 1.5 to 3 months and then progressed.

A third trend was exhibited by Patient #2175 who had a long period of disease stabilization for up to 20 months (FIG. 30B). Thus, the timing of objective clinical responses following TIL infusion can vary and some patients may experience a long period of stable disease that in some cases can be associated with a delayed objective tumor regression.

Lastly, we also looked at the total tumor burden and the average number of IL-2 doses given in correlation with clinical response. Responders had a statistically insignificant difference in tumor burden at time of treatment (median of 11.51 $cm^3$) than non-responders (median 14.97 $cm^3$) (p=0.527). The average number of tolerated IL-2 doses over the whole patient population was 6.5±2.1 during the first cycle and 6.1±2.6 during the second cycle. We did not find any correlation between the number of IL-2 doses given in either cycle, with responders getting a median of 13 doses and non-responders a median of 13.5 dose (p=0.524), Pre-REP Anti-tumor Reactivity and Clinical Response The status of the pre-REP TIL anti-tumor reactivity was correlated with the type of clinical response based on irRC. This was done to determine whether the status of tumor reactivity after this initial stage in the TIL expansion process could potentially be used as a predictive marker to decide whether the cells should be subjected to large-scale secondary expansion and infusion. The percentage of treated patients having TIL exhibiting significant anti-tumor-specific IFN-γ responses (≥100 pg/ml IFN-γ after subtraction of controls) either against an autologous or at least one allogeneic matched melanoma cell line was 71% (22/31). The type of prior therapy before TIL expansion was not associated with positive or negative anti-tumor reactivity (data not shown). We were able to generate an autologous melanoma cell line for testing the pre-REP TIL for 17/31 (55%) of the patients and among these all but two TIL had specific anti-tumor IFN-γ responses. Table 6 immediately below shows the long term changes in the persistence of TCR Vβ clonotypes in the blood following TIL adoptive transfer in representative responding patients.

Table 6 immediately below provides a summary of TIL anti-tumor reactivity data for treated patients.[a]

[a]TIL anti-tumor reactivity was determined in co-cultures with melanoma cells using targets obtained from autologous, allogeneic HLA-A-matched, or both autologous and allogeneic HLA-A-matched cell lines. In each case, at least one HLA unmatched control was used. The net IFN-γ secretion for each TIL after subtraction of the HLA-unmatched control is shown in both cases above. A net level of ≥100 pg/ml was considered as reactive. TIL from each patients was scored as reactive when either an autologous or an allogeneic HLA-matched cell line target yielded the minimal net IFN-γ level. The shaded areas in grey indicate situations where no cell line was available for the assay of was not tested.

| Patient # | HLA-A sub-type | Net IFN-γ (pg/ml) Auto | Net IFN-γ (pg/ml) Allo matched | Reactivity (Yes/No) |
|---|---|---|---|---|
| 2044 | A01/A23 | 528 | 39 | Yes |
| 2125 | A29/A31 |  | 0 | No |
| 2132 | A24/A68 | 1572 | 453 | Yes |
| 2114 | A11/A11 |  | 0 | No |
| 2131 | A01/A01 | 1923 | 89 | Yes |
| 2104 | A11/A29 |  | 736 | Yes |
| 2146 | A0201/A24 |  | 0 | No |
| 2173 | A01/A26 | >2000 | 14 | Yes |
| 2150/2153 | A01/A03 | 1469 | 0 | Yes |
| 2124 | A0201/A11 |  | 0 | No |
| 2136 | A01/A29 | 787 | 0 | Yes |
| 2175 | A0201/A03 |  | 0 | No |
| 2180 | A0201/A03 |  | 0 | No |
| 2215 | A0201/A03 |  | 0 | No |
| 2144 | A0201/A0201 | 0 | 0 | No |
| 2262 | A0201/A0202 |  | 1968 | Yes |
| 2258 | A0201/A31 | 1497 | 46 | Yes |
| 2247 | A01/A01 |  | 1799 | Yes |
| 2281 | Not A0201 | 433 |  | Yes |
| 2054/2256 | A01/A24 | 0 | 0 | No |
| 2245 | A01/A03 |  | 0 | No |
| 2267 | A24/A68 |  | 1782 | Yes |
| 2261 | A0201/A03 | >2000 | >2000 | Yes |
| 2338 | A0205/A23 | >2000 | 0 | Yes |
| 2357 | A30/A32 |  | >2000 | Yes |
| 2340 | A0201/A0201 | 135 | 185 | Yes |
| 2284 | A01/A24 | 1686 | 1329 | Yes |
| 2350 | A23/A26 | 347 | 0 | Yes |
| 2373 | A03/A33 | 1205 | 774 | Yes |
| 2299 | A24/A68 |  | 0 | No |
| 2379 | A01/A23 | >2,000 |  | Yes |

Overall, no significant correlation was found between positive anti-tumor reactivity and objective (irRC) clinical response, with 11/15 (73.3%) of responders having had a significant fraction of anti-tumor-reactive TIL at the pre-REP stage and the majority of non-responders (9/16 or 56.3%) having anti-tumor-reactive TIL (p=0.458). Even when considering cases with significant autologous anti-tumor IFN-γ secretion (n=15), only 8/15 (53%) of these patients had a clinical response, while the rest (47%) did not. FIG. 39. Thus, our data suggests that positive IFN-γ secretion against melanoma cells in vitro at the pre-REP stage is not associated with a better clinical benefit from TIL therapy. Analysis of post-REP lymphocytes (infusion product) for anti-tumor reactivity however was not performed.

Immunophenotyping of Infused TIL Using Flow Cytometry

Figure 31B:
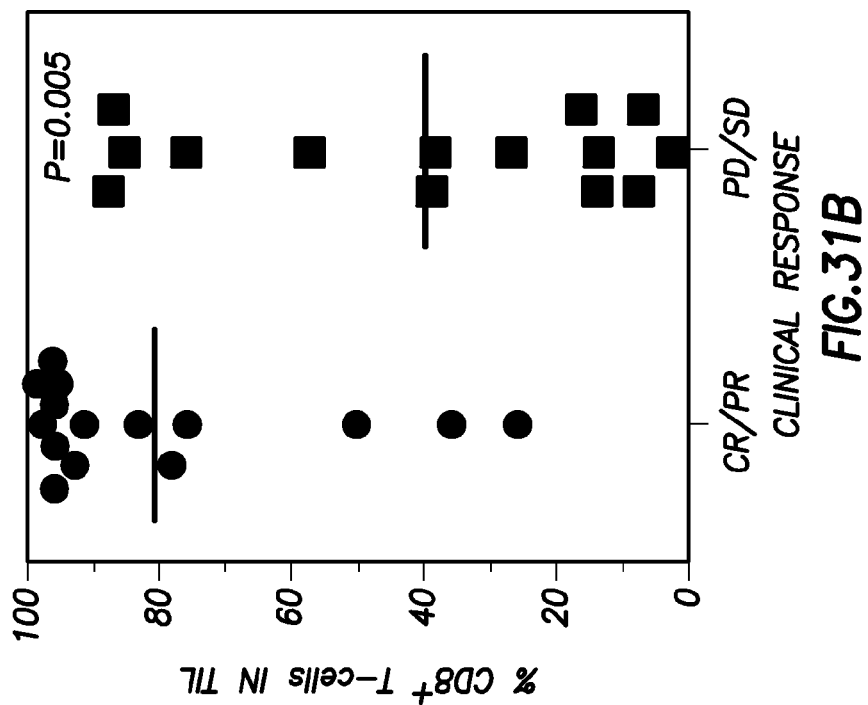
Figure 31A:
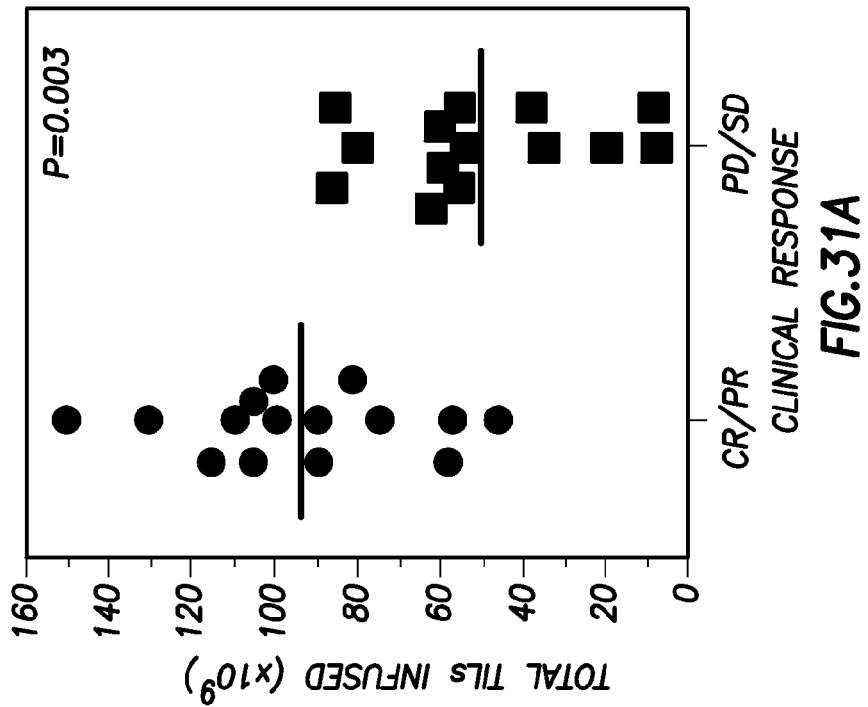
Figure 31F:
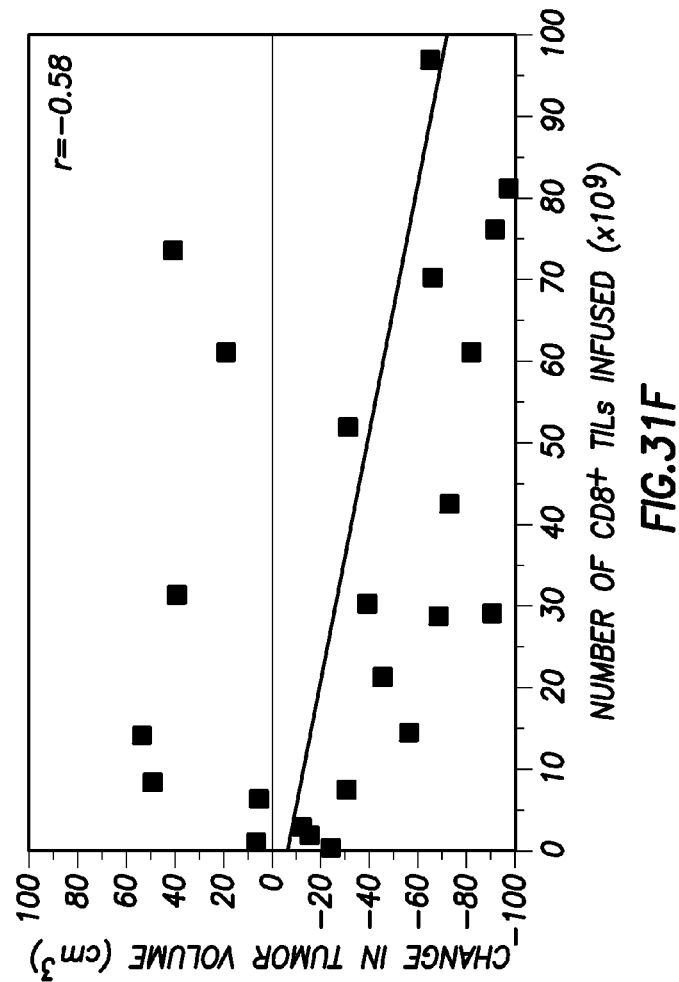
Figure 31E:
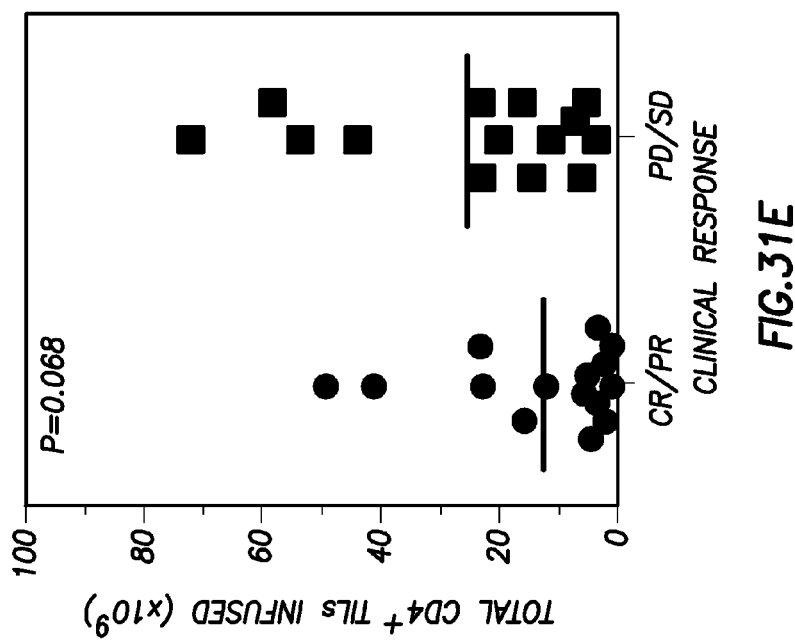

As shown in Table 4 above, different numbers of TIL were infused across the patient population, depending on the fold-expansion of the cells in the REP. In the experiments of FIGS. 31A through 31D, total TIL infused was determined using a viable cell count performed on the final harvested and concentrated TIL product. Lymphocytes in the final infused TIL product were stained with anti-CD4 and anti-CD8 and analyzed by flow cytometry. We analyzed the number of TIL infused according to the type of clinical response using irRC, and found a distinct correlation with responding patients infused with significantly more TIL (mean of $93.8 \times 10^9$ cells±28) than non-responders (mean of $50.4 \times 10^9 \pm 25.7$). (FIG. 31A) We further analyzed the different subsets of T cells using multi-color flow cytometry for the content of $CD3^+CD8^+$, $CD3^+CD4^+$ T cells. This analysis revealed a strong correlation between both the frequency (FIG. 31B) and number (FIG. 31C) of $CD8^+$ T cells infused, with higher values for both parameters associated with positive clinical responses. Higher percentages (FIG. 31D) and numbers (FIG. 31E) of $CD4^+$ T cells infused negatively correlated with clinical response. Non-parametric Wilcoxan rank-sum test was used to analyze the data with $P<0.05$ considered significant. To further analyze the role of $CD8^+$ TIL more closely, we plotted the extent of tumor shrinkage according to irRC (BOR) in all the treated patients versus the total number of $CD8^+$ T cells in the infusion product (FIG. 31F) and found a positive inverse correlation (r=−0.58 using Pearson correlation coefficient analysis). Similar results were found when the percentages of $CD8^+$ T-cells infused were plotted against the extent of tumor shrinkage (data not shown). We also determined whether any $CD4^+$ and $CD8^+$ T cells with a T-regulatory $CD25^+Foxp3^+$ phenotype were present. On average, both $CD4^+$ and $CD8^+$ cells co-expressing $CD25^+$ and $Foxp3^+$ represented only 0.5-1.9% of the total TIL population infused and no correlation between clinical response and this T-cell parameter was found (data not shown).

Figure 32B:
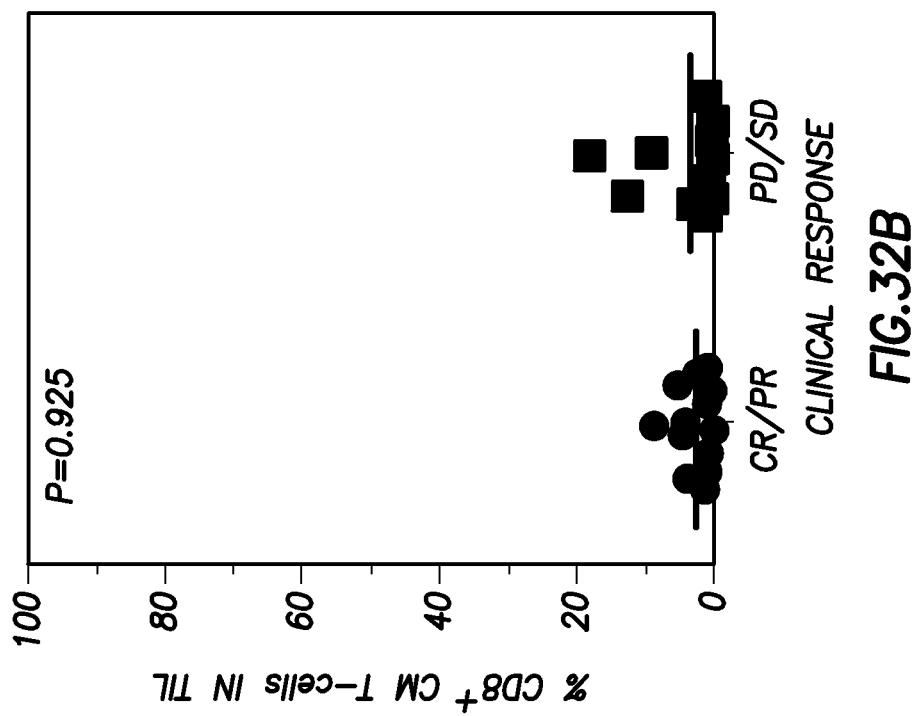
FIGS. 32A through 32D show the comparison of $CD8^+$ T-cell memory phenotype in responders and non-responders.
Figure 32A:
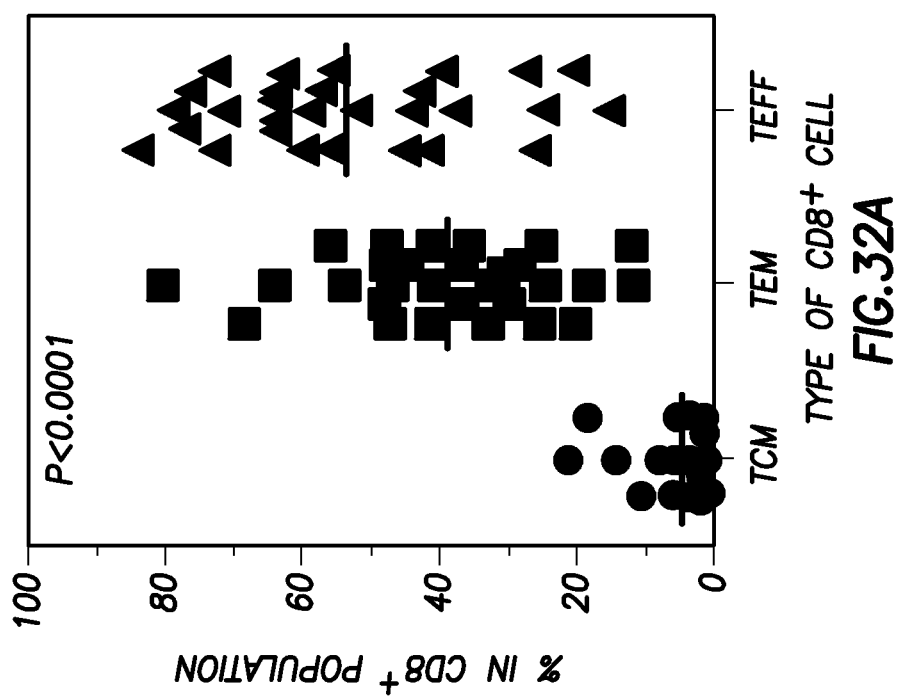
Figure 32D:
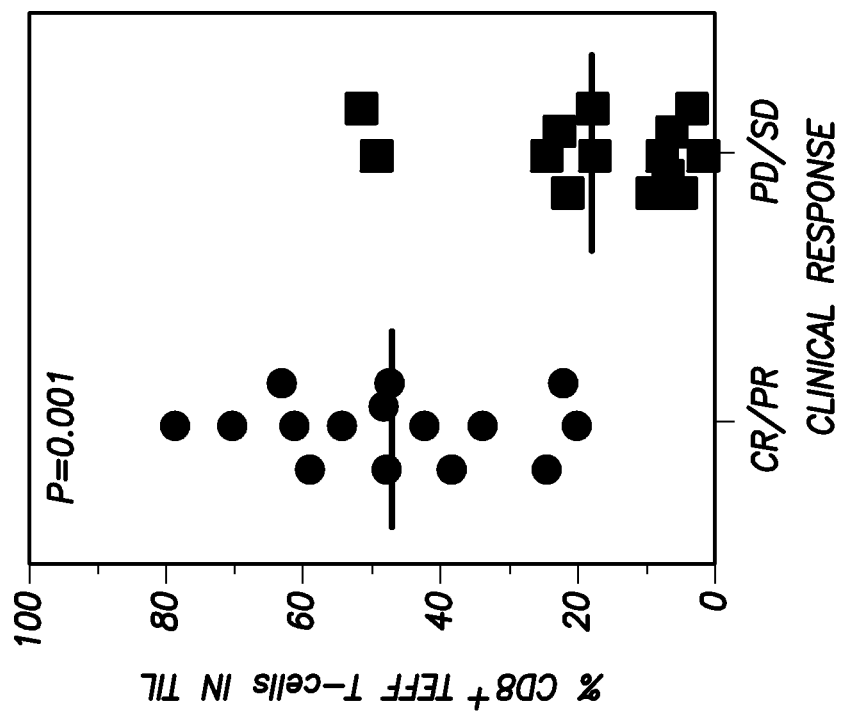
Figure 32C:
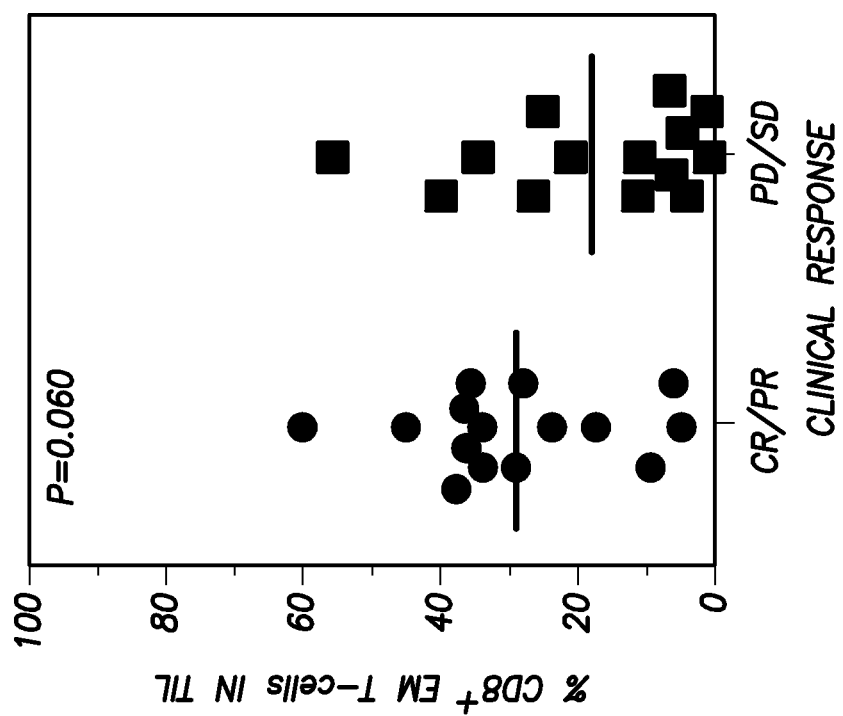

Having established that $CD8^+$ T cells in the TIL were critical, we then went on to further analyze the state of differentiation or memory status of the $CD8^+$ subset in the infused TIL. This analysis was also performed due to previous studies suggesting that the state of differentiation of the $CD8^+$ T cells in particular was associated with the type of clinical response. We stained the $CD8^+$ TIL for cell surface markers associated with naïve, effector-memory (TEM), central memory (TCM), and more differentiated effector (TEFF) T cells to better determine which $CD8^+$ sub-type best correlated with positive clinical activity. A viability dye was used to exclude any dead cells from the analysis. The bulk of the $CD8^+$ TIL infused were TEM ($CD8^+CD45RA^-CD62L^-CD27$) and TEFF ($CD8^+CD45RA^-CD62L^-CD27^-$) cells with few TCM ($CD8^+CD45RA^-CD62L^+CD27^-$) cells (FIG. 32A) and no naïve ($CD8^+CD45RA^+CD62L^+CD27^+$) cells (data not shown). Of note, some patients did have a significant frequency of TCM $CD8^+$ T cells infused (up to 21% of the $CD8^+$ subset). A three-way ANOVA was used to determine the significance between groups with $P<0.05$ considered to be significant. We then compared the frequencies of TCM, TEM, and TEFF cells in the $CD8^+$ subset with the type of clinical response and found that the responding patients had significantly higher frequency of TEFF cells over non-responders (FIG. 32D), while the TCM (FIG. 32B) and EM (FIG. 32C) subset did not exhibit a statistically significant difference. Significance was based on non-parametric Wilcoxan rank-sum tests with $P<0.05$ considered as statistically significant and $P<0.001$ considered to be highly significant.

Figures 33A, 33B, 33C:
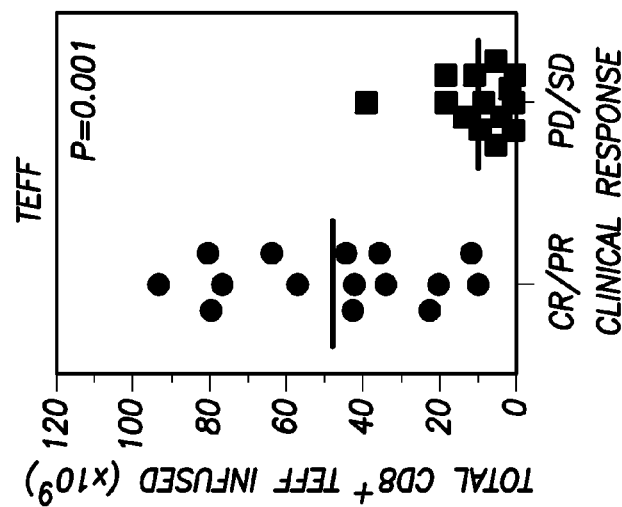
FIGS. 33A through 33C show that total $CD8^+$ $T_{EFF}$ infused correlates with clinical response.

Similar results were found when total $CD8^+$ TCM, TEM and TEFF cells infused was analyzed. Here, although higher numbers of total $CD8^+$ TEM cells was significantly associated with clinical response (p=0.00118), increased numbers of infused $CD8^+$ TEFF cell was much more strongly correlated with clinical response (p<0.0001) (FIG. 33A-C). Samples from the infused TIL from each treated patient were stained with fluorochrome-conjugated antibodies against CD8, CD27, CD62L, and CD45RA and analyzed by flow cytometry. The gated $CD8^+$ T cells were divided into TCM ($CD8^+CD27^+CD62L^+CD45RA^-$), TEM ($CD8^+CD27^+CD62L^-$ $CD45RA^-$), and TEFF ($CD8^+CD27^-CD62L^-$ $CD45RA^-$) subsets and the percentage of each subset in the viable cell gate multiplied by the total number of infused cells to determine the total numbers of $CD8^+$ TCM (FIG. 33A) TEM (FIG. 33B), and TEFF (FIG. 33C) infused versus the type of clinical response. Only the total infused $CD8^+$ TEFF showed a significant difference between responders (CR/PR) and non-responders (PD/SD). A Wilcoxon rank-sum analysis was used to determine the p-values.

CD27, a key TEM marker, has been shown to be downmodulated by high levels of that is added to the REP. To control for this, we incubated thawed post-REP TIL in low-dose, high-dose, or no IL-2 for 48 h and measured changes in cell surface CD27 on the $CD8^+$ T cells. However, still no significant difference in CD27 expression in the remaining $CD8^+$ T cells between responders and non-responders were found (data not shown). Thus, the $CD8^+$ TEFF phenotype ($CD27^-$) was not due to a transient loss of CD27 on the surface of TEM following the REP.

Figure 34D:
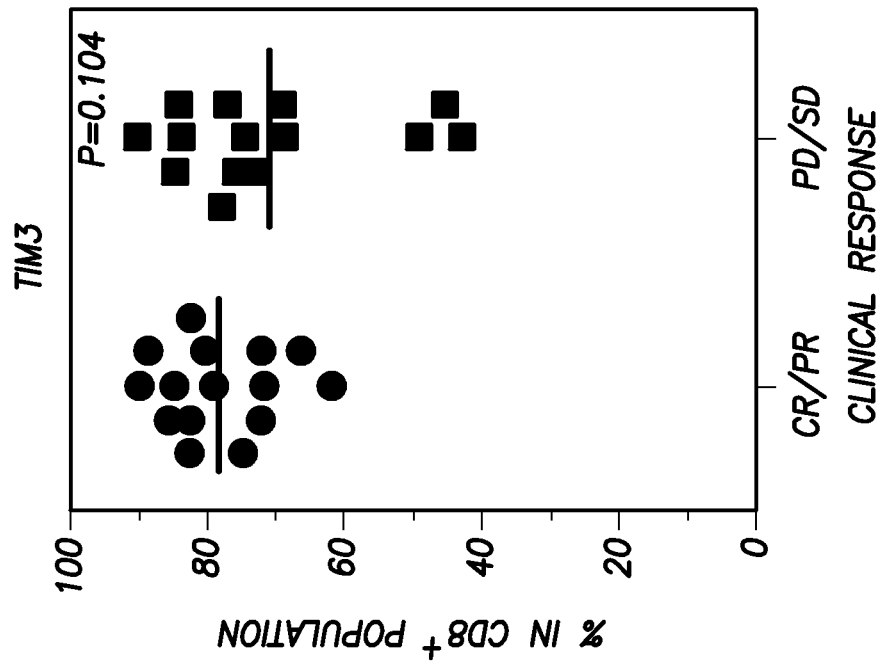
Figure 34C:
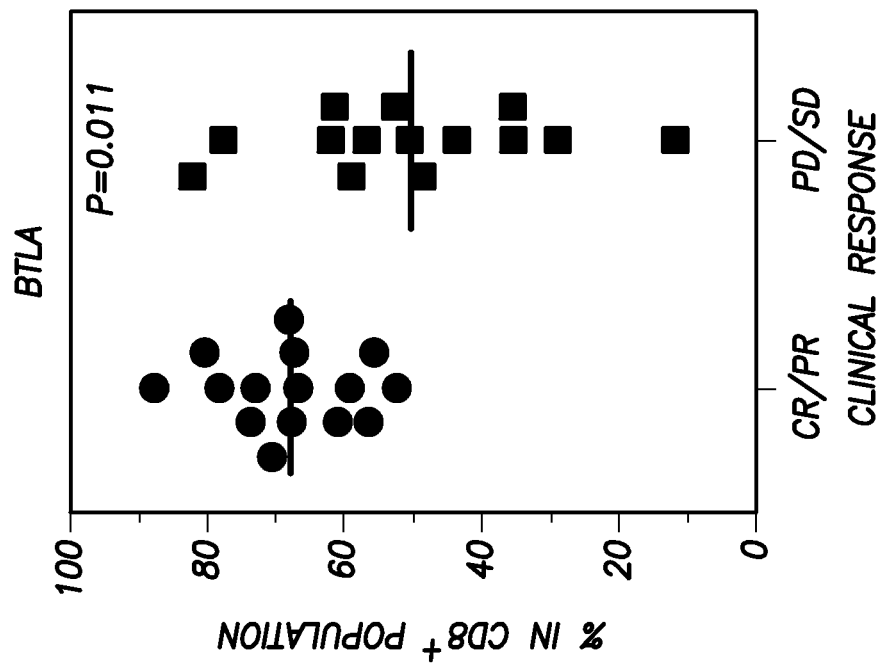

We went on to explore additional markers associated with CTL differentiation and T-cell exhaustion in the $CD8^+$ TIL subset and the $CD8^+$ TEFF and TEM subsets to further understand the possible nature of the T cells associated with objective tumor regression in the patients. These included PD-1, BTLA, and TIM-3 (inhibitory co-receptors on T cells), and Granzyme B (GB) and Perforin (markers for CTL). PD-1, BTLA, and TIM-3 were chosen as additional markers due to their demonstrated negative costimulatory function during T-cell activation in $CD8^+$ and $CD4^+$ T cells. GB and Perforin are critical cytolytic effector molecules in TEFF cells for tumor killing. As shown in FIG. 34A, a significant proportion of the infused. $CD8^+$ TIL expressed PD-1, BTLA, or TIM-3. TIM-3 was most highly expressed followed by BTLA and then PD-1. A wide range of PD-1 and BTLA frequencies in the $CD8^+$ cells was noted across the whole treated patient population, while the percentage of TIM-3 expression tended to be less variable (FIG. 34A). Unexpectedly, we found that higher frequencies of BTLA T cells in the $CD8^+$ TIL subset highly correlated with clinical response (FIG. 34C), while the frequency of $PD-1^+$ cells (FIG. 34B) and $TIM-3^+$ cells (FIG. 34D) was not correlated.

Figure 34F:
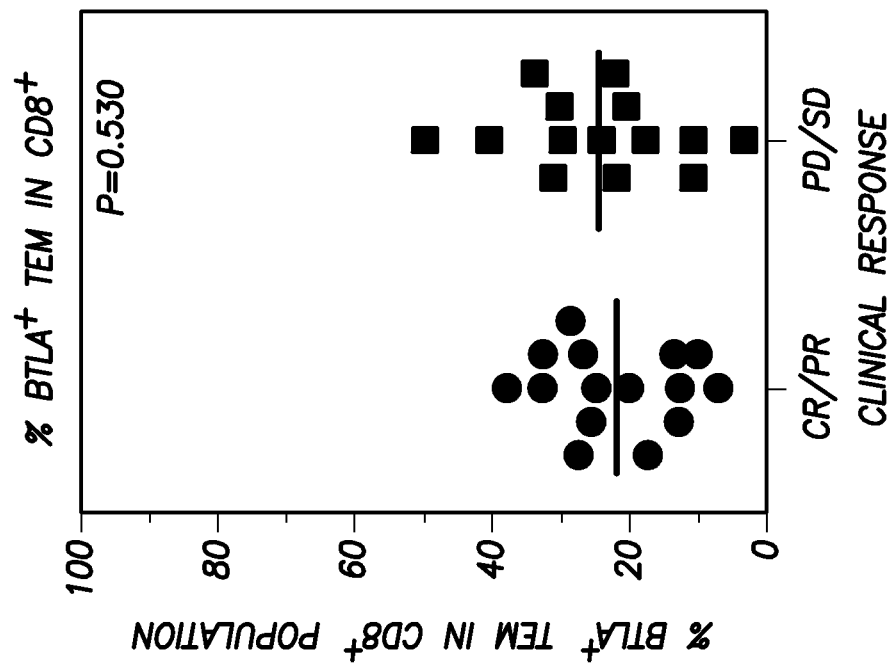
Figure 34E:
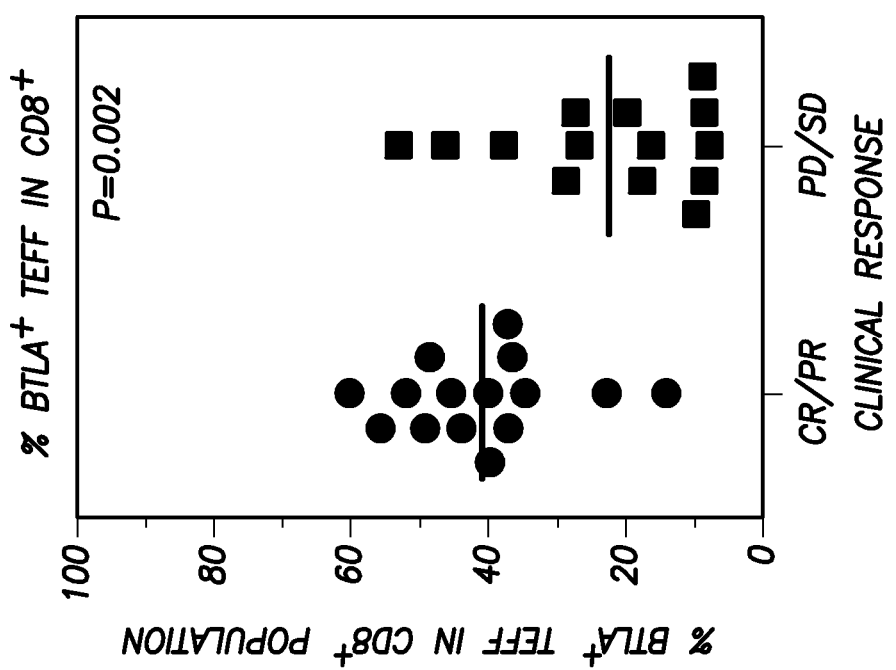

We then analyzed the role of BTLA by examining BTLA in the CD8+ TEFF and CD8+ TEM subsets. As shown in FIGS. 34E and 34F, the percentage of BTLA+ with a TEFF phenotype in the CD8+ cells (CD45RA−CD62L−CD27−BTLA−) was correlated with clinical response (p=0.002), while BTLA+ TEM (CD45RA−CD62L−CD27+BTLA+) in the CD8+ subset was not correlated (p=0.530).

We further analyzed the relationship between BTLA and PD-1 expression and found that a significant proportion of the CD8+ T cells co-expressed BTLA and PD-1, as shown in the representative flow cytometry dot plots in (FIGS. 35A-C). However, whether or not the CD8+ cells expressed PD-1, the ratio of BTLA+ cells was higher in the responding than in the non-responding patients. Staining for GB and Perforin found that both CD8+ TEM and TEFF cells expressed both molecules to different extents, but no correlation with the type of clinical response was found (data not shown). FIGS. 35A through 35C depict the results of TIL cells infused into Patient #2131, #2124 (responders) and Patient #2144 (non-responder) that were stained for CD8-Pacific Blue, CD4-PerCP-Cy5.5, BTL-PE (clone 1168), PD-1-PE-Cy7, and Aqua fixable cell viability dye. The cells were acquired on a FACSCantoII flow cytometer and analyzed using FlowJo and FACSDiva software. The cells were gated as indicated with the CD8+ live cells analyzed for BTLA and PD-1 expression.

Thus, immunophenotyping analysis of infused TIL found that the frequency and total number of CD8+ T cells was positively associated with clinical response. Among the CD8+ population, T cells with a more differentiated TEFF phenotype expressing the BTLA molecule correlated better with clinical response than TEM cells according to statistical analysis.

TCR Vβ Gene Expression Analysis and Persistence of TIL Vβ Clonotypes In Vivo

Figure 36A:
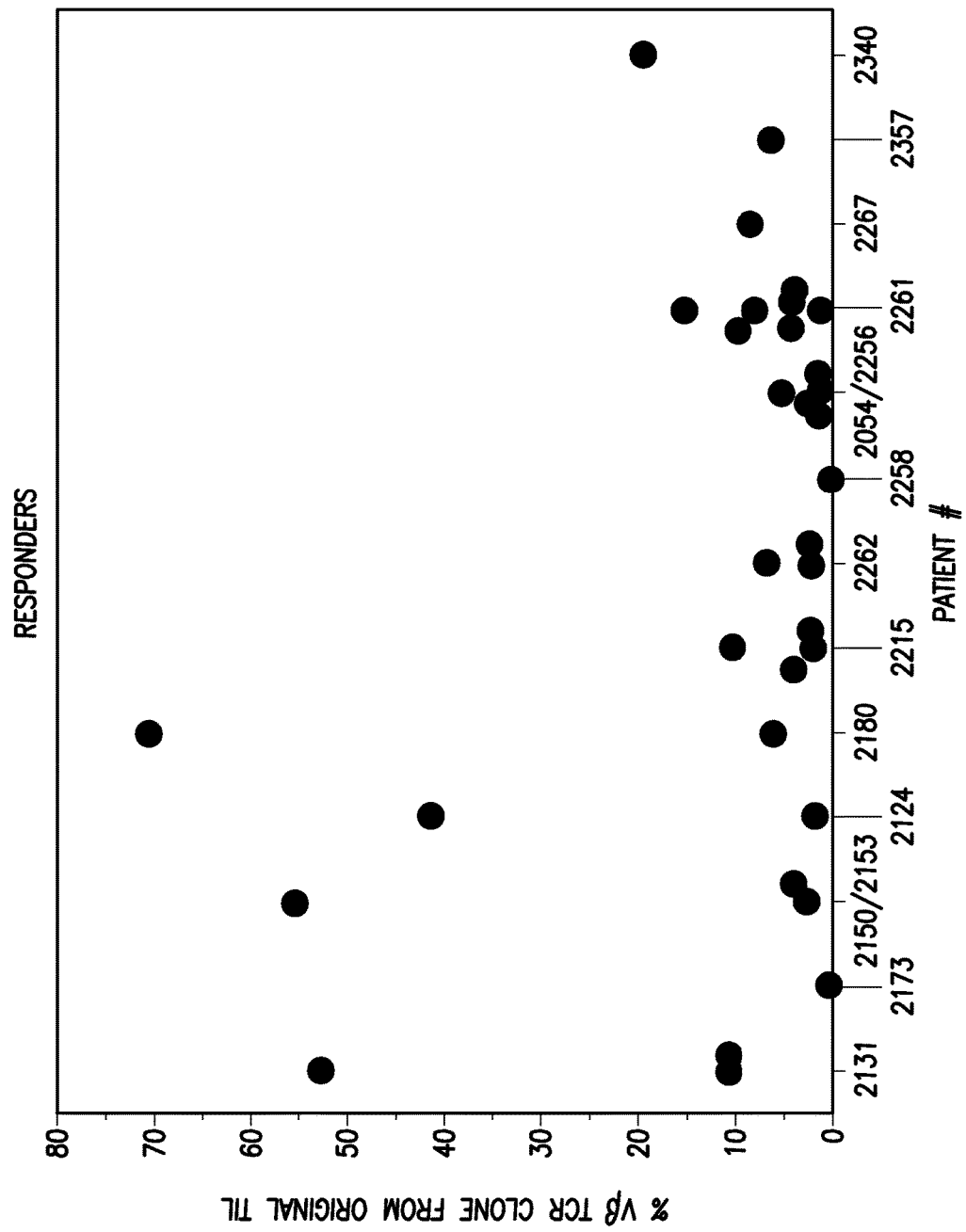
Figure 36B:
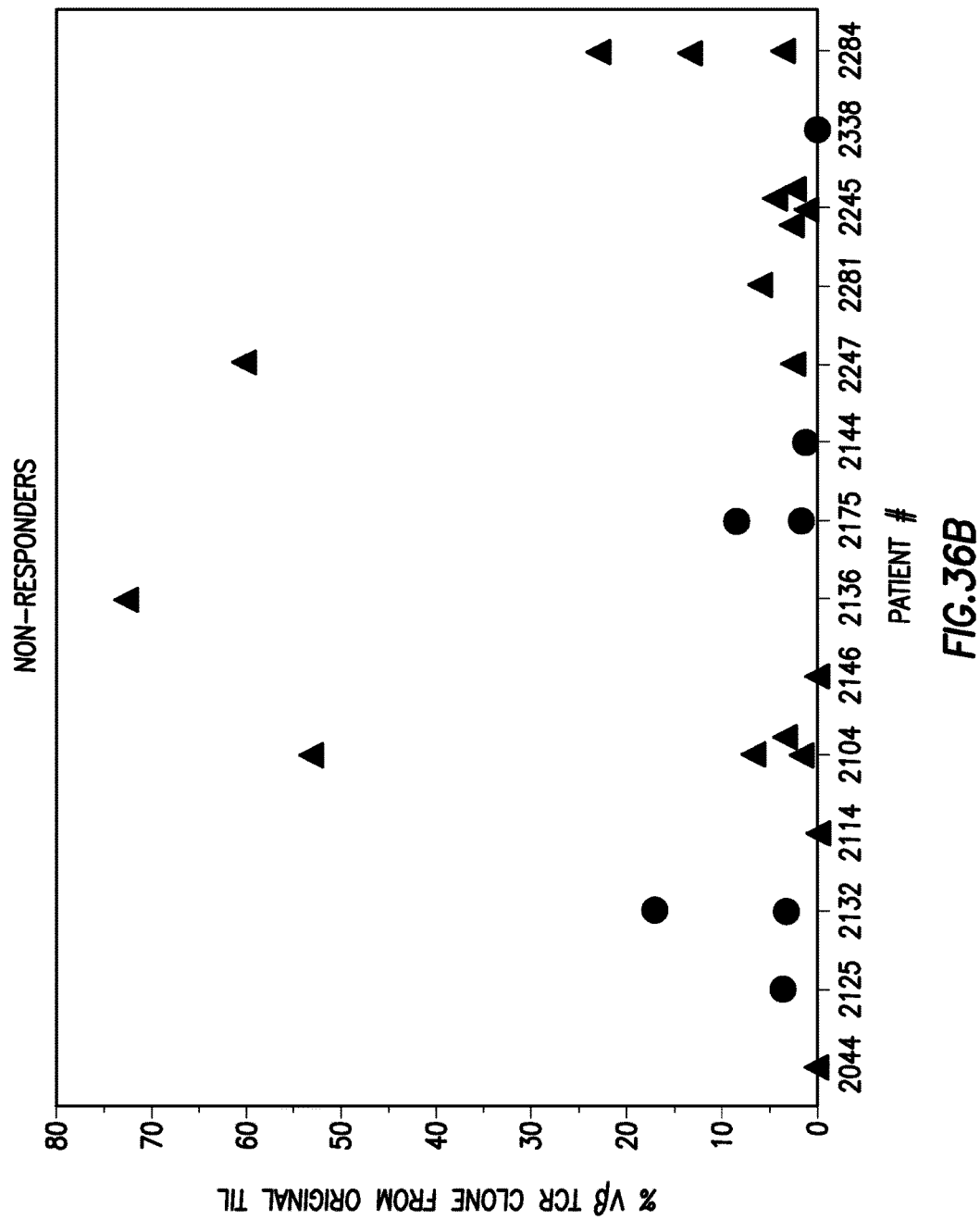

Persistence of infused TIL for at least 1 month following adoptive transfer into lymphoablated melanoma patients has been previously found to be associated with objective clinical response to therapy. We tracked the persistence of TIL in these patients by determining the maintenance of T-cell clonotypes using cloning and sequencing TCR VP genes in the TIL product and in blood samples taken at different times after TIL infusion. For each sample, up to 100 TCR Vβ clones were isolated and the CDR3 regions sequenced and identified. This analysis was performed for the first 27 treated patients (13 responders and 15 non-responders). FIGS. 36A and 36B compare the persistence of each dominant Vβ clone (found in the original TIL product) up to 42 days after adoptive transfer in responding versus non-responding patients (irRC). The filled circles represent infused TIL products composed mainly of CD8+ T-cells (>50% of the cells), while the filled triangle indicate TIL with predominantly CD4+ T cells (>50% of the infused cells). Responding patients had a higher diversity and percentage of persisting dominant Vβ clonotypes than non-responders. Overall, 8/13 (62%) of responders had at least two dominant TIL clone persist during the first 42 days, while only 6/14 (43%) of non-responders had at least two dominant TIL Vβ clones persisting. Non-responder patients found to have persistent Vβ clonotypes in the blood 42 days after infusion tended to have been infused with a TIL product mainly composed of CD4+ T cells. Thus, dominant Vβ clones in TIL with a majority of CD8+ T cells at the time of infusion correlated with clinical response. In two of the responders (e.g., Patients #2173 and #2258), we could not detect any of the original Vii clones by 42 days after adoptive transfer. However, these patients had Vβ clonotypes, undetected in the original TIL infusion product, emerge after this time point that persisted for at least 5-10 months correlated with the onset of tumor regression (data not shown).

We also tracked the changes in dominant TCR Vβ clonotypes in PBMC in a number of responding patients up to 22 months post TIL infusion. This was done to get a better idea of how the dominant TCR clones originally in the TIL persisted long term (>42 days) and whether new (initially undetectable) dominant clonotypes arose. Table 7 shows data from 4 responding patients. In each case, some original TIL dominant clonotypes contracted and disappeared, some expanded during this time interval, and some clones initially not detected in the infused TIL expanded at later time points. Notably, the appearance of these new clones was also associated with the disappearance of the original dominant clones. Table 8 immediately below shows the long term changes in the persistence of TCR Vβ clonotypes in the blood following TIL adoptive transfer in representative responding patients.

TABLE 8

| Patient # | TCR Vβ | Infused TIL (%) | 1 Month (%) | 5 Months (%) | 7 Months (%) | 11-13 Months (%) | 22 Months (%) |
|---|---|---|---|---|---|---|---|
| #2131 | VB4-1 | 56.8 | 52.5 | 14.3 | 12.7 | 2.4 | 6.9 |
|  | VB6-3 | 14.7 | 10.2 | 63 | 34.5 | 7.1 | 0 |
|  | VB7-9 | 0 | 0 | 4.8 | 7.3 | 40. | 29.3 |
|  | VB12-3 | 0 | 0 | 9.5 | 5.4 | 3.6 | 3.4 |
|  | VB20-1 | 12.6 | 10.2 | 4.8 | 1 | 1.2 | 0 |
|  | VB29 | 2 | 0 | 4.8 | 16.3 | 1.2 | 6.9 |
| #2150/2153 | VB11-2 | 11.1 | 2.5 | 12.1 | ND[b] | 0 | 0 |
|  | VB7-9 | 0 | 0 | 0 | ND | 3.6 | 3.6 |
|  | VB12-3 | 4.8 | 3.7 | 17.2 | ND | 5.6 | 7.1 |
|  | VB24-1 | 15.8 | 55.6 | 44.8 | ND | 27.7 | 19.6 |
|  | VB28 | 0 | 2.5 | 1 | ND | 11.1 | 0 |
| #2258 | VB4-3 | 23.8 | 0 | 0 | ND | 0 | ND |
|  | VB11-2 | 57.1 | 0 | 0 | ND | 0 | ND |
|  | VB29-1 | 6 | 0 | 0 | ND | 0 | ND |
|  | VB5-1 | 0 | 2.4 | 12.8 | ND | 10 | ND |
|  | VB5-6 | 0 | 23.8 | 29.5 | ND | 10 | ND |
|  | VB7-2 | 0 | 7.1 | 2.6 | ND | 0 | ND |
|  | VB9 | 0 | 4.8 | 0 | ND | 0 | ND |
|  | VB10-3 | 0 | 7 | 0 | ND | 0 | ND |
|  | VB12-3 | 0 | 2.4 | 10.3 | ND | 0 | ND |
|  | VB18 | 0 | 4.8 | 0 | ND | 0 | ND |

TABLE 8-continued

| Patient # | TCR Vβ | Infused TIL (%) | 1 Month (%) | 5 Months (%) | 7 Months (%) | 11-13 Months (%) | 22 Months (%) |
|---|---|---|---|---|---|---|---|
| | VB20-1 | 0 | 0 | 1.3 | ND | 3.3 | ND |
| | VB28 | 0 | 9.5 | 0 | ND | 0 | ND |
| #2124 | VB5-5 | 25.8 | 0 | 0 | ND | 0 | ND |
| | VB6-5 | 0 | 11.3 | 4.8 | ND | 0 | ND |
| | VB9 | 65.2 | 41.5 | 33.3 | ND | 57.1 | ND |
| | VB20-1 | 0 | 7.5 | 2.4 | ND | 1.2 | ND |
| | VB29-1 | 0 | 3.8 | 2.4 | ND | 2.4 | ND |
| #2180 | VB2 | 0 | 0 | 0 | ND | 6.3 | ND |
| | VB3-1 | 19.2 | 70.5 | 20.6 | ND | 0 | ND |
| | VB5-1 | 8.6 | 0 | 0 | ND | 0 | ND |
| | VB5-6 | 0 | 0 | 0 | ND | 6.3 | ND |
| | VB6-5 | 53.2 | 0 | 1.6 | ND | 0 | ND |
| | VB7-6 | 0 | 0 | 1.6 | ND | 3.1 | ND |
| | VB7-8 | 0 | 0 | 0 | ND | 6.3 | ND |
| | VB20 | 0 | 0 | 0 | ND | 6.3 | ND |
| | VB27 | 10.8 | 6.1 | 1.6 | ND | 0 | ND |

Another interesting observation was that some patients had a long period of stable disease following TIL transfer followed by an irRC or RECIST clinical response with a steady shrinkage of tumors between 6 and 20 months (e.g., Patient #2215). As shown in FIG. 36C, this delayed response was temporally associated with a gain in new previously undetectable Vβ clonotypes Vβ2, Vβ4.3, and Vβ6.2) and the disappearance of previous clonotypes in the original infused TIL. Because the cloning and CDR3 sequencing method may not have been sensitive enough to detect these new emergent clones in the original TIL (1/100 clone sensitivity), we performed RT-PCR for Vβ2, Vβ4.3, and Vβ6.2 from RNA obtained from the original TIL using specific primer sets. We were able to detect only Vβ4.3 in the original TIL by RT-PCR (FIG. 36D). Thus, it is possible that at least some Vβ clonotypes below the detection of the cloning method were indeed present in the original TIL at <1:100 frequencies and then expanded in vivo to become a dominant clonotype associated with tumor regression.

Figure 37:
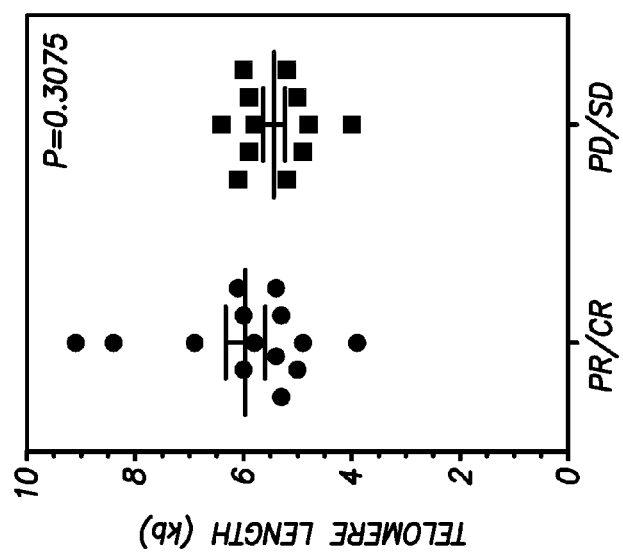
FIG. 37 shows that telomere length of infused TIL was not significantly different between responders and non-responders.

TIL of Responders and Non-Responders Did not Significantly Differ in Telomere Length The telomere length of infused TIL products was retrospectively evaluated from cryopreserved samples. A Southern blot method using complementary telomere repeat probes on restriction enzyme-digested genomic DNA was performed. Each TIL sample had a range of telomere lengths detected by blotting (usually between 11-2.5 kb) as expected in a heterogeneous population of cells in which there are cells of different ages that have undergone different numbers of cell divisions. The signal density frequency profile in each lane had a. Gaussian distribution (data not shown) allowing us to express the peak signal frequency as the mean telomere length for each sample. Using this approach, we found that overall the responders had a higher mean telomere length (6.0 kb±1.4) than the non-responders (5.4±0.7). However, statistical analysis using a non-parametric Wilcoxon signed rank test did not find a significant difference in these mean telomere lengths (FIG. 37). Cryopreserved TIL from the infusion product was thawed in batch and DNA isolated. The DNA was subjected to restriction endonuclease digestion, separated by agarose gel electrophoresis and probed by Southern blotting using a DIG-labeled telomeric repeat probe. The blots were developed using a chemoluminescent anti-DIG probe and exposed to art X-ray film. Telomere lengths were measured as described after densitometry scanning of the films.

Figure 38B:
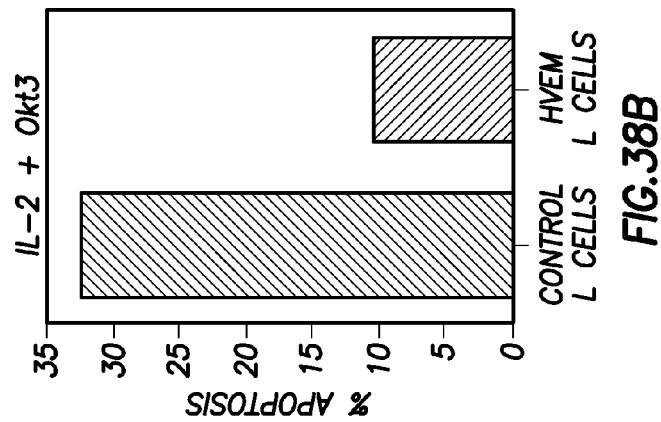
FIGS. 38A and 38B show that binding of BTLA by its ligand. Herpes Virus Entry Mediator (HVEM), prevents apoptosis or cell death of human $CD8^+$ melanoma TIL.
Figure 38A:
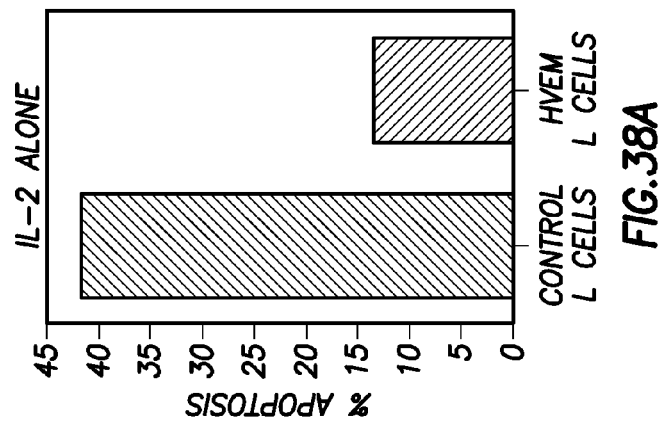

Binding of BTLA by its Ligand, Herpes Virus Entry Mediator (HVEM) Prevents Apoptosis or Cell Death of Human CD8+ Melanoma TIL In the first case, we tested the effects TIL co-cultured on HVEM+ CD32-L cells with low-dose (200 U/ml). (FIG. 38A). Control CD32-L cells without HVEM serves as the control. In FIG. 28A, CD8+ TIL were transferred from high-dose IL-2 (3,000 U/ml IL-2) to low-dose IL-2 (200 II/ml IL-2) that induces many cells to undergo apoptosis. The HVEM+ L cells prevented much of this apoptosis. As shown in FIG. 38B, we induced "activation-induced cell death" (AICD) of TIL by activating the TIL with anti-CD3 (OKT3) pre-loaded CD32-L TIL were stimulated with L cells coated with anti-CD3 antibody (OKT3, 200 ng/ml) for 5 days in addition to high-dose IL-2 to reactive the TIL through the T-cell receptor (TCR). TIL are sensitive to this form of TCR triggering apoptosis in the absence of adequate costimulation and many cell undergo activation-induced cell death (AICD). Again, co-culture with the HVEM L cells prevented much of the apoptosis observed.

Results

Adoptive transfer of highly expanded melanoma TIL into prior lymphoablated metastatic melanoma patients can mediate partial and complete regression of disease at multiple organ sites. Many of the tumor regressions were durable, with a significant fraction of complete and partial responders having a PFS of greater than 12 months. Our reported clinical response rates using irRC and RECIST were 46.9% (15/32 responders) and 418% (14/32) responders, respectively. These response rates are comparable to previously reported TIL therapy trials by two other groups (NCI in Bethesda, Md., and the Sheba Cancer Research Center in Israel) using similar TIL expansion and treatment protocols. It is also important to point out that a significant proportion of our partial responders had >90% tumor regression with only small CT-positive lesions remaining that were also found to be negative for glucose uptake by PET imaging. These may be dormant tumors, or even simply residual scar tissue and not tumor. These partial responders with these extensive tumor regressions are also the longest surviving patients (>24 months) in our trial.

Toxicities to different aspects of the therapy, including TIL infusion and were well tolerated, all expected, and easily managed in all patients. The number of cycles and dose of is an important question in TIL therapy due to its associated toxicities. HD IL-2 therapy should be compared with continuous low-dose IL-2 therapy following TIL infusion. If low-dose IL-2 yields comparable response rates, it would be beneficial towards more widespread application of ACT for melanoma.

We had no major technical issues with expanding TIL from melanoma tumor fragments with followed by a REP to generate the final TIL infusion product. Our success rate in expanding TIL (pre-REP TIL) from melanomas (60-65%) was also similar as in previous reported clinical trials using tumor fragments as the starting point. An important finding was that the total number of infused TIL and the fold expansion of TIL during the REP were critical parameters associated with clinical response. Responders were infused with on average almost twice the number of TIL (average of $93.8 \times 10^9$) than non-responders ($50.4 \times 10^9$), with $CD8^+$ T cells being the key subset, as discussed below. These results suggest that ACT using TIL should aim to infuse as many cells as possible after expansion protocols in vitro to ensure maximal clinical benefit.

Another parameter currently under debate is whether measurement of TIL anti-tumor reactivity in vitro can be used as a predictor for clinical response. We found that pre-REP TIL were anti-melanoma cell reactive in the majority of cases (>60%) when both autologous and allogeneic HLA-matched tumor targets were used. However, autologous tumor targets yielded a more consistent TIL response with >87% of patients having significant IFN-γ responses. Nevertheless, when all tumor targets or only autologous tumor targets were considered, there was no real correlation between clinical response and pre-REP anti-tumor IFN-γ responses. This may be due to the fact that we enriched TIL for tumor specificity whenever possible based on the availability of autologous targets or matched allogeneic targets, when selecting which TIL fragments to expand for patient therapy.

In addition, when autologous tumor is not available, HLA-matched allogeneic tumor can be used to assess tumor specificity if the antigen is a shared melanoma antigen, but if the assay is negative in this case, the TIL may still be tumor-specific against a unique autologous antigen or a shared antigen restricted by an alternative HLA molecule. Therefore, it is still not clear whether tumor-reactivity corresponds with clinical response, and future studies will need to be pursued with improved methods to obtain autologous tumor for predictive assays.

Besides evaluation of IFN-γ secretion in response to antigen, analyzing other cytokines, as well as the cytolytic capabilities of TIL may enhance future efforts to develop predictive assays of clinical response. One of the key functions TIL need to perform in vivo at the tumor site is tumor cell killing through apoptosis via cytolytic granule release by $CD8^+$ T cells or NK cells, NKG2D-mediated killing, or killing mediated through the fas-fas-ligand pathway. IFN-γ secretion may not necessarily be correlated with these CTL killing functions as for example in Fay vaccine trials and in elite HIV controllers, and may emerge to be a paradigm also in cancer. Thus, measurements of these additional parameters (e.g., Perforin and Granzyme B release, or CD107a release) may be more predictive.

In addition, other predictive biomarkers associated with the ability of TIL to induce objective clinical responses has become an important area of investigation. Besides enhancing the ability to personalize TIL therapy to the best subpopulation, increased knowledge in this area helps generate better TIL that will result in higher and more durable clinical responses. A number of markers such as telomere length of the infused T cells, the type of T cells ($CD4^+$ versus CD8) and their differentiation status, as well as the differential expression of positive and negative T-cell costimulatory molecules, can affect both the persistence of adoptively transferred T cells, their continued expansion after antigen contact, and their effector function in vivo.

The first striking observation made was the number of TIL infused was critical for inducing an objective clinical response and that $CD8^+$ T cells is an active component. Both a higher percentage and higher total number of infused $CD8^+$ T cells was significantly associated with response, while the opposite trend was found with $CD4^+$ T cells. This suggests that $CD8^+$ T cells are the key driving force behind the anti-tumor activity of TIL. In certain regards, CTL activity attributed to $CD8^+$ T cells, but proof of this association in TIL therapy has been lacking until now.

The positive role of $CD8^+$ T cells leads to another observation regarding the state of $CD8^+$ CTL differentiation in the TIL product and how it is related to response. The state of $CD8^+$ CTL differentiation in TIL relates both to the ability of the transferred T-cells to expand and repopulate the host and their ability to mediate potent anti-tumor CTL activity. We found that most of the $CD8^+$ T-cells in TIL were TEM ($CD45RA^-CD62L^-CD27^-CD28^+$) or more-differentiated EFF ($CD45RA^-CD62L^-CD27^-CD28^-$) cells, with negligible levels of naïve and central memory cells. Although previous data has suggested that the number and percentage of infused $CD8^+CD27^+$ TEM cells is the critical component, we found that both TEM and TEFF $CD8^+$ cells were important. In fact, our study found that TEFF cells unexpectedly more critical in mediating anti-tumor responses when examining the level of statistical significance. We found that $CD8^+$ TIL with a more differentiated TEFF phenotype express higher levels of Granzyme B and Perforin and are stronger on a per cell basis at killing melanoma cells. The positive association of both $CD8^+$ TEM and TEFF cells with positive clinical responses suggests perhaps that both cells may play a synergistic role in controlling tumor growth.

For example, $CD8^+$ TEFF cells rapidly home into metastatic deposits and mediate an early, more rapid phase of tumor killing, while the $CD8^+$ TEM cells persist longer, are capable of expansion, and mediate longer-term tumor control. At present, how these markers can change in vivo after adoptive transfer with either $CD8^+$ T-cells with a TEM profile rapidly losing CD27 and CD28, or with some TEFF cells re-gaining CD27 and/or CD28 expression, is unclear. One explanation may be $CD8^+$ T cells in transferred TIL clones may re-gain CD27 and CD127 (IL-7Rα) expression in vivo.

Also, the rapid expansion of TIL for ACT has been shown to induce a significant amount telomere erosion. However, we have found that a considerable amount of telomere length is still present in these cells that can support further expansion in vivo. Nevertheless, the degree of telomere loss has been considered a potential factor inducing cell senescence limiting the persistence and anti-tumor function in vivo after adoptive transfer. Thus, the lack of association between TIL telomere length and the type of clinical response we found was unexpected based on previously published FlowFISH data indicating that longer telomere length, reminiscent of "younger" TEM cells, was positively correlated with higher partial and complete response rates. We determined telomere length using the Southern blotting technique (the gold standard for direct telomere length measurement in cells) to verify our data using two independent methods.

Previous studies have used only Flow-FISH and, although this is a quantitatively robust assay, in our experience we have found that FlowFISH can be imprecise with assay-to-assay variability in fluorescence intensities detected in the same samples. The role of both T cells with a "younger" TEM and "older" TEFF phenotype with clinical response in our study here may account for the lack of this "telomere effect". The tack of a telomere effect in our study when these measurements are performed on the infused TIL product also may not be that surprising because the situation may change dramatically in vivo where "younger" cells may rapidly divide and quickly shorten their telomeres, "older" (TEFF) cells may divide more slowly and preserve what telomere length they have over a longer period of time, and where telomerase expression increasing the length of telomeres may be induced by homeostatic cytokines (e.g., IL-15) and co-stimulatory signals. Furthermore, taken as a whole along with other parameters in a multivariate setting (as opposed to a simple paired t-test), the overall contribution of telomere length may be minimal when total numbers of TIL infused, percentage of $CD8^+$ T cells, effector phenotype, and other TIL and patient parameters are taken into consideration.

One of the most unexpected findings of this study came when we examined the expression of three previously characterized "negative" co-stimulatory molecules on T cells, PD-1, BTLA and TIM-3. PD-1 is a member of the Ig family of receptors along with CD28 and CTLA-4. PD-1 is induced after T-cell activation and is found on chronically-stimulated (exhausted) TEM and TEFF CD8 cells, where it plays a role as a molecule inhibiting T-cell proliferation after binding to either PD-L1 (also called B7-H1) or PD-L2 (also called B7-DC) along with another marker of hypo-responsive cells called TIM-3 that binds Galectin-9. PD-1 has been found to be expressed on melanoma TIL and transmits a negative signal inhibiting antigen-specific TIL cell division. PD-1 ligands can be expressed by antigen-presenting cells and tumor cells and Galectin-9 is expressed by multiple types of tumor cells as well as liver parenchymal, and endothelial and epithelial cells. BTLA was found more recently as a more distant member of the Ig family expressed that is constitutively on naïve T cells and can be further induced upon T-cell activation and activates the SHP1 and SHP2 phosphatases that dampen T-cell activation signals. BTLA is unusual however, in that it does not bind to other Ig family member ligands, but rather has been shown to interact with HVEM, a member of the TNF-R family of receptors.

A significant heterogeneity in PD-1 and BTLA expression was found in the final TIL products on both the $CD8^+$ and $CD4^+$ T cells. Surprisingly, we found that an increased frequency of $BTLA^+$ cells in the $CD8^+$ TIL subset as well as higher numbers of infused $CD8^+BTLA^+$ TIL were both highly associated with a positive clinical response, while BTLA expression on $CD4^+$ T cells in the TIL had no relationship. The extent of PD-1 expression on either $CD8^+$ or CD4+TIL however did not seem to be related to clinical response with non-responders not having a higher frequency of PD-$1^+$ T cells. Although, the association of higher BTLA expression on $CD8^+$ TIL and clinical response will need to be confirmed in future clinical trials, it suggests that BTLA along with CD8 staining may be a biomarker distinguishing a more efficacious TIL infusion product.

BTLA may play a functional role in $CD8^+$ TIL, and/or it may be simply a marker for TIL. Although BTLA has been found to be a negative costimulatory molecule during naïve T-cell activation, its role in effector and effector-memory cells has not yet been clearly defined. The role of BTLA recently has become a matter of controversy, as recent data suggests that it can also play a positive role in maintaining T-cell responsiveness and survival in the face of chronic antigenic stimulation in some systems. Its function may change depending on the phase of the immune response and state of differentiation of the T cell. Thus, BTLA may function through a number of mechanisms leading to a "positive" effect on TIL survival and response to IL-2. For example, it may attenuate strong TCR signals in vivo and prevent activation-induced cell death. HVEM ligation by LIGHT has been found to induce NFκB activation through the classical p50-RelA pathway and indirectly the activation of AKT. Recently, BTLA also has been found to bind HVEM and trigger signaling through the classical NFκB pathway in human T cells. We have found that all TIL express HVEM leading to the possibility that a BTLA-HVEM interaction may activate pro-survival signaling through HVEM in TIL.

Finally, our data shed light on how TCR antigen specificities and the appearance of new TCR clonotypes may play a role in long term tumor control following ACT and the role of the initial TIL infusion in this regard. A notable observation in our studies was that although dominant TCR clonotypes exhibited improved short term persistence (over the first 42 days) in responding patients, many times these original clones disappeared (or became undetectable) correlating with a rise in previously undetectable dominant TCR clonotypes in the blood months after TIL infusion. Although the limits of sensitivity of our Nip gene amplification and cloning method can account for this, it is also plausible that these indeed are newly arising TCR clonotypes as a result of expansion of endogenous T cells reactive against tumor antigens. It is possible that TIL (much like a cancer vaccine) causes a wave of tumor destruction of variable duration and leads to the release of new antigens (antigen spreading) or new epitopes from previously recognized antigens (epitope spreading). This would then activate either previous latent clones in the original TIL or clones of endogenous T cells recovering after lymphodepletion. This can also explain why many non-responding patients exhibited some degree of disease stabilization, or even a short term limited regression (FIG. 29), and then rapidly progressed after a month. An intriguing possibility is that antigen or epitope spreading may have been limited in these patients and/or that new clones not present in the original TIL could not expand and further amplify the initial antitumor response. A more comprehensive and sensitive Vβ and Vα clonotype analysis using high-throughput sequencing and new computational approaches will be required to answer this question.

In summary, we have found that clinical response from TIL in metastatic melanoma patients is associated with $CD8^+BTLA^+$ TIL and that both enactor memory and terminal effector T-cells are important in inducing responses. Refining the role of BTLA in the antitumor response, enhancing predictive assays of response, and developing strategies to generate more effective T-cells is proposed. The ability to gene modify T-cells provides an opportunity to modify the phenotype prior to infusion. For example, to enhance the localization of TIL to the tumor site, insert the CXCR2 gene into the TIL, which will allow the cells to migrate towards chemokines produced by most melanomas.

We claim:

1. A method of treating a cancer patient comprising administering to the patient an effective amount of anti-cancer T-cells wherein the anti-cancer T-cells are selected or enriched for BTLA-positive T-cells.

2. The method of claim 1, wherein the patient has a melanoma.

3. The method wherein the patient has metastatic melanoma.

4. The method of claim 1, further comprising administering IL-2 to the patient.

5. The method of claim 1, further comprising administering a platelet and red blood cell transfusion to the patient.

6. The method of claim 1, wherein the patient has been lymphoablated prior to the administering.

7. The method of claim 1, wherein the T-cells are obtained from the patient.

8. The method of claim 7, wherein the T-cells are obtained from tumor sample from the patient.

9. The method of claim 1, wherein the T-cells are expanded in vitro prior to said administering.

10. The method of claim 1, wherein the T-cells comprise $CD8^+$, TEM or TEFF cells.

11. The method of claim 1, further comprising obtaining a population of anti-cancer T-cells and selecting for BTLA-positive T cells prior to the administering step.

12. The method of claim 1, wherein the patient is administered $8\text{-}150 \times 10^9$ cells.

* * * * *